(12) United States Patent
Ball

(10) Patent No.: US 7,449,028 B2
(45) Date of Patent: Nov. 11, 2008

(54) MODULAR TOTAL ELBOW PROSTHESIS, HUMERAL COMPONENT AND ASSOCIATED KIT

(75) Inventor: Robert J. Ball, San Marcos, CA (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/255,481

(22) Filed: Oct. 21, 2005

(65) Prior Publication Data

US 2006/0247786 A1    Nov. 2, 2006

Related U.S. Application Data

(60) Provisional application No. 60/623,372, filed on Oct. 29, 2004, provisional application No. 60/623,195, filed on Oct. 29, 2004.

(51) Int. Cl.
*A61F 2/38* (2006.01)

(52) U.S. Cl. ............................. 623/20.13; 623/20.11

(58) Field of Classification Search ............. 623/20.11, 623/20.12, 20.13, 18.11
See application file for complete search history.

(56) References Cited

U.S. PATENT DOCUMENTS

| | | | |
|---|---|---|---|
| 3,708,805 A | 1/1973 | Scales et al. | |
| 3,939,496 A | 2/1976 | Ling et al. | |
| 4,224,695 A | 9/1980 | Grundei et al. | |
| 4,293,963 A | 10/1981 | Gold et al. | |
| 5,367,121 A * | 11/1994 | Yanase | 84/666 |
| 5,376,121 A | 12/1994 | Huene et al. | |
| 6,027,534 A | 2/2000 | Wack et al. | |
| 6,217,616 B1 * | 4/2001 | Ogilvie | 623/20.11 |
| 6,290,725 B1 | 9/2001 | Weiss et al. | |
| 6,379,387 B1 * | 4/2002 | Tornier | 623/20.12 |
| 6,767,368 B2 * | 7/2004 | Tornier | 623/20.12 |
| 6,790,234 B1 * | 9/2004 | Frankle | 623/19.12 |
| 2002/0165614 A1 * | 11/2002 | Tornier | 623/20.12 |
| 2003/0208276 A1 * | 11/2003 | Berelsman et al. | 623/20.11 |
| 2004/0186580 A1 * | 9/2004 | Steinmann | 623/20.11 |

OTHER PUBLICATIONS

De Puy Orthopaedics, Inc, Acclaim Total Elbow System, 2002, 0601-65-050 (Rev. 1), DePuy Orthopaedics, Inc., Warsaw, IN, USA.
Stryker Orthopaedics, Solar Elbow, Dec. 7, 2005, Stryker, Internet, http://stryker.com/jointreplacements/sites/solar/elbow/index.php.

* cited by examiner

*Primary Examiner*—Daniel L Robinson

(57) ABSTRACT

An ulnar assembly for use with a humeral component to form an elbow prosthesis is provided. The ulnar assembly includes a first component including a portion thereof defining a stem for implantation in a cavity formed in the ulna. The first component defines a longitudinal axis thereof generally coincident with the longitudinal axis of the ulna. The ulnar assembly also includes a second component attached to the first component. The second component is attachable and removable from the first component along the longitudinal axis of the first component. One of the first component and the second component include an external taper. The other of the first component and the second component defines an internal taper therein adapted to receive the external taper.

11 Claims, 52 Drawing Sheets

US 7,449,028 B2

MODULAR TOTAL ELBOW PROSTHESIS, HUMERAL COMPONENT AND ASSOCIATED KIT

CROSS-REFERENCE TO RELATED APPLICATIONS

This Application is a Utility Application based upon U.S. Provisional Patent Application, Ser. No. 60/623,372 filed Oct. 29, 2004, entitled "MODULAR TOTAL ELBOW PROSTHESIS & INSTRUMENTS AND ASSOCIATED METHOD and upon U.S. Provisional Patent Application, Ser. No. 60/623,195 filed Oct. 29, 2004, entitled "MOBILE BEARING TOTAL ELBOW PROSTHESIS & INSTRUMENTS AND ASSOCIATED METHOD". Cross reference is made to the following applications: U.S. Provisional Patent Application, Ser. No. 60/623,372 filed Oct. 29, 2004, entitled "MODULAR ELBOW PROSTHESIS & INSTRUMENTS AND ASSOCIATED METHOD", U.S. Provisional Patent Application, Ser. No. 60/623,195 filed Oct. 29, 2004, entitled "MOBILE BEARING TOTAL ELBOW PROSTHESIS & INSTRUMENTS AND ASSOCIATED METHOD", as well as U.S. Pat. application Ser. No. 11/256,576 entitled "MODULAR TOTAL ELBOW PROSTHESIS, INSTRUMENTS AND ASSOCIATED METHOD", U.S. patent application Ser. No. 11/255,540 entitled "MODULAR TOTAL ELBOW HUMEPAL COMPONENT AND ASSOCIATED METHODS", U.S. patent application Ser. No. 11/255,504 entitled "MOBILE BEARING TOTAL ELBOW PROSTHESIS, HUMERAL COMPONENT, AND ASSOCIATED KIT" and U.S. patent application Ser. No. 11/256,010 entitled "MOBILE BEARING TOTAL ELBOW PROSTHESIS, ULNAR COMPONENT, AND ASSOCIATED METHOD" all filed concurrently herewith and all incorporated herein by reference.

TECHNICAL FIELD OF THE INVENTION

The present invention relates generally to the field of orthopedics, and more particularly, to artificial joints and, in particular, to a modular elbow prosthesis.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a complicated movement, including a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident for, example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

In the human elbow, three degrees of freedom are present. These are flexion-extension, varus-valgus carrying angle and axial rotation.

Various elbow prosthesis have been constructed as a replacement for the natural human elbow. The two basic types of elbow prosthesis known in the prior art are semi-constrained and unconstrained. In semi-constrained prosthesis, the prosthetic joint is held together mechanically, by components of the prosthesis. Such devices are shown, for example, in U.S. Pat. No. 5,376,121 to Huene et al., U.S. Pat. No. 3,708,805 to Scales, et al., U.S. Pat. No. 3,939,496 to Ling, et al., and U.S. Pat. No. 4,224,695 to Grundei, et al. In an unconstrained device, the prosthetic device is held together by the patient's natural soft tissues. Such a device is shown in U.S. Pat. No. 4,293,963 to Gold, et al.

In each of these devices, one portion of the prosthesis is implanted in the humerus of the patient and the other portion is implanted in the ulna. The two portions then mate in some manner to allow articulation of the joint. In the '695 patent to Grundei, et al., an additional portion of the prosthesis is implanted in the radius of the patient.

A surgeon may not always know prior to beginning an operation whether a patient would be better served by a semi-constrained or unconstrained elbow prosthesis. Thus, it would be desirable to provide an elbow prosthesis that may be utilized in either the semi-constrained or unconstrained manner.

It may also be necessary to convert an unconstrained elbow prosthesis to a semi-constrained one, or vice versa, after implantation and use for a period of time. In order to do so, it is typically necessary to remove the portion of the prosthesis implanted in the humerus and ulna and to replace the entire prosthesis with either the semi-constrained or unconstrained variety.

Prosthetic elbows currently marketed typically can be implanted to operate in one of two ways. These two ways are an unconstrained or unlinked manner and the other way is a semi-constrained or linked manner. Unconstrained prosthetic elbows are more generally indicated for osteoarthritic or post traumatic patients with strong soft tissues about the elbow. Such patients have joints with surfaces that are arthritic and painful.

Typically, unconstrained elbows are designed with, for example, a metal humeral articulating surface and a polyethylene ulnar articulating surface. Each of these components have matching convex and concave surfaces, respectively.

Alternatively, semi-constrained prosthesis are used with inflammatory disease. The inflammatory disease results in the patient having weaker soft tissue and significant bone erosion. The weaker soft tissue and bone erosion makes the use of an unconstrained elbow more difficult in that the soft tissues are not of sufficient strength to properly contain the prosthetic components in contact with each other. A semi-constrained prosthesis uses a linkage pin at the elbow axis of rotation. The progression of osteoarthritis and other joint diseases may create a situation in which a patient first implanted with a unconstrained elbow prosthesis may, due to further loss of soft tissue, require the use of a semi-constrained prosthesis. This need for a different prosthesis may create a significant issue for the patient. The removal of particularly the stem portions of the prosthesis after being implanted for some time is difficult.

A product sold as the Acclaim Elbow™ sold by DePuy Orthopaedics, Inc., Warsaw, Ind. has been designed to attempt to alleviate at least partially the problem of interoperatively converting from an unconstrained elbow to a semi-constrained elbow. The Acclaim Elbow™ can be more readily understood by reference to U.S. Pat. No. 6,027,534 and No. 6,290,725 incorporated herein in their entireties by reference.

While the Acclaim Elbow™ permits the conversion from an unconstrained elbow to a semi-constrained elbow without removing the entire prosthesis from the patient, the use of the Acclaim Elbow™ makes use of an axis pin mechanism for preventing dislocation and positioning of the axis of articulation. The Acclaim Elbow™ requires substantial amounts of condylar bone to be removed if the pin poly axis assembly wears and needs replacement.

The current Acclaim Elbow™, as well as other competitive elbow prosthesis, have a shape and configuration that may not be ideally suited to each particular patient's anatomy in that a patient, depending on gender and size, may have a bone structure that is not well suited to available implants.

Current elbow prosthesis have configurations that provide for complicated components for which the cost of manufacturing may be quite high.

Currently marketed elbow prosthesis make use of a locking axis pin as the main element of articulation for the semi-constrained form of the elbow prosthesis. Elbow prosthesis also include drilling techniques for condyles of the bone for removal of the poly/pin assembly. Such removal of bone to permit the removal of a prosthesis may severely weaken the supracondylar regions of the humerus. Such bone removal may weaken the support structure for the prosthesis and may lead to earlier failure.

SUMMARY OF THE INVENTION

The present invention provides for an elbow prosthesis that may be more easily removed from the patient and may be more easily repaired or revised when components in the prosthesis may warrant such a procedure. The present invention provides for an enhancement of the pin axis by modifying the modular features of the prosthesis so that the junction is further proximal in the humeral component. A set of stem components of the prosthesis are designed to fit patients anatomically. Such stems are adapted for indications that would be available to fit with several types of articulating components.

The components of the present invention may have varying anatomical features to match patient anatomy as well as to offer the ability to convert from an unconstrained to a semi-constrained elbow prosthesis. Further, the articulating surface of the humerus may be modified to allow for the use of a radial head prosthesis.

The modularity of the design of the present invention provides for a humeral articulating head for an unconstrained elbow prosthesis to be removed and replaced by a yoke-type device for a semi-constrained elbow prosthesis with removal of minimal bone or soft tissue.

The present invention may be configured to allow the implant to be converted from an unconstrained to a semi-constrained prosthesis in a manner such that the pin/poly axial assembly may be removed from the bone prior to its disassembly. The new modular junction between the stem and the articulating head allows one to customize the size and shape of the implant for the patient's anatomy and also allows the bearing mechanism to be assembled after cementing the prosthetic stem.

The stem of the prosthesis of the present invention may have a tapered post that is concentric to the stem longitudinal axis and that may extend distally. The tapered post may provide a secure fit with a tapered hole in an unconstrained and semi-constrained bearing component.

A wide range of embodiments may be obtained from the present invention, including a reversal of tapered assembly mechanisms; a further modularity of the stems, bodies and heads; a dual, square taper; and other configurations.

The modularity of the design of the embodiments of the present invention allows many options combining specially designed components to be combined to create a prosthesis, which more accurately fits patient needs.

The present invention may include a three part configuration that allows the surgeon to fit the stem, the body, and the head separately.

The modularity also offers the option of incorporating a mobile bearing concept into the design. One way to perform the mobile bearing concept is to simply allow the junction between the humeral stem and the head to be a loose fit and allow translation and rotation about this junction.

According to one embodiment of the present invention, there is provided a humeral assembly for cooperation with an ulnar component to form a total elbow prosthesis. The humeral component includes a first component having a portion thereof defining a stem for implantation in a cavity formed in the humerus. The first component defines a longitudinal axis thereof generally coincident with the longitudinal axis of the humerus. The humeral component also includes a second component attached to the first component. The second component is attachable and removable from the first component along the longitudinal axis of the first component.

According to another embodiment of the present invention there is provided an ulnar assembly for use with a humeral component to form an elbow prosthesis. The ulnar component includes a first component having a portion thereof defining a stem for implantation in a cavity formed in the ulna. The first component defines a longitudinal axis thereof generally coincident with the longitudinal axis of the ulna. The ulnar component also includes a second component attached to the first component. The second component is attachable and removable from the first component along the longitudinal axis of the first component.

According to yet another embodiment of the present invention there is provided an elbow prosthesis including an ulnar component. The ulnar component has a first portion thereof implantable in a cavity formed in the ulna and a second portion connected to the first portion. The elbow prosthesis also includes a humeral component including a first portion having a portion thereof defining a stem for implantation in a cavity formed in the humerus. The first portion defines a longitudinal axis thereof generally coincident with the longitudinal axis of the humerus. The humeral component includes a second portion attached to the first portion. The second portion is attachable and removable from the first portion along the longitudinal axis of the first portion.

According to a further embodiment of the present invention there is provided an elbow prosthesis including an ulnar component. The ulnar component has a first portion with a portion thereof defining a stem for implantation in a cavity formed in the ulna. The first portion defines a longitudinal axis thereof that is generally coincident with the longitudinal axis of the ulna. The ulnar component also includes a second portion attachable and removable from the first portion along the longitudinal axis of the first portion. The elbow prosthesis also includes a humeral component. The humeral component has a first portion thereof implantable in a cavity formed in the humeral and a second portion connected to the first portion.

According to yet another embodiment of the present invention there is provided a kit for use in performing total elbow arthroplasty. The kit includes an ulnar stem component for implantation at least partially in the humeral medullary canal. The kit also includes an ulnar hinge component attachable to the ulnar stem and a humeral stem component for implantation at least partially in the ulnar medullary canal. The humeral stem component defines a longitudinal axis thereof. The kit also includes a first humeral hinge component attachable to the humeral stem component. The first humeral hinge component is attachable and removable from the humeral stem component along the longitudinal axis of the humeral stem component. The kit also includes a second humeral hinge component attachable and removable from the humeral stem component along the longitudinal axis of the humeral stem component.

According to another embodiment of the present invention there is provided a kit for use in performing total elbow arthroplasty. The kit includes an ulnar stem component for implantation at least partially in the ulnar medullary canal. The ulnar stem component defines a longitudinal axis thereof. The kit also includes a first ulnar hinge component attachable and removable from the ulnar stem component along the longitudinal axis of the ulnar stem component. The kit also includes a second ulnar hinge component attachable and removable from the ulnar stem component along the longitudinal axis of the ulnar stem component. The kit also includes a humeral stem component for implantation at least partially in the humeral medullary canal. The humeral stem component defining a longitudinal axis thereof. The kit also includes a humeral hinge component attachable to the humeral stem component and adapted for cooperation with at least one of the ulnar hinge components.

According to a further embodiment of the present invention, there is provided a method for providing total elbow arthroplasty. The method includes the steps of providing a elbow prosthesis kit including an ulnar stem component, an unconstrained ulnar hinge component, a semi-constrained ulnar hinge component, an humeral stem component, an unconstrained humeral hinge component, and a semi-constrained humeral hinge component; cutting an incision in the patient; observing the condition of the patients hard and soft tissue; determining the appropriateness of an unconstrained and a semi-constrained elbow prosthesis and selecting the appropriate components from an unconstrained ulnar hinge component, a semi-constrained ulnar hinge component, an unconstrained humeral hinge component, and a semi-constrained humeral hinge component; preparing the humeral cavity; assembling the chosen of an unconstrained humeral hinge component and a semi-constrained humeral hinge component onto the humeral stem component in the direction of the longitudinal axis of the humeral stem component; and implanting the humeral stem component in the humeral cavity.

According to another embodiment of the present invention, there is provided a method for providing total elbow revision arthroplasty. The method includes the steps of providing a elbow prosthesis kit including, a unconstrained ulnar hinge component, a semi-constrained ulnar hinge component, an unconstrained humeral hinge component, and a semi-constrained humeral hinge component; cutting an incision in the patient; observing the condition of the patients hard and soft tissue; determining the appropriateness of an unconstrained and a semi constrained elbow prosthesis and selecting the appropriate components from an unconstrained ulnar hinge component, a semi-constrained ulnar hinge component, an unconstrained humeral hinge component, and a semi-constrained humeral hinge component; and assembling the chosen of an unconstrained humeral hinge component and a semi-constrained humeral hinge component onto the humeral stem component in the direction of the longitudinal axis of the humeral stem component.

According to yet another embodiment of the present invention, there is provided an ulnar assembly for use with a humeral component to form an elbow prosthesis. The ulnar assembly includes a first component including a portion thereof defining a stem for implantation in a cavity formed in the ulna. The first component defines a longitudinal axis thereof generally coincident with the longitudinal axis of the ulna. The ulnar assembly also includes a second component attached to the first component. The second component is attachable and removable from the first component along the longitudinal axis of the first component. One of the first component and the second component include an external taper. The other of the first component and the second component defines an internal taper therein adapted to receive the external taper.

According to another embodiment of the present invention, there is provided an elbow prosthesis. The elbow prosthesis includes an ulnar component. The ulnar component includes a first portion thereof implantable in a cavity formed in the ulnar and a second portion. The second portion is operably connected to the first portion. The elbow prosthesis also includes a humeral component. The humeral component includes a first portion having a portion thereof defining a stem for implantation in a cavity formed in the humerus. The first portion defines a longitudinal axis thereof generally coincident with the longitudinal axis of the humerus and a second portion attached to the first portion. The second portion is attachable and removable from the first portion along the longitudinal axis of the first portion. One of the first portion and the second portion of the humeral component includes an external taper and the other of the first portion and the second portion of the humeral component defines an internal taper therein adapted to receive the external taper.

According to yet another embodiment of the present invention, there is provided a kit for use in performing total elbow arthroplasty. The kit includes an ulnar stem component for implantation at least partially in the ulnar medullary canal. The ulnar stem component defines a longitudinal axis thereof. The kit also includes a first ulnar hinge component attachable and removable from the ulnar stem component along the longitudinal axis of the ulnar stem component. The kit also includes a second ulnar hinge component attachable and removable from the ulnar stem component along the longitudinal axis of the ulnar stem component. The kit also includes a humeral stem component for implantation at least partially in the humeral medullary canal. The humeral stem component defines a longitudinal axis. The kit also includes a humeral hinge component attachable to the humeral stem component and adapted for cooperation with at least one of the ulnar hinge components.

The technical advantages of the present inventions include the ability to reduce condylar bone removal if the pin/poly axis is repaired. For example, according to one aspect of the present invention, a component for cooperation with another component to form a total elbow prosthesis is provided. The component includes a first portion including a portion defining a stem for implantation in a cavity formed in the long bone. The first portion defines a longitudinal axis thereof generally coincident with the longitudinal axis of the long bone. The component further includes a second portion attached to the first portion. The second portion is attachable and removable from the first portion along the longitudinal axis of the first portion. Thus, the present invention provides for the ability to provide for a reducing of condylar bone removal to replace the poly/pin axis. This benefit is accomplished by including the poly/pin axis on the second component and removing the second portion from the first portion before replacing the poly/pin axis thereby obviating the need for removing the bone around the poly/pin axis.

The technical advantages of the present invention further include the ability to fit the stem shape to the canal and to fit the head to the condylar area of the bone. For example, according to another aspect of the present invention, a long bone component for cooperation with another long bone component to form a total elbow prosthesis is provided. The first component includes a first portion including a part thereof defining a stem for implantation in the cavity formed in the long bone. The first portion defines a longitudinal axis thereof generally coincident with the longitudinal axis of the long bone. The first component further includes a second portion attached to the first portion. The second portion is attachable and removable from the first portion along the longitudinal axis of the first portion. Thus, the present invention provides for the ability to fit the stem shape to the canal and to fit the head portion to the condylar area. This benefit is possible because the first portion may be sized to fit the stem, while the second portion may be designed to conform to the condylar area of the bone.

The technical advantages of the present invention further include the ability to lower manufacturing costs and to provide for a less expensive tapered junction. For example, according to yet another aspect of the present invention, a component of a total elbow prosthesis is provided where the component includes a first portion and a second portion. One portion has an external tapered protrusion and the other portion including an internal tapered cavity adapted to receive the external tapered protrusion. The tapered connection is simple and inexpensive to manufacture. Thus the present invention provides for lower manufacturing costs and a less expensive junction.

The technical advantages of the present invention also include the ability to convert the prosthesis from an unconstrained configuration to a semi-constrained configuration without removal of the soft tissue or bone. For example, according to a further aspect of the present invention a first component for cooperation with a second component to form a total elbow prosthesis is provided. The first component includes a portion having a stem for implantation in a cavity formed in the humerus. The first component defines a longitudinal axis coincident with the longitudinal axis of the long bone. The first component further includes a second portion attached to the first portion. The second portion is attachable and removable from the first portion along the longitudinal axis of the first portion. Since the first and second portions of the component may be separated along the longitudinal axis of the long bone, the soft tissue and bone surrounding the medullary canal of the long bone need not be disturbed. Thus the present invention provides for the ability to convert the prosthesis with minimal the removal of soft tissue or bone.

The technical advantages of the present invention also include the ability to more closely fit the prosthetic features to individual patient anatomy, including: stem-size; bearing surfaces size; component location; and bearing mechanism. For example, according to another aspect of the present invention, a kit for use in performing total elbow arthroplasty is provided. The kit includes an ulnar stem, as well as a plurality of ulnar hinge components. The ulnar hinge components have different sizes and shapes to fit specific patients. By providing a plurality of ulnar hinge components, the present invention may provide for the various components to be sized to more closely fit the prosthetic features to individual patient anatomy.

The technical advantages of the present invention include the ability to be more dimensionally tolerant in the design of the prosthesis. For example, according to yet another aspect of the present invention, one component of a total elbow prosthesis is provided with an external tapered protrusion while the other component of the elbow prosthesis defines an internal tapered cavity adapted to receive the external tapered protrusion. Designing elbow prosthesis with separate modular junctions provides for the advantage that the accuracy in one junction will not affect the accuracy of the other junction. Therefore the joint pivot axis may not be affected by the accuracy of the mating tapered surfaces.

The technical advantages of the present invention yet include the ability to provide for optimal materials, coatings, and surface treatments for the elbow prosthesis. For example, according to yet another aspect of the present invention, a component for a total elbow prosthesis is provided with a first portion defining a longitudinal axis thereof as well as a second portion attachable and removable from the first portion along the longitudinal axis of the first portion. The first portion is adapted for implantation in the cavity formed in the long bone.

The surfaces of the first portion may include materials, coatings, and treatments to assist in the bony in-growth of the first portion to the long bone. By providing separable first portions and second portions of the total elbow prosthesis, the first portion and second portion may be made of different materials, have different coatings, or have different surface treatments. The selections can depend on, for example, whether the component is used for bony attachment to the long bone or for cooperation with another component of the elbow prosthesis.

The technical advantages of the present invention yet include the ability to permit easier surgical techniques such as those that may select type, size, and position of the articulating surfaces after cementing the stems. For example, according to yet another aspect of the present invention, a component that may be utilized for cooperation with a long bone to form a portion of a total elbow prosthesis is provided. The component includes a first portion for cooperation with the cavity formed in the long bone and a second portion attachable and removable from the first portion along the longitudinal axis of the first portion. Since the second portion may be inserted into the first portion along the longitudinal axis of the long bone, the first component may be cemented into position in the long bone prior to the installation of any other component thereby making the surgical technique easier.

The technical advantages of the present invention further include the ability to provide for a mobile bearing configuration of the elbow prosthesis. For example, according to yet another aspect of the present invention, a component is provided to be used to form a total elbow prosthesis. The component includes a first portion for cooperation with a long bone and a second portion attachable and removable from the first component along the longitudinal axis of the first component. The first component and second component may be configured to provide for rotatable motion therebetween. Thus the present invention provides for the ability to provide for a mobile bearing configuration for the prosthesis. Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
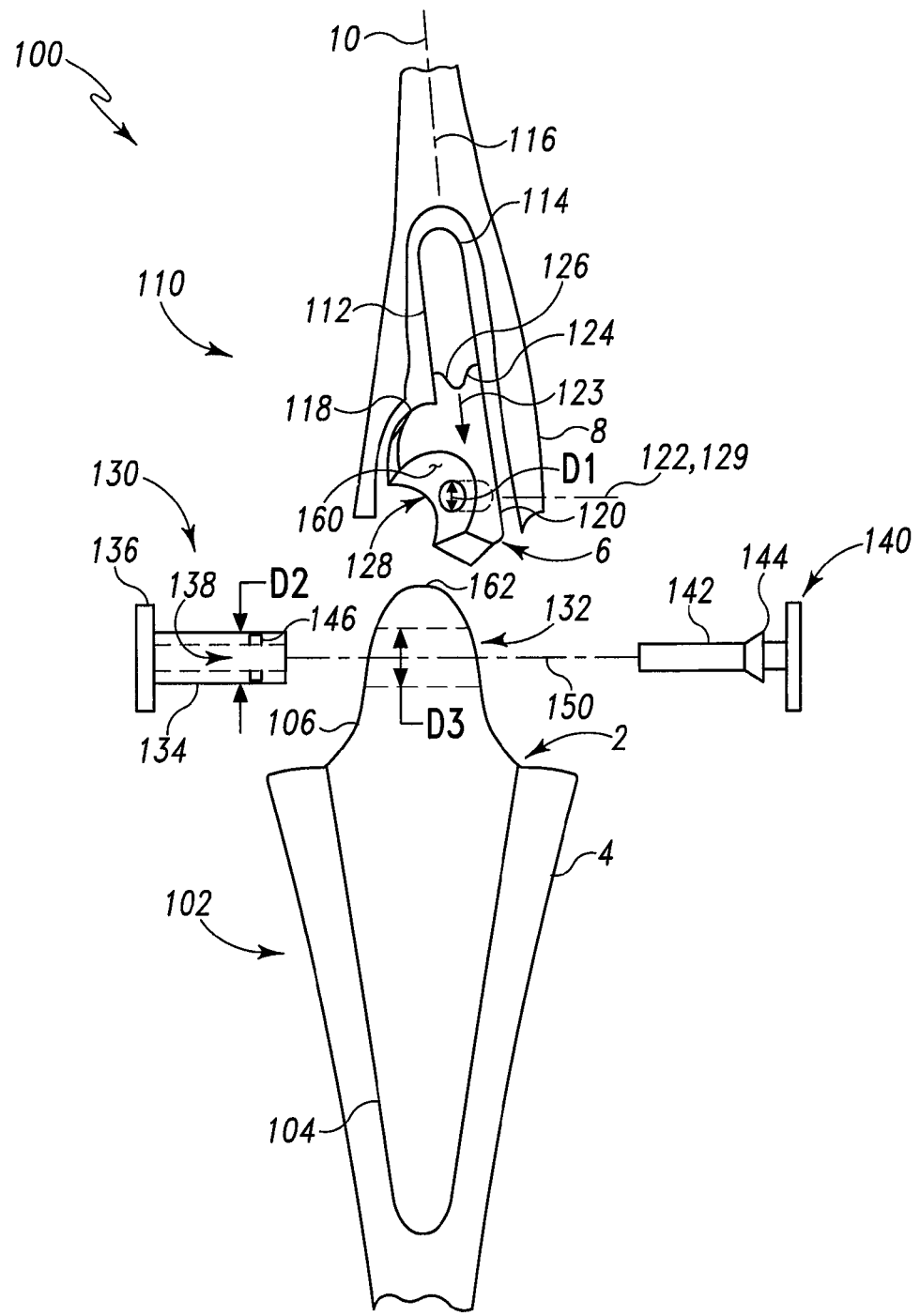
FIG. 1 is an anterior/posterior view partially in cross section of a first embodiment of the present invention of an elbow prosthesis assembly in position in a patient's arm including an elbow prosthesis assembly that has both unconstrained and semi-constrained configurations—shown in position implanted in a humerus—and an ulna with universal humeral and ulnar articulating components.

According to the present invention and referring now to FIG. 1, an elbow prosthesis 100 is shown. The elbow prosthesis 100 includes an ulnar component 102. The ulnar component 102 includes a first portion 104 of the ulnar component 102, which is implantable in a cavity 2 formed in the ulna 4. The ulnar component 102 further includes a second portion 106. The second portion 106 of the ulnar component 102 is connected to the first portion 104 of the ulnar component 102.

The elbow prosthesis 100 further includes a humeral component 110 including a first portion 112. The first portion 112 includes a part 114 of the first portion 112, which defines a stem for implantation in a cavity 6 formed in the humerus 8. The first portion 112 defines a longitudinal axis 116 of the first portion 112. The longitudinal axis 116 is generally coincident with the longitudinal axis 10 of the humerus 8. The humeral component 110 further includes a second portion 118 attached to the first portion 112. The second portion 118 is attachable and removable from the first portion 112 along the longitudinal axis 116 of the first portion 112 of the humeral component 110.

The elbow prosthesis 100 as shown in FIG. 1 may be configured such that the second portion 118 of the humeral component 110 includes a hinge portion 120. The hinge portion 120 defines a pivot axis 122 of the hinge portion 120.

As shown in FIG. 1, the second portion 118 of the humeral component 110 may be adapted to permit bone, for example a portion of the humerus 8, to remain on the humerus 8 after implantation of the prosthesis into the humerus.

The portion to remain may be that through the pivot axis 122. The ability of bone to remain on the humerus may be accomplished, referring to FIG. 1, by removing the second portion 118 from the first portion 112 of the humeral component 110 in the direction of arrow 123 along the longitudinal axis 116 of the first portion 112 of the humeral component 110 prior to the assembly of the ulnar component 102 onto the humeral component 110.

As shown in FIG. 1, the elbow prosthesis 100 may be configured such that the first portion 112 of the humeral component 110 may include an external tapered protrusion 124. The external tapered protrusion 124 may, for example, be conofrustrical. To cooperate with the first portion 112, the second portion 118 may include an internal tapered cavity 126 in the second portion 118. The internal tapered cavity 126 matingly receives the external tapered protrusion 124 of the first portion 112 of humeral component 110. It should be appreciated that, conversely, the second portion 118 may include an external taper (not shown) and the first portion 112 may include an internal taper (not shown) for receiving the external taper.

The elbow prosthesis 100 of FIG. 1 may be configured such that the second portion 118 of the humeral component 110 may define an opening 128 therein. The opening 128 as shown in FIG. 1 may be a through-opening. For example, the opening 128 may have a general cylindrical shape.

The opening 128 of the second portion 118 of the humeral component 110 may have a diameter, for example diameter D1, which is cooperable with diameter D2 of a pin 130. The opening 128 may further be cooperable with, for example opening 132, formed in ulnar component 102. The opening 132 may have a diameter D3 similar to diameter D1 of opening 128. The pin 130 may include a shank 134 having the diameter D2 for slidable fitting with the humeral opening 128 as well as with the ulnar opening 132.

The pin 130 as shown in FIG. 1, may include a head 136 located on an end of the shank 134 as well as an opening 138 extending from the opposed end of the shank 134. The opening 138 of the pin 130 may be utilized for receiving a cap 140, which is engagable with the pin 130 to provide a securable prosthesis joint. The cap 140 may include a stem 142 for receiving the shank 134. The stem 142 may include a protrusion 144 for cooperation with a groove 146 formed in the opening 138 of the shank 134 of the pin 130.

As can be seen in FIG. 1, when utilizing the pin 130 of the humeral component 110 and the ulnar component 102, the elbow prosthesis 100 may be of a semi-constrained type or form a semi-constrained prosthesis where the humeral component 110 and the ulnar component 102 pivot about humeral opening axis 129 and ulnar opening axis 150. It should be appreciated that when the pin 130 is installed in the humeral component 110 and the ulnar component 102, the humeral opening axis 129 and the ulnar component axis 150 are coincident.

Figure 1A:
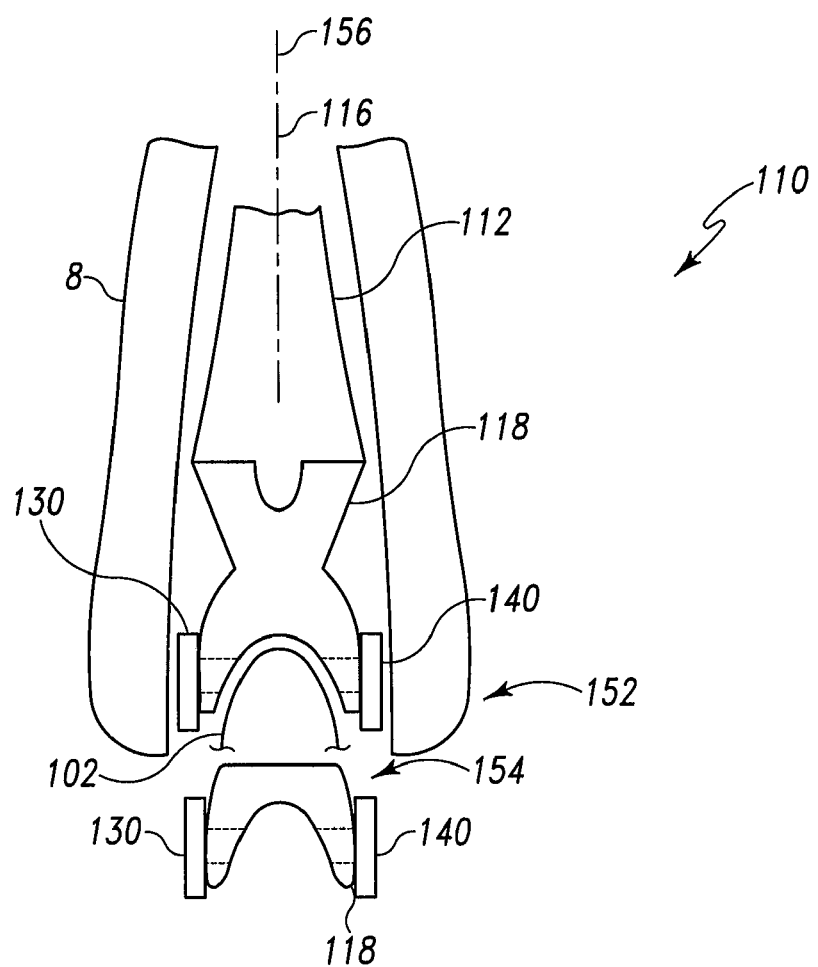
FIG. 1A is a partial plan view of the humeral portion of the elbow prosthesis of FIG. 1 showing the humeral articulating component in the implanted and assembly positions.

Referring now to FIG. 1A, the second portion 118 of the humeral component 110 is shown in first position 152 with ulnar component 102 engaged with humeral component 110.

According to the present invention and as shown in FIG. 1A, the second portion 118 of the humeral component 110 may be separated from the first portion 112 and removed along the longitudinal axis 116 of the first portion 112 in the direction of arrow 156 from first position 152 to second position 154 shown in phantom. It should be appreciated that the first portion 112 remains in position in the cavity 6 of the humerus 8 while the second portion 118 of the humeral component 110 advances in the direction of arrow 156. In second portion 154 the pin 130 as well as the cap 140 may extend beyond the humerus 8 so that the cap 140 and the pin 130 may be removed from the second portion 118, of the humeral component 110 as well as from the ulnar component 102 without disturbing the bone, for example, the humerus 8 or adjacent soft tissue.

For example and referring again to FIG. 1, the elbow prosthesis 100 may be configured such that the second portion 118 of the humeral component 110 may include a contact surface 160 adapted for cooperation with the ulnar component 102. The second portion 118 may, as shown in FIG. 1, be adapted to be freely separated from the ulnar component 102 in a direction normal or perpendicular to the contact surface 160.

As shown in FIG. 1, the contact surface 160 of the second portion 118 of the humeral component 110 may be generally concave. This configuration is considered a reverse configuration as it is reversed to an anatomical humeral elbow component that is convex. It should be appreciated that conversely the contact surface 160 of the second portion 118 of the humeral component 110 may be convex.

The elbow prosthesis 100 of FIG. 1 may, as shown in FIG. 1, be used both as a semi-constrained prosthesis as well as an unconstrained prosthesis. As shown in FIG. 1, when utilizing the pin 130 the elbow prosthesis 100 is used as a semi-constrained prosthesis.

For an unconstrained prosthesis, the pin 130 is not used. The contact surface 160 of the second portion 118 of the humeral component 110 then may engage with contact surface 162 of the ulnar component 102. The contact surfaces 160 and 162 provide for articulation between the humeral component 110 and the ulnar component 102 but yet permit separation of the humeral component 110 from the ulnar component 102 in a direction normal to the contact surfaces 160 and 162.

Figure 2:
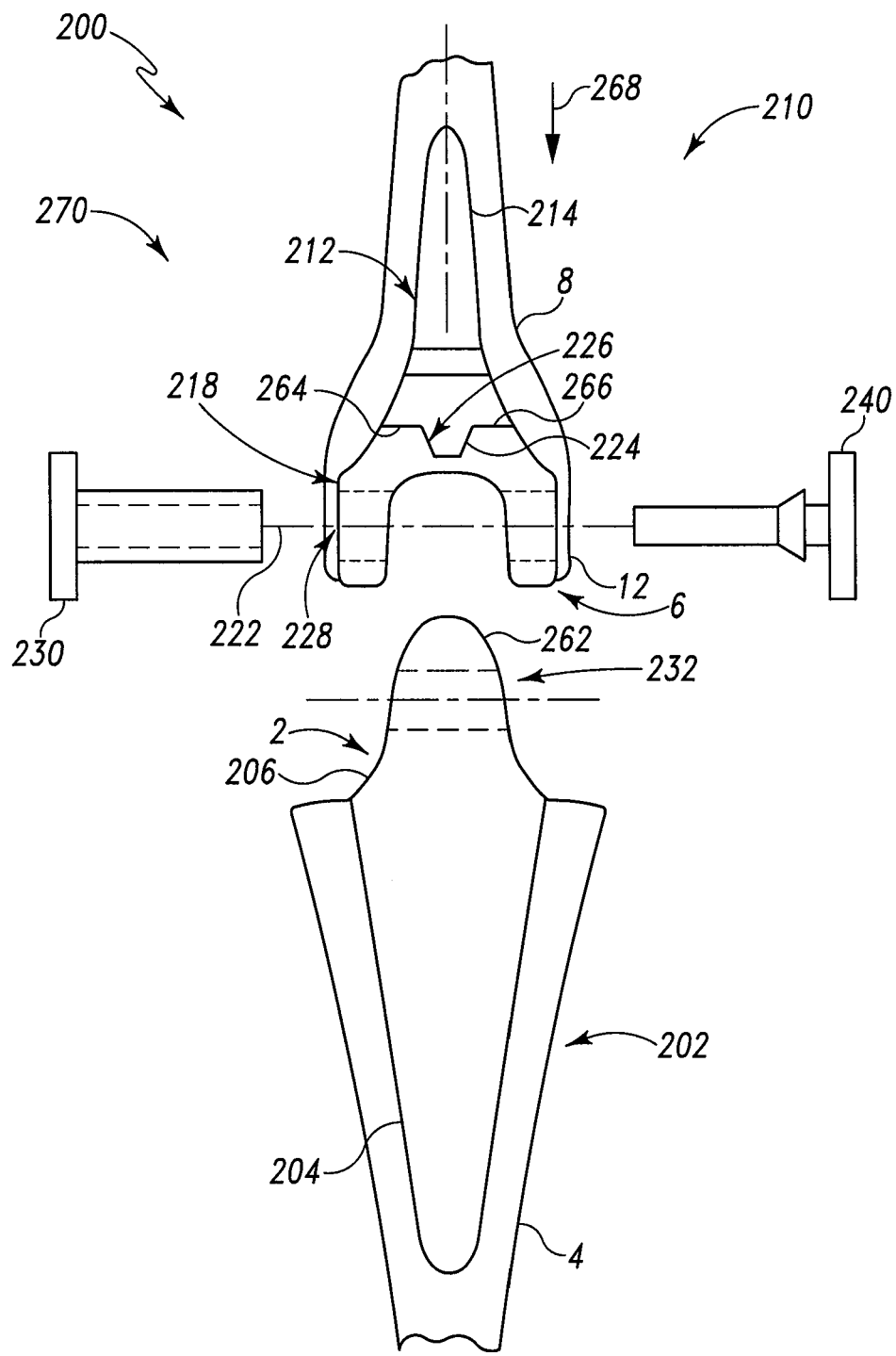
FIG. 2 is an anterior/posterior view partially in cross section of another embodiment of an elbow prosthesis according to the present invention showing a semi-constrained/unconstrained elbow prosthesis assembly shown in position implanted in a humerus and an ulna with separate humeral articulating components for constrained and unconstrained configurations.

Referring now to FIG. 2, yet another embodiment of the present invention is shown as total elbow prosthesis 200. The total elbow prosthesis 200 includes an ulnar component 202 for cooperation with the ulna 4 as well as a semi-constrained humeral assembly 210 for implantation into the humerus 8 and for cooperation with the ulnar component 202. Unlike the total elbow prosthesis 100 of FIG. 1, the total elbow prosthesis 200 of FIG. 2 requires the use of a different component on the humeral side of the total elbow prosthesis 200 to convert from an unconstrained total elbow prosthesis to an semi-constrained total elbow prosthesis.

The ulnar component 202 of the total elbow prosthesis 200 of FIG. 2 is similar to the ulnar component 102 of the elbow prosthesis 100 of FIG. 1. The ulnar component 202 of FIG. 2 includes the stem portion 204, which cooperates with cavity 2 of the ulna 4. An articulating portion 206 extends from the stem portion 204 of the ulnar component 202. An ulnar articulating surface 262 is formed on the surface of the articulating portion 206 of ulnar component 202.

The ulnar component 202 also includes an ulnar opening 232 formed in the articulating portion 206 of the ulnar component 202. The ulnar component 202 and the unconstrained humeral assembly 210 may be made of any suitable, durable material and may for example be made of a metal. If made of a metal the ulnar component 202 and humeral assembly 210 may be made of, for example, a cobalt chromium alloy, a stainless steel alloy, or a titanium alloy.

Unlike the humeral component 110 of the elbow prosthesis 100 of FIG. 1, the semi-constrained humeral assembly 210 of the total elbow prosthesis 200 is suitable for use only in the semi-constrained version of the total elbow prosthesis. The semi-constrained humeral assembly 210 includes a humeral stem component 212, which is-matingly fitted to the cavity 6 of the humerus 8. The humeral stem component 212 includes a portion 214 defining a stem. The stem 214 closely conforms to the medullary canal of the humerus 8. The semi-constrained humeral assembly 210 further includes a semi-constrained humeral articulating component 218 which mates with the humeral stem component 212 to form the semi-constrained humeral assembly 210.

The semi-constrained humeral articulating component 218 may be secured to the humeral stem component 212 in any suitable fashion and may, as shown in FIG. 2, be connected by a tapered connection. For example, and as shown in FIG. 2, the humeral stem component 212 may include an exterior tapered protrusion 224 which mates with an interior tapered cavity 226 formed in the constrained humeral articulating component 218.

The humeral stem component 212 may include support surface 264, which mates with a support surface 266 located on the semi-constrained humeral articulating component 218. The surfaces 264 and 266 serve to provide for an improved positioning of axis 222 of humeral opening 228 formed in the semi-constrained humeral articulating component 218. The position and condition of the surfaces 264 and 266 are more easy to control and obtain accurate dimensions than the internal tapered cavity 226 and the external tapered protrusion 224.

The semi-constrained humeral articulating component 228 may be removed from the humeral stem component 222 by moving the semi-constrained humeral articulating component in the direction of arrow 268. When moving the semi-constrained humeral articulating component 218 in the direction of arrow 268, condylar portions 12 of the humerus 8 remain intact and do not need to be removed to accommodate the removal or disassembly of the semi-constrained humeral articulating component 218 from the semi-constrained humeral assembly 210.

The semi-constrained humeral assembly 210 is connected to the ulnar component 202 to form constrained total elbow prosthesis 270 by inserting pin 230 into the humeral opening 228 as well as into the ulnar opening 232.

A cap 240 may cooperate with pin 230 to secure the pin 230 into position.

Figure 2A:
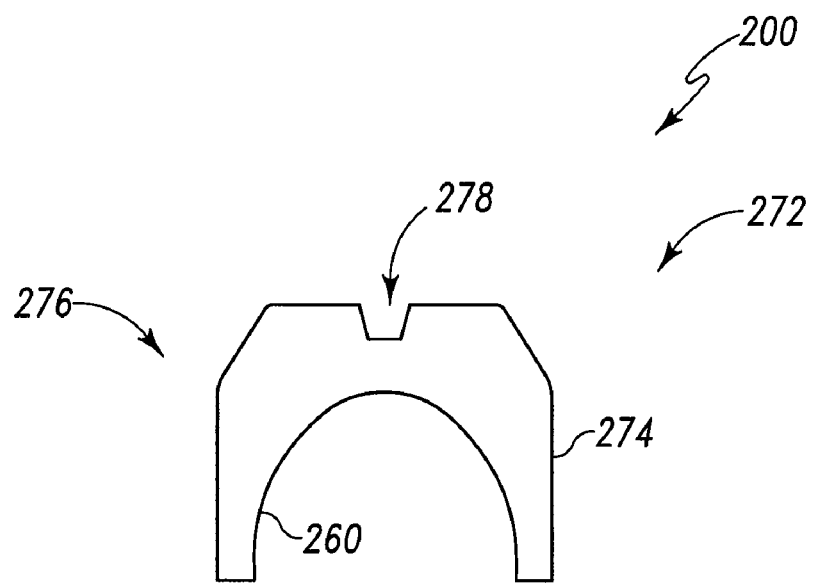
FIG. 2A is a plan view partially in cross section of an unconstrained humeral component for use with the elbow prosthesis of FIG. 2.

Referring now to FIG. 2A, the total elbow prosthesis 200 may also be utilized for an unconstrained elbow prosthesis 272. The unconstrained prosthesis 272 includes, the ulnar component 202 as well as humeral stem component 212 see FIG. 2.

Referring now to FIGS. 2 and 2A to form the unconstrained elbow prosthesis 272 the semi-constrained humeral articulating component 218 is removed from the humeral stem component 212 and humeral unconstrained articulating component 274 is positioned on humeral stem component 212 to form unconstrained humeral assembly 276. The humeral unconstrained articulating component 274 preferably includes an internal tapered cavity 278 which has dimensions similar to the internal tapered cavity 226 of the semi-constrained humeral articulating component 218 in order that the semi-constrained component 218 and the unconstrained component 274 may be interchanged on the humeral stem component 212.

The humeral unconstrained articulating component 274 may include a humeral articulating surface 260 which mates with the ulnar articulating surface 262 to form the unconstrained elbow prosthesis 272. The humeral articulating surface 260 is concave which like that of the prosthesis 100 of FIG. 1 is a reverse configuration.

Figure 3:
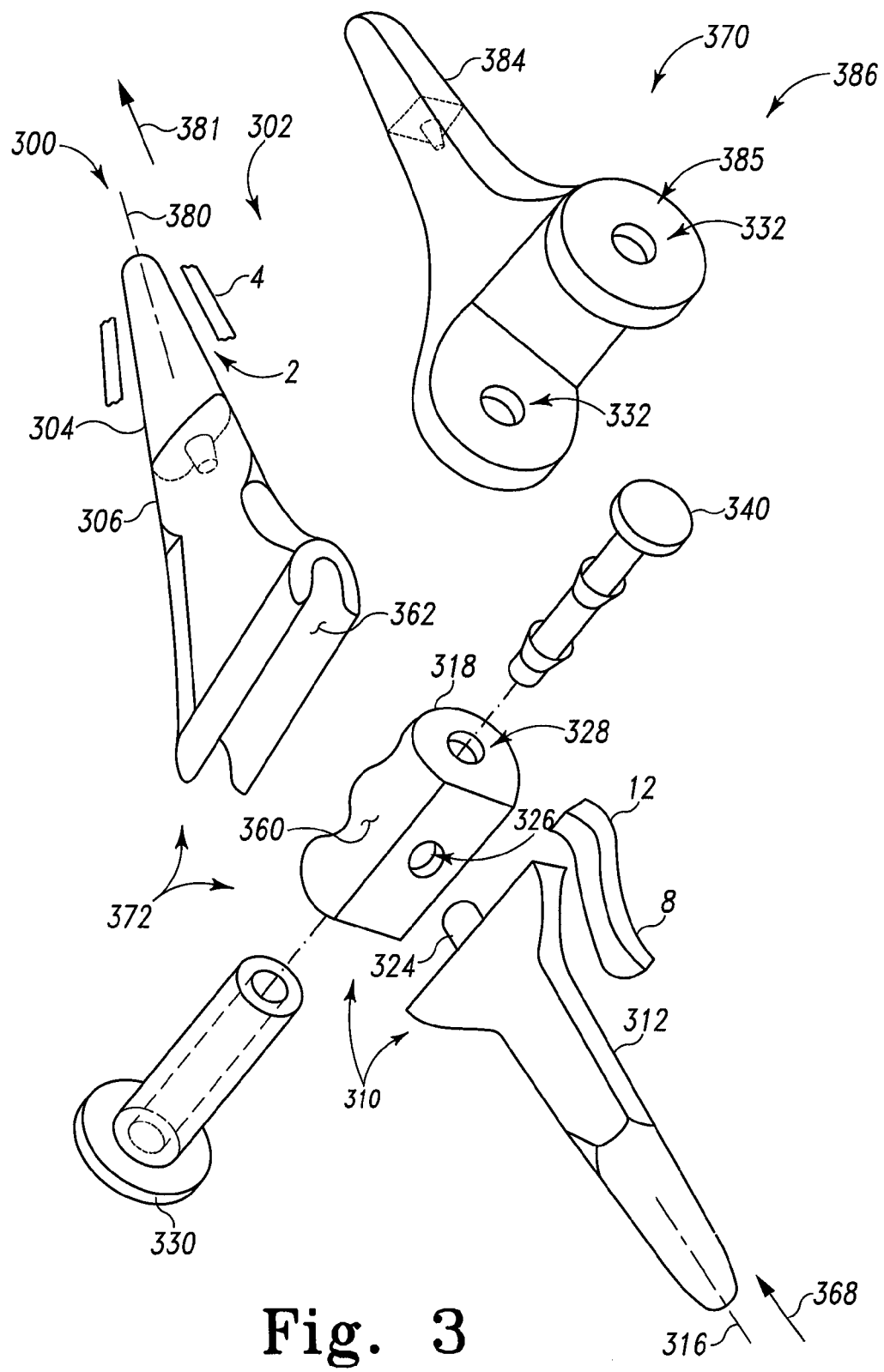
FIG. 3 is an exploded perspective view of another embodiment of the present invention in the form of an elbow prosthesis assembly in position in a patient's arm including an unconstrained elbow prosthesis assembly shown in position implanted in a humerus and an ulna.

Referring now to FIG. 3, yet another embodiment of the present invention is shown as total elbow prosthesis 300. The total elbow prosthesis 300, is similar to the total elbow prosthesis 100 of FIG. 1 as well as to the total elbow prosthesis 200 of FIG. 2. The total elbow prosthesis 300, however, is not in the form of a reverse prosthesis. In other words, the total elbow prosthesis 300 includes an unconstrained version in which the articulating surfaces of the total elbow prosthesis 300 are normal or anatomical. In other words, compared to prosthesis 100, in prosthesis 300 the convex surface becomes concave and the concave surface becomes convex.

The total elbow prosthesis 300 of FIGS. 3 through 8 also are different than the total elbow prosthesis 100 and 200 of FIGS. 1 and 2, respectively in that the total elbow prosthesis 300 of FIGS. 3 through 8 include humeral components that may be used both in the semi-constrained and unconstrained embodiments of the total elbow prosthesis and the ulnar components of the total elbow prosthesis 300 are different depending on the use of an unconstrained elbow prosthesis or a semi-constrained elbow prosthesis.

Continuing to refer now to FIG. 3, the total elbow prosthesis 300 includes a humeral assembly 310 that may be used for both unconstrained and semi-constrained embodiments of the total elbow prosthesis 300. For example, as shown in FIG. 3, the first humeral assembly 310 includes a humeral stem 312. A humeral articulating component 318 is removably connected to the humeral stem 312 along humeral stem axis 316.

While the humeral articulating component 318 may be removably connected to the humeral stem 312 in any suitable manner, for example and as shown in FIG. 3, the humeral articulating component 318 includes an internal taper cavity 326 which mates with an exterior tapered protrusion 324.

In order that the humeral articulating component 318 of the humeral assembly 310 can be used for both a semi-constrained and an unconstrained elbow prosthesis, the humeral articulating component 318 includes both an exterior articulating surface 360 for use in the unconstrained version as well as a humeral opening 328 for cooperation with a pin 330 and a cap 340. The opening 328 is for use in the semi-constrained versions of the total elbow prosthesis 300.

In the total elbow prosthesis 300 of FIGS. 3 through 8, unlike the prosthesis 100 and 200 of FIGS. 1 and 2 respectively, the total elbow prosthesis 300 may include a modular or two piece ulnar assembly. For example and as shown in FIGS. 3, the total elbow prosthesis 300 may include an unconstrained ulnar two-piece component 302. The unconstrained ulnar component 302 includes an ulnar stem portion 304 for cooperation with cavity 2 of ulna 4.

The humeral stem component 312 of the humeral assembly 310 may be assembled and disassembled from the humeral articulating component 318 by advancing the humeral articulating component 318 in the direction of arrow 368 along longitudinal axis 316 of the humeral stem 312. The humeral articulating component 318 may be disassembled from the humeral stem 312 with the pin 330 and the cap 340 in position on the humeral articulating component 318 so that the condylar portion 112 of the humerus 8 may not be disturbed.

According to the present invention and referring now again to FIG. 3, the total elbow prosthesis 300 includes a semi-constrained ulnar component 386. The semi-constrained ulnar component 386 includes an ulnar stem 384. The ulnar stem 384 is matingly fitted into the cavity 2 of the ulna 4. The semi-constrained ulnar assembly 302 further includes a semi-constrained ulnar-articulating portion 385, which defines ulnar-opening 332.

A semi-constrained elbow prosthesis 370 of the total elbow prosthesis 300 includes the semi-constrained ulnar component 386 which mates with humeral assembly 310 to form semi-constrained elbow assembly 370. The semi-constrained elbow assembly 370 further includes the humeral assembly 310 as well as the pin 330 and the cap 340.

The unconstrained ulnar stem component 302 defines a longitudinal axis 380. The unconstrained ulnar component 306 is removable from the humeral articulating component 318 in the direction of arrow 381 along axis 380. Unconstrained articulating ulnar component 306 defines an ulnar articulating surface 362 which may have a combination of ridges to match the profile of surface 360 and may be in slidable contact with articulating surface 360 of the humeral articulating component 318 to form unconstrained elbow prosthesis 372.

The total elbow prosthesis 300 provides for both semi-constrained elbow prosthesis 370 as well as unconstrained elbow prosthesis 372. The unconstrained elbow prosthesis 372 includes the unconstrained ulnar component 302 as well as the humeral assembly 310.

Figure 4:
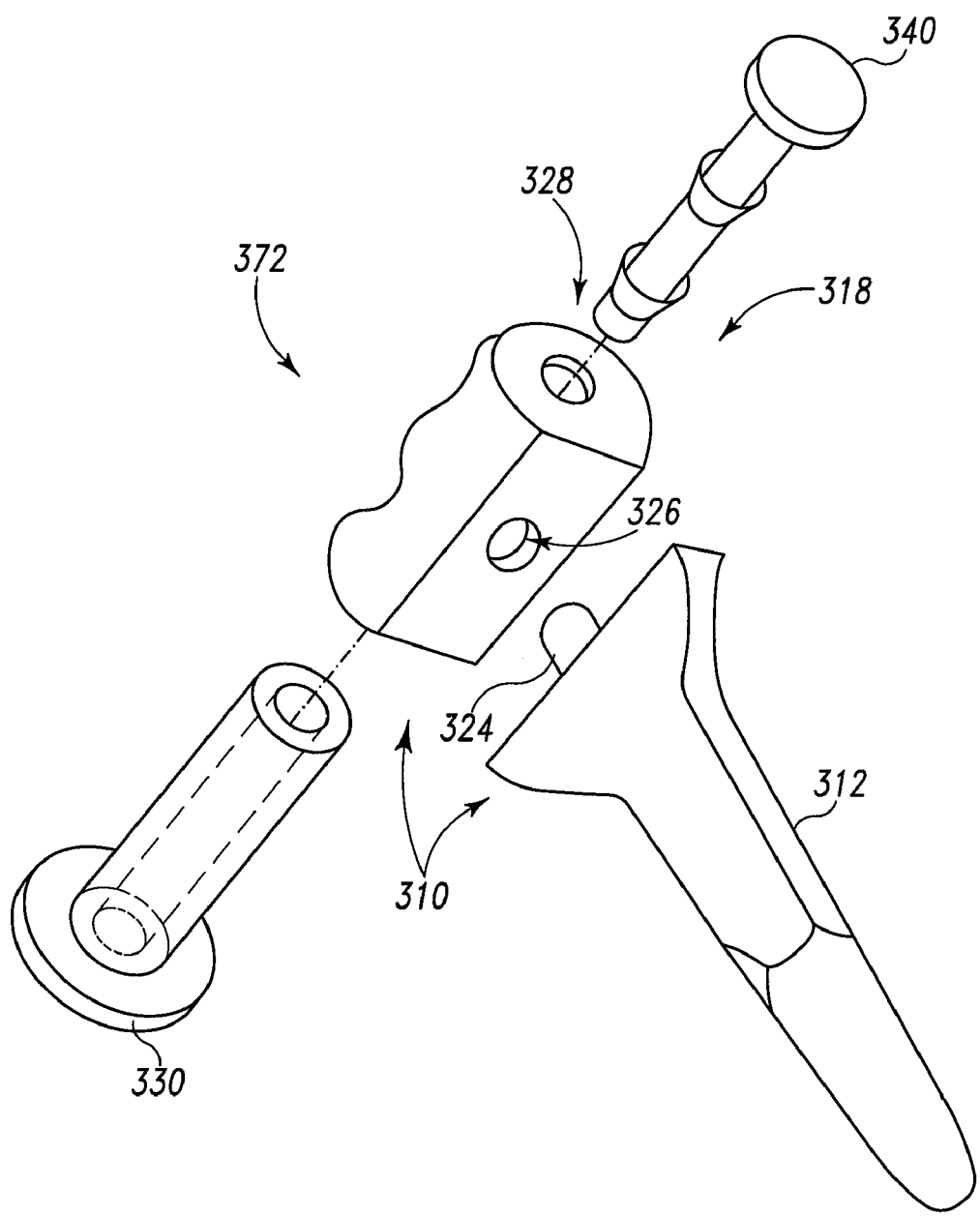
FIG. 4 is an exploded perspective view of the humeral assembly of the elbow prosthesis assembly of FIG. 3.

Referring now to FIG. 4, the humeral assembly 310 for use with the semi-constrained elbow prosthesis 370 and of the unconstrained elbow prosthesis 372 is shown in greater detail. The humeral assembly 310 includes the humeral stem 312 as well as the humeral articulating component 318. The unconstrained elbow prosthesis 372 utilizes the humeral assembly 310 including the stem component 312 as well as the articulating component 318. The pin 330 and the cap 340 are utilized with semi-constrained humeral prosthesis 370.

Figure 5:
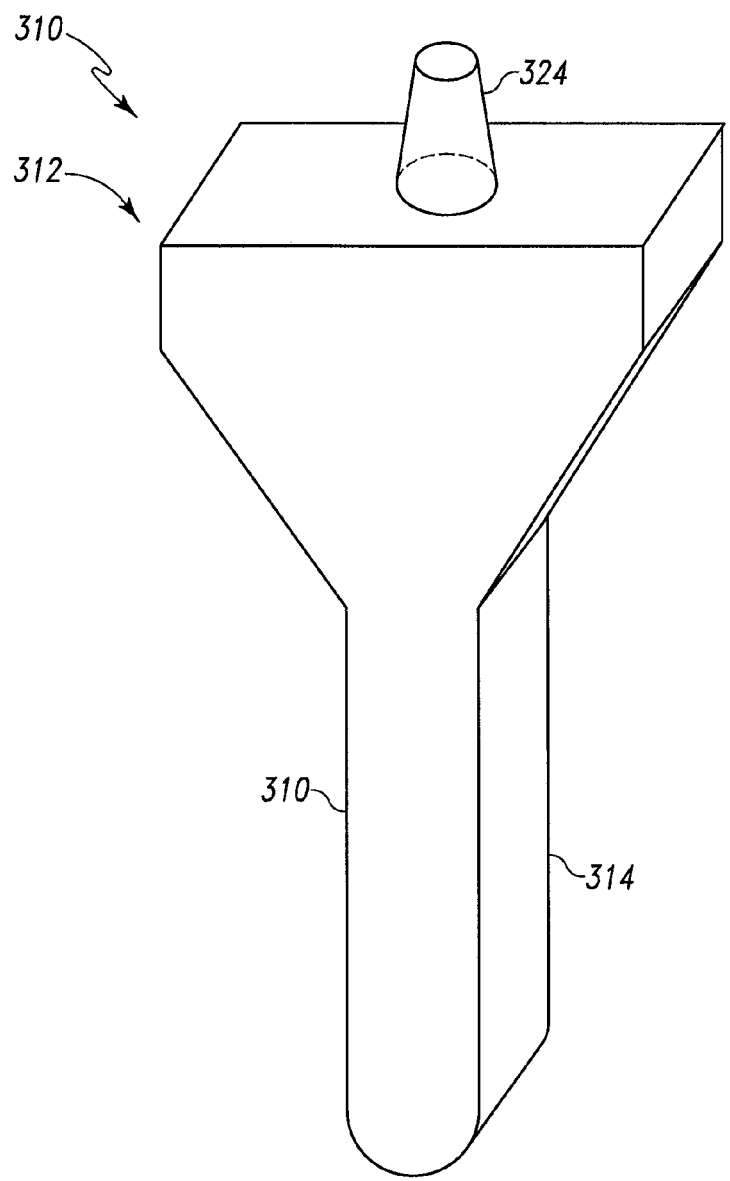
FIG. 5 is a perspective view of the humeral stem of the humeral assembly of the elbow prosthesis assembly of FIG. 3.

Referring now to FIG. 5, the humeral stem component 312 is shown in greater detail. The humeral stem component 312 includes a portion 314 defining a stem. The stem component 312 also includes the external tapered protrusion 324.

Figure 6:
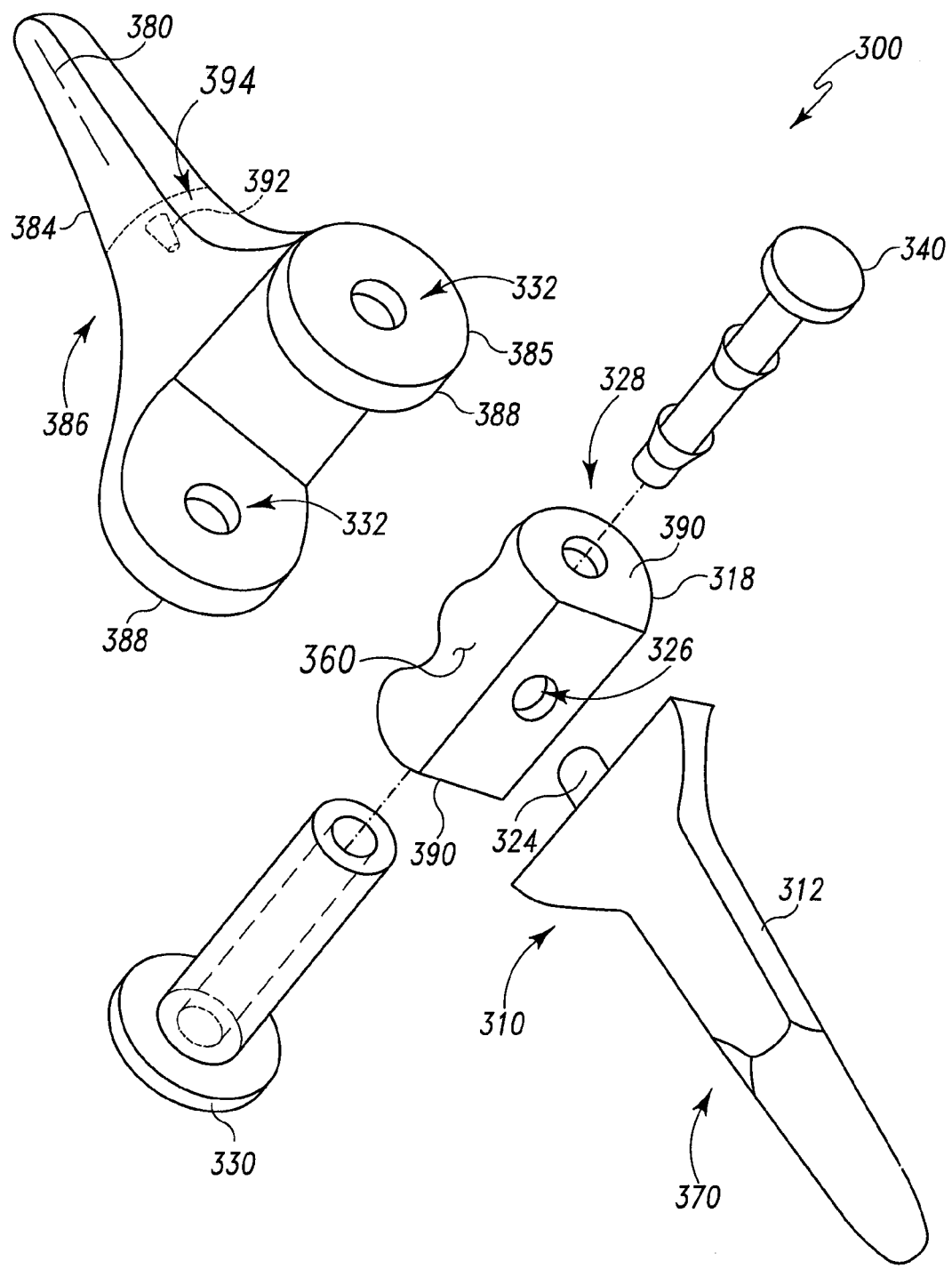
FIG. 6 is an exploded perspective view of the semi-constrained elbow prosthesis assembly version of the elbow prosthesis assembly of FIG. 3.

Referring now to FIG. 6, semi-constrained elbow prosthesis 370 is shown in greater detail. The semi-constrained elbow prosthesis 370 includes the humeral stem 312 as well as the humeral articulating component 318, which form the humeral assembly 310. The semi-constrained elbow prosthesis 370 further includes the semi-constrained ulnar component 386. The semi-constrained ulnar component 386 includes the ulnar stem portion 384 as well as the ulnar articulating portion 385.

The ulnar articulating portion 385 includes a pair of spaced apart protrusions 388 which are adapted to be positioned over ends 390 of the humeral articulating component 318. The ulnar articulating portion 385 includes a pair of spaced apart ulnar openings 332 located in the protrusions 388. The humeral opening 328 and the ulnar openings 332 serve to receive the pin 330 and the cap 340 to provide for the semi-constrained elbow prosthesis 370.

The ulnar stem portion 384 and articulating portion 385 may be integral with each other. Alternatively, the ulnar stem portion 384 and ulnar articulating portion 385 may be separate components removably secured to each other in any suitable fashion. For example and as shown in FIG. 6, the ulnar stem portion 384 may include an external tapered protrusion 392 which is positioned along longitudinal axis 380 of the ulnar stem component 304. The ulnar articulating portion 385 may define an ulnar internal tapered cavity 394 for matingly receiving the external tapered protrusion 392 of the ulnar stem portion 384.

Figure 7:
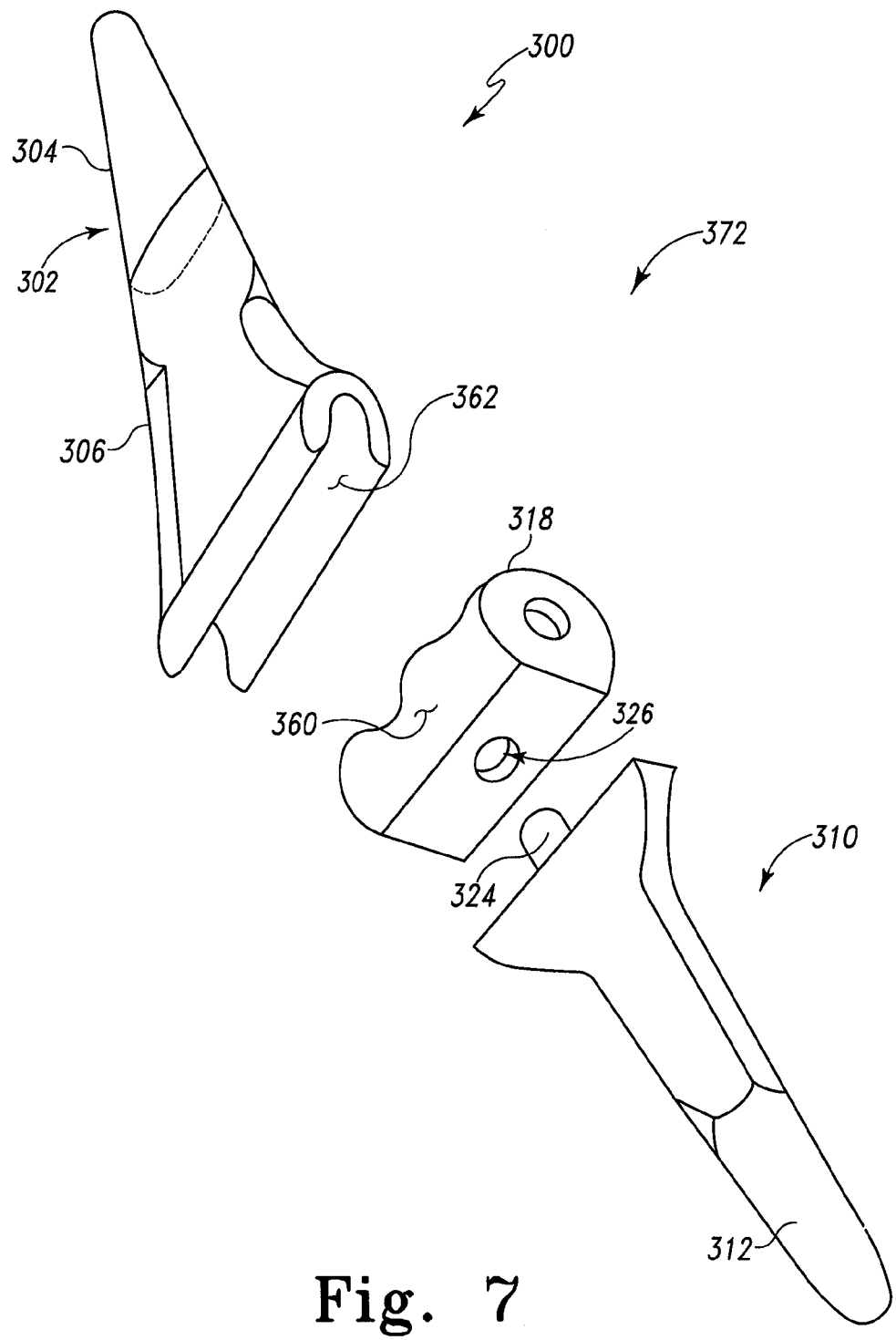
FIG. 7 is an exploded perspective view of the humeral assembly of the unconstrained version of the elbow prosthesis assembly of FIG. 6.

Referring now to FIG. 7, the unconstrained elbow prosthesis of the total elbow prosthesis 300 of FIG. 7 is shown. The unconstrained elbow prosthesis 372 includes the humeral assembly 310, which mates with the ulnar assembly 302. The humeral assembly 310 includes the humeral stem component 312 and the humeral articulating component 318. The ulnar assembly 302 includes the ulnar stem portion 304 and the ulnar unconstrained articulating portion 306. The ulnar stem portion 306 of the ulnar stem portion 384 may be identical.

The ulnar unconstrained articulating portion 306 includes the ulnar articulating surface 362 which mates with the humeral articulating surface 360 of the humeral articulating component 318 of the humeral assembly 310.

It should be appreciated that the ulnar articulating component 362 is concave and the humeral articulating component 360 is convex. It should be appreciated that the humeral articulating surface 360 may be concave and the ulnar articulating component 362 be convex.

Figure 8:
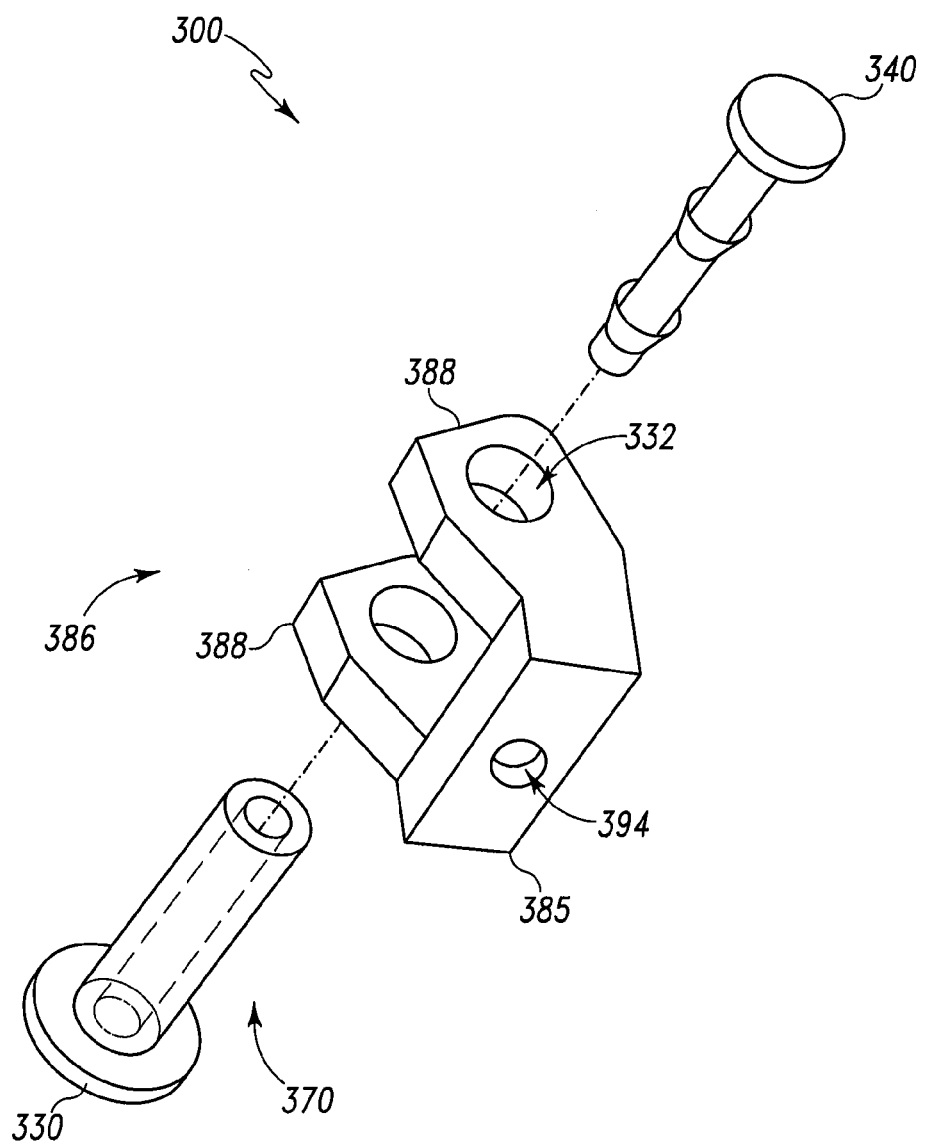
FIG. 8 is an exploded perspective view of the humeral body assembly of the humeral assembly of the elbow prosthesis assembly of FIG. 6.

Referring now to FIG. 8, the ulnar semi-constrained articulating portion 385 of the semi-constrained ulnar component 386 of the semi-constrained elbow assembly 370 is shown in greater detail. Semi-constrained ulnar articulating portion 385 includes the ulnar opening 332, which is sized for receiving the pin 330. The cap 340 engages the pin 330 to secure the humeral articulating component 318 (see FIG. 6).

Referring now to FIGS. 9-23, yet another embodiment of the present invention is shown as total elbow prosthesis 400. The total elbow prosthesis 400 includes both an unconstrained version in the form of unconstrained elbow prosthesis 472 of FIG. 9 and a semi-constrained elbow prosthesis 470 as shown in FIG. 20.

Referring again to FIG. 9, the unconstrained elbow prosthesis 472 of the present invention is shown. The unconstrained elbow prosthesis 472 includes an unconstrained ulnar assembly 402, which cooperates with an unconstrained humeral assembly 410.

The unconstrained ulnar assembly 402 includes an ulnar stem component 404, which defines an ulnar stem centerline 480. An ulnar unconstrained articulating component 406 is slidably connectable to the ulnar stem component 404 along ulnar stem centerline 480. The ulnar unconstrained articulating component 406 defines an ulnar articulating surface 462.

Figure 9:
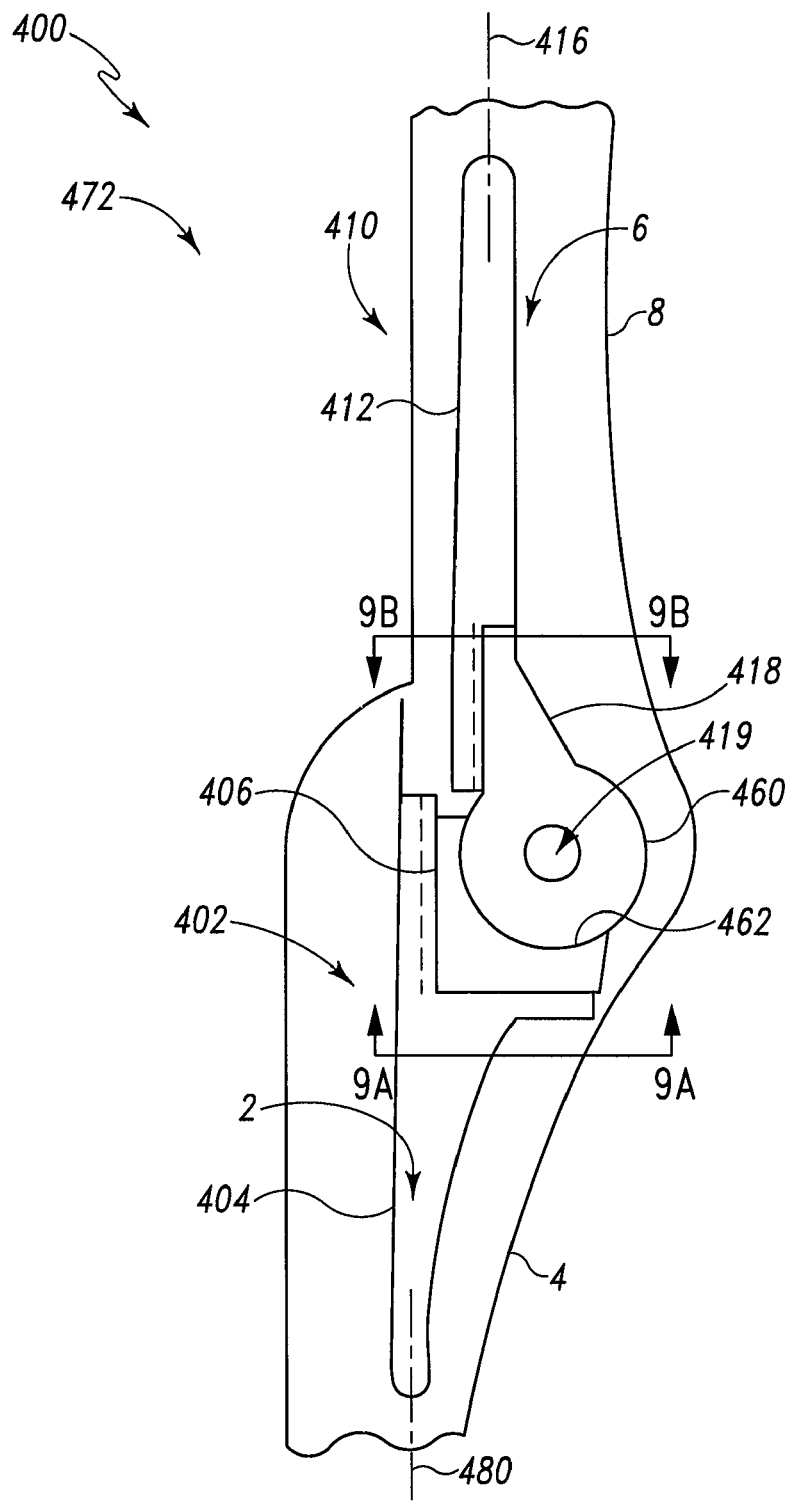
FIG. 9 is an anterior/posterior view partially in cross section of yet another embodiment of the present invention in the form of an elbow prosthesis assembly in position in a patient's arm including an unconstrained elbow prosthesis assembly shown in position implanted in a humerus and an ulna.
Figure 9A:
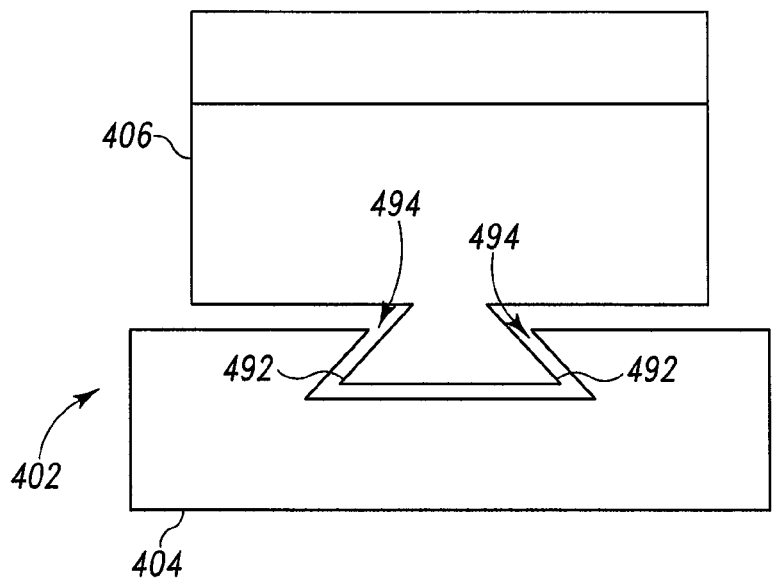
FIG. 9A is a cross sectional view of FIG. 9 along the line 9A-9A in the direction of the arrows.

Referring now to FIG. 9A, the ulnar stem component 404 and the ulnar unconstrained articulating component 406 are joined in a different manner than the total elbow prosthesis 100, 200, or 300.

For example and as shown in FIG. 9A, the unconstrained ulnar assembly 402 has a different connecting mechanism than that of the total elbow prosthesis 100, 200, or 300. For example and as shown in FIG. 9A, the unconstrained ulnar articulating component 406 includes a pair of spaced apart protrusions 492 which cooperate with a pair of spaced-apart voids 494 formed in the ulnar stem component 404. For example and as shown in FIG. 9A, the protrusions 492 form a dovetail connection.

Referring again to FIG. 9, the unconstrained elbow prosthesis 472 further includes the unconstrained humeral assembly 410. The unconstrained humeral assembly 410 includes a humeral stem component 412, which defines a humeral stem centerline 416. The humeral stem component 412 is fitted into cavity 6 of the humerus 8.

The unconstrained humeral assembly 410 further includes an unconstrained humeral articulating component 418, which is removably connected to the humeral stem component 412 along humeral stem centerline 416. The unconstrained humeral articulating component 418 defines a humeral articulating surface 460 which is in mating cooperation, for example rolling and/or sliding contact, with the ulnar articulating surface 462 of the ulnar unconstrained articulating component 406.

As shown in FIG. 9, the humeral articulating surface 460 is convex while the ulnar articulating surface 462 is concave. It should be appreciated that the unconstrained elbow prosthesis 472 may be designed such that the ulnar articulating surface is convex and the humeral articulating surface is concave.

Figure 9B:
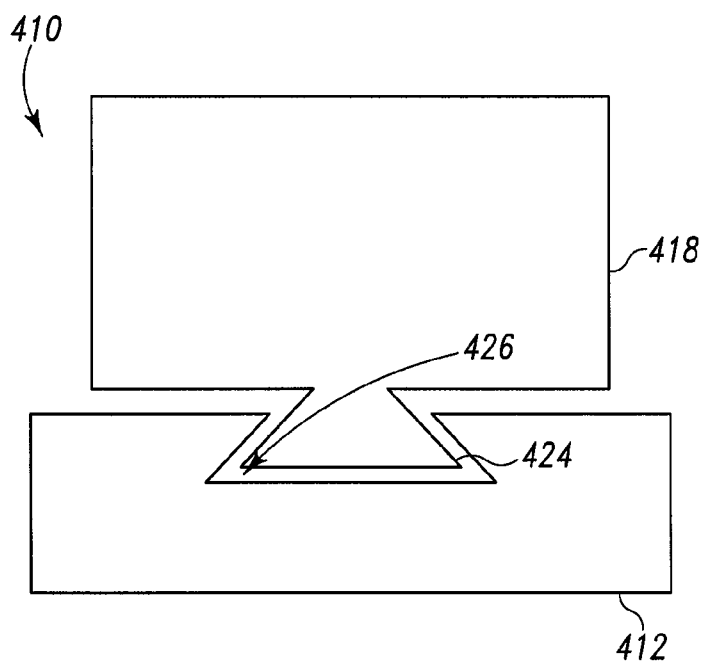
FIG. 9B is a cross sectional view of FIG. 9 along the line 9B-9B in the direction of the arrows.

Referring now to FIG. 9B, the unconstrained humeral articulating component 418 may be slidably fitted to the humeral stem component 412 in any suitable manner. Preferably, and as shown in FIG. 9B, the constrained humeral articulating component 418 includes a pair of spaced apart protrusions 424 which mate with voids 426 formed in the humeral stem component 412. The protrusions 424 of the unconstrained humeral articulating component 418 may be in the form as shown in FIG. 9B of a dovetail connection.

Referring again to FIG. 9, the unconstrained humeral articulating component 418 may include a humeral opening 419 as shown in phantom. The opening 419 may be utilized to provide the use of the unconstrained humeral articulating component 418 in a semi-constrained version of the total elbow prosthesis 400.

Figure 10:
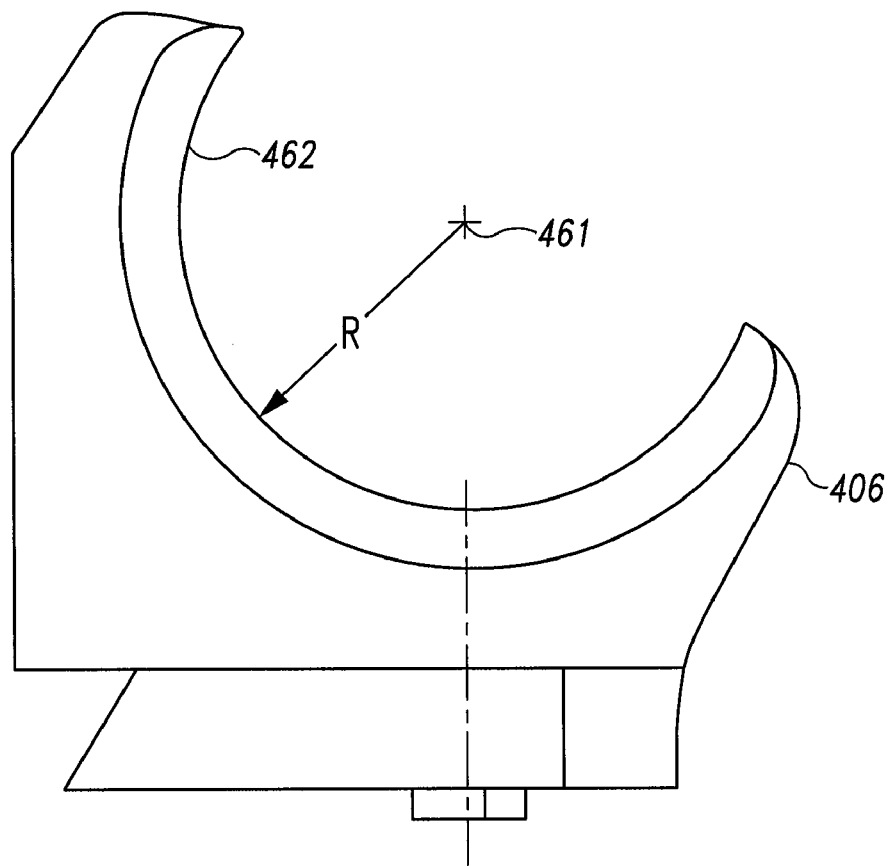
FIG. 10 is a plan view of the articulating portion of the unconstrained ulnar component of the unconstrained elbow prosthesis assembly of FIG. 9.
Figure 11:
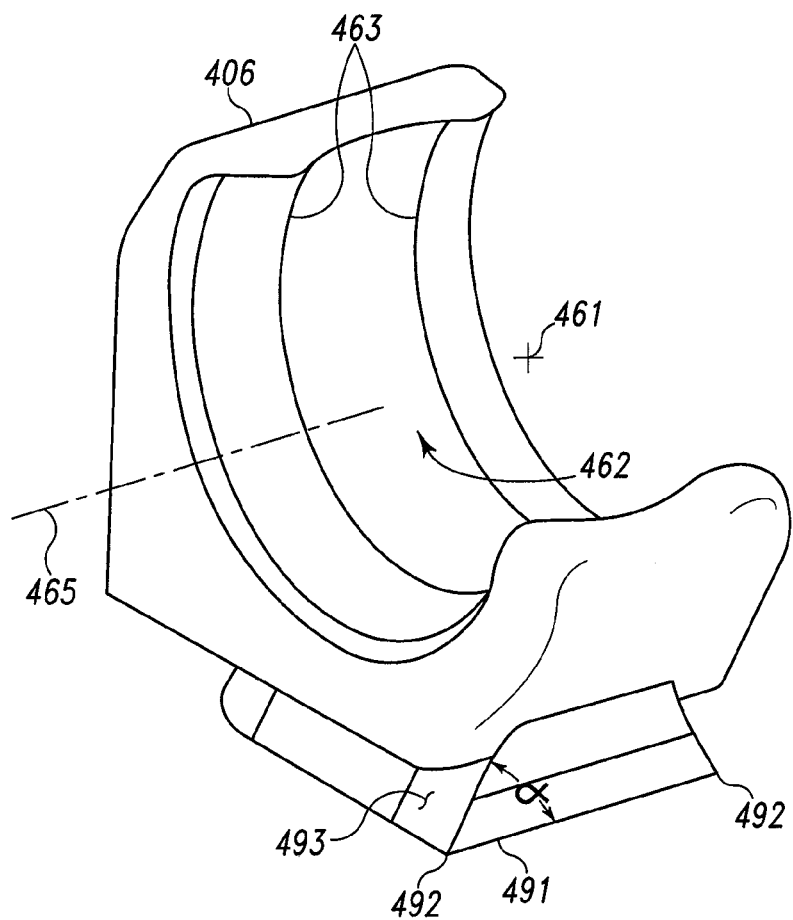
FIG. 11 is a perspective view of the unconstrained ulnar component of FIG. 10.
Figure 12:
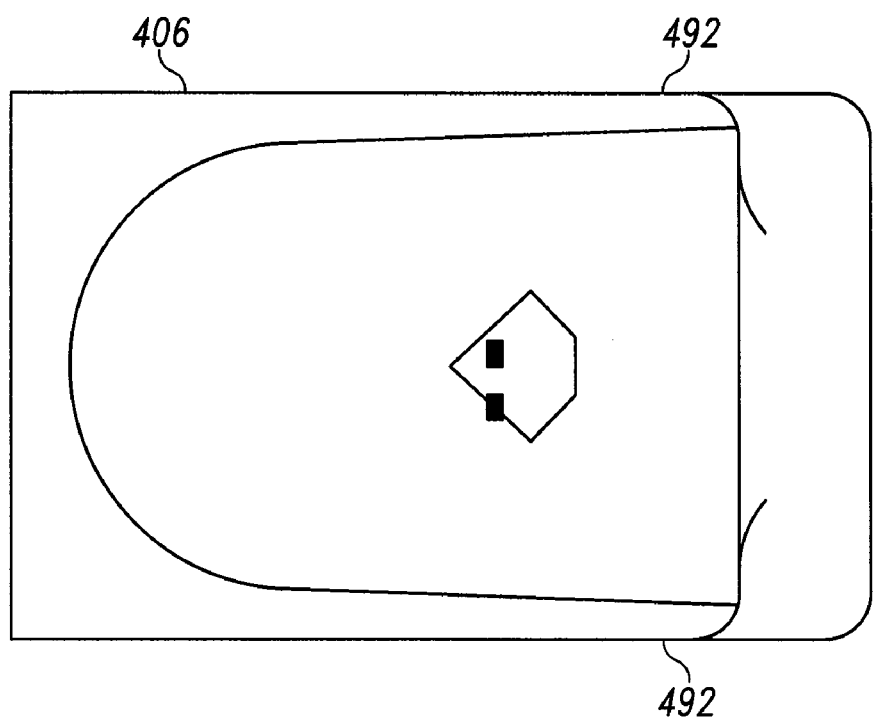
FIG. 12 is a bottom view of the unconstrained ulnar component of FIG. 10.

Referring now to FIGS. 10 through 12, the unconstrained ulnar articulating component 406 is shown in greater detail. The ulnar unconstrained articulating component 406 includes the ulnar articulating surface 462 that may have a concave periphery or surface 462 as shown in FIG. 10. The ulnar articulating surface 462 may, as shown in FIG. 10, be defined by a radius R extending from origin 461. The ulnar unconstrained articulating component 406 includes a pair of spaced apart protrusions 492 which include a bottom surface 491 and an angled surface 493 forming an angle alpha α therebetween. The angle α may be, for example, ten to eighty degrees or, for example, around 45°.

Referring now to FIGS. 11 and 12, the articulating surface 462 of the ulnar unconstrained articulating component may include a pair of angular ribs 463. The ribs 463 may mate with features on the humeral unconstrained articulating component 418 to provide restraint for the elbow prosthesis 472 in the direction of axis 465 of the articulating surface 462.

Figure 13:
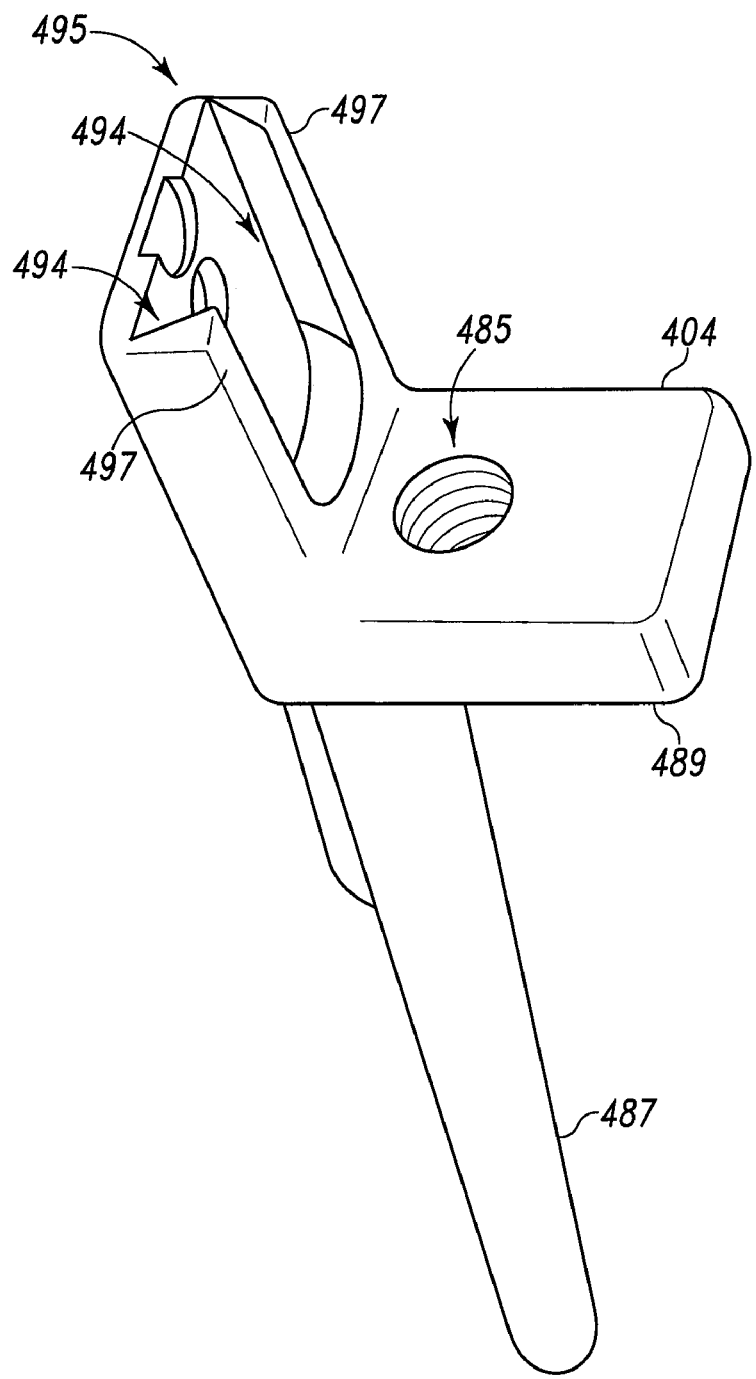
FIG. 13 is a perspective view of the ulnar stem component of the elbow prosthesis assembly of FIG. 9.
Figure 14:
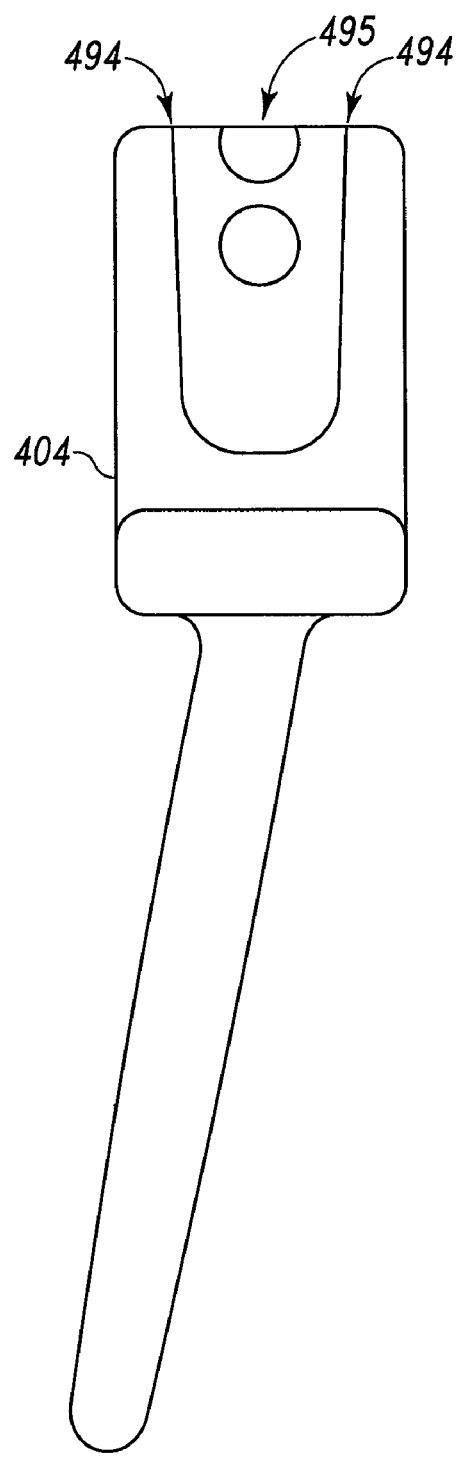
FIG. 14 is a plan view of the stem component of FIG. 13.
Figure 15:
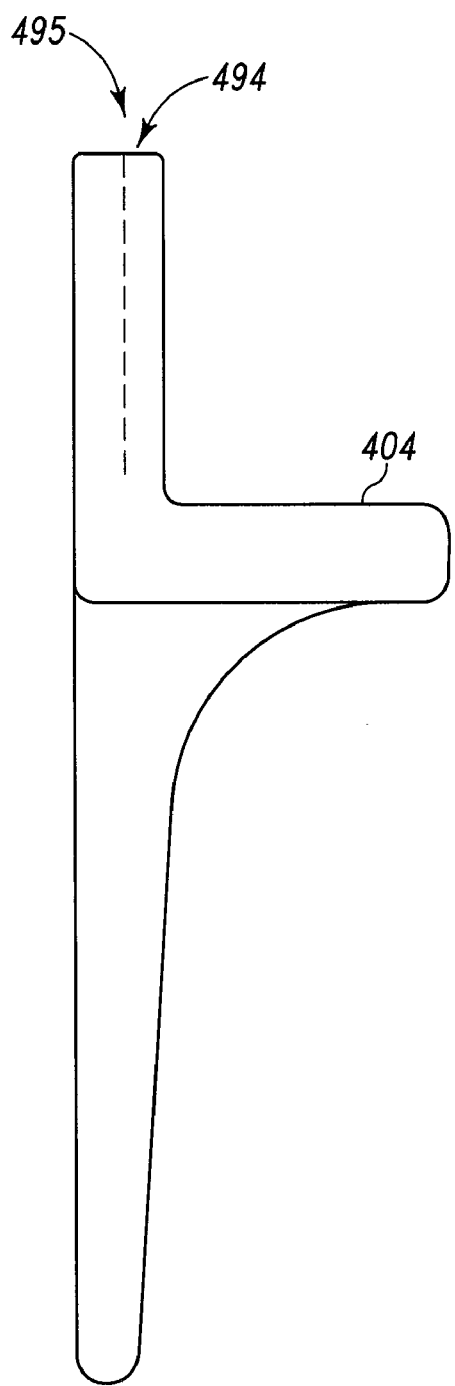
FIG. 15 is a side view of the stem component of FIG. 13.

Referring now to FIGS. 13 through 15, the ulnar stem component 404 is shown in greater detail. The ulnar stem component 404 includes a pocket 495 for receiving a portion of the ulnar unconstrained articulating component 406. The pocket 495 is defined by an inwardly extending rims 497 which are spaced apart. The rims 497 define spaced apart voids 494 for cooperation with the protrusions 492 of the ulnar unconstrained articulating component 406.

The ulnar stem component 404 may also include a central body portion 489 positioned between stem portion 487 and the pocket 495 of the ulnar stem component 404. The body portion 489 may include a threaded opening 485 for assisting in the removal of the ulnar stem component 404 from the cavity 2 of the ulna 4.

Figure 16:
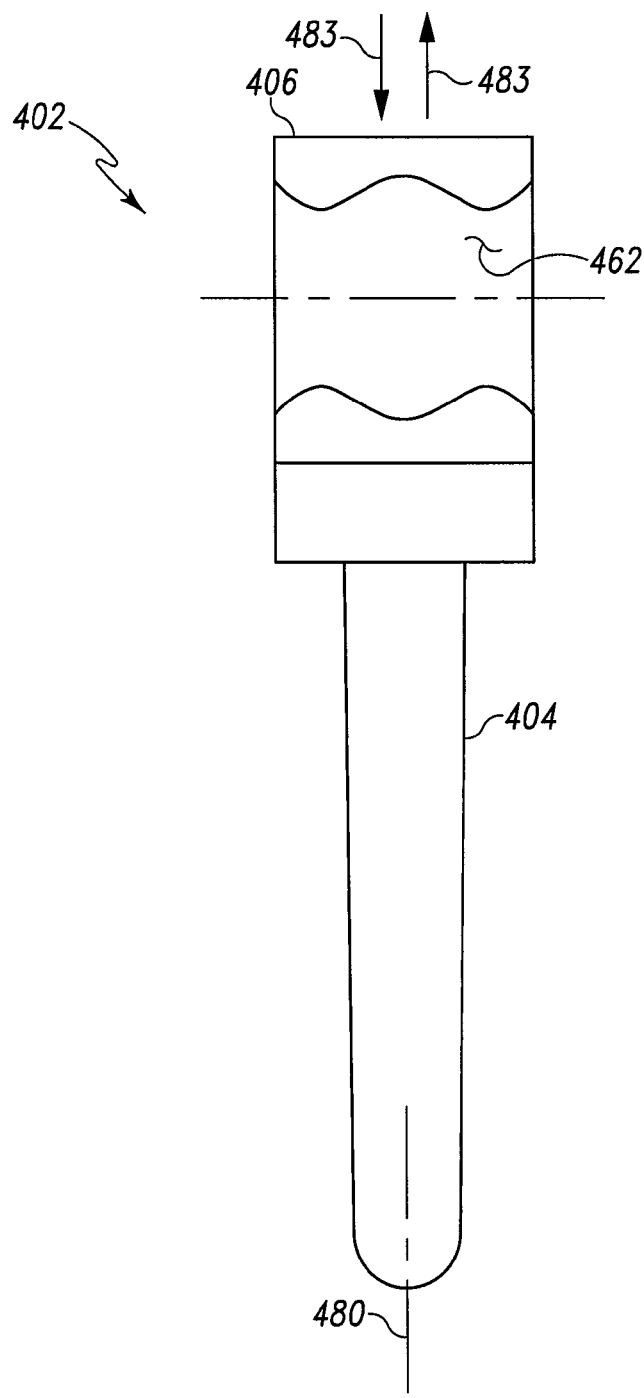
FIG. 16 is a plan view of the unconstrained ulnar component of FIG. 10 assembled onto the stem component of FIG. 13 to form an unconstrained ulnar assembly.
Figure 17:
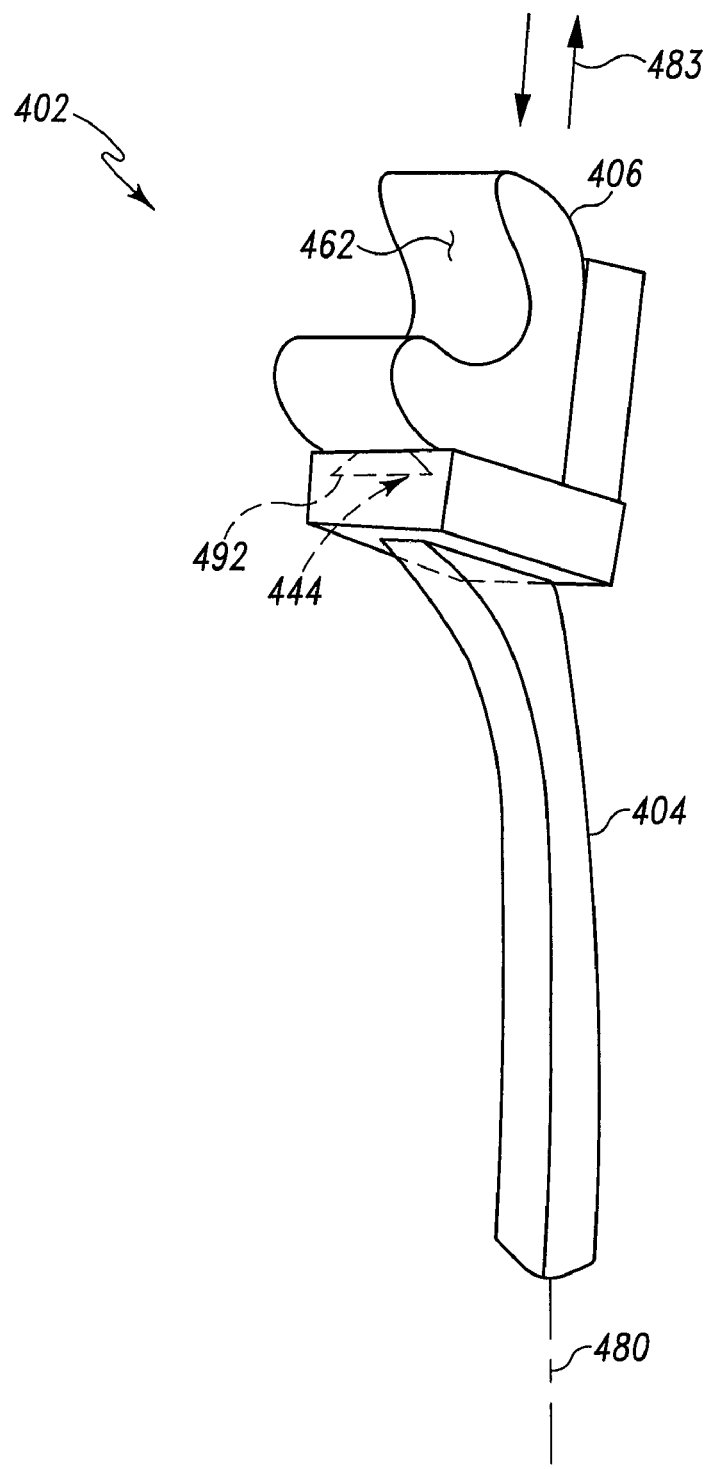
FIG. 17 is a perspective view of the unconstrained ulnar assembly of FIG. 16.

Referring now to FIGS. 16 and 17, the unconstrained ulnar articulating component 406 is shown in position on ulnar stem component 404. The ulnar unconstrained articulating component 406 is removable and assembled on to the ulnar stem component 404 along the ulnar stem centerline 480 in the direction of arrows 483.

Figure 18:
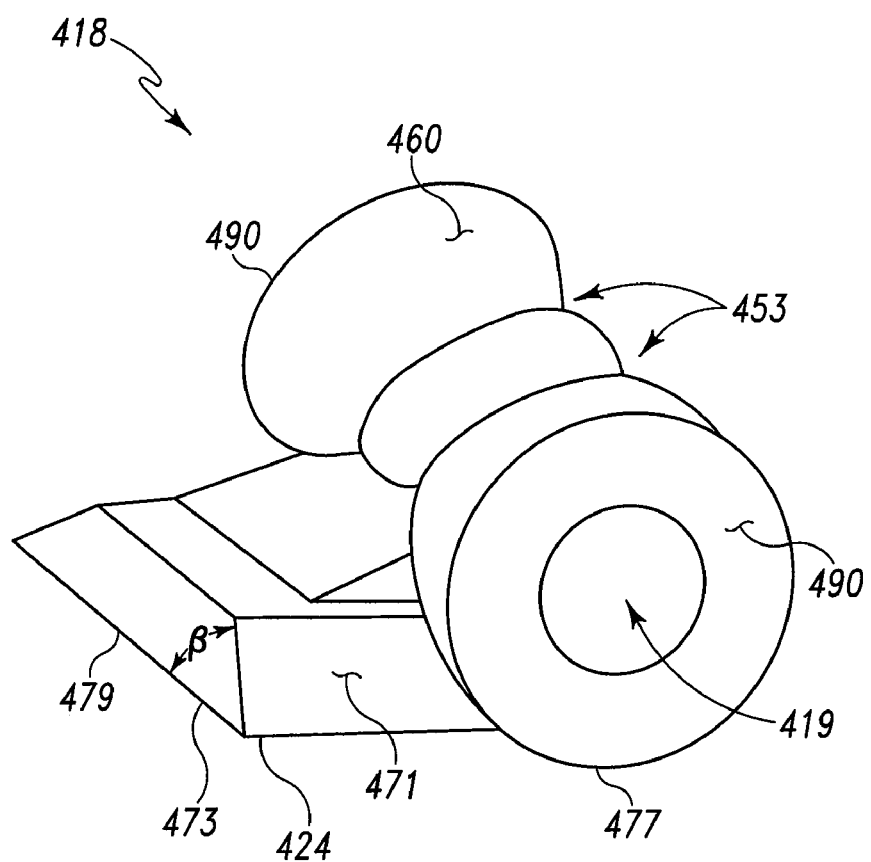
FIG. 18 is a perspective view of the articulating portion of the unconstrained humeral component of the unconstrained elbow prosthesis assembly of FIG. 9.

Referring now to FIG. 18, the unconstrained humeral articulating component 418 is shown in greater detail. As shown in FIG. 18, the unconstrained humeral articulating component 418 includes a base 479 to which a cylindrical portion 477 is attached. The base 479 includes a pair of spaced apart protrusions 424 which are formed by bottom 473 and end-faces 471. The bottom 473 and the end-faces 471 form an angle beta β there between. The angle β is similar to the angle α formed in the humeral stem component 112.

The cylindrical portion 477 is defined by opposed parallel ends 490 and peripheral articulating surface 460. The articulating surface 460 conforms to articulating surface 462 of the ulnar unconstrained articulating component 406. Articulating surface 460 further defines a pair of parallel spaced apart grooves 453 that mate with annular rings 463 formed on the ulnar articulating surface 462 of the ulnar unconstrained articulating component 406.

Figure 19:
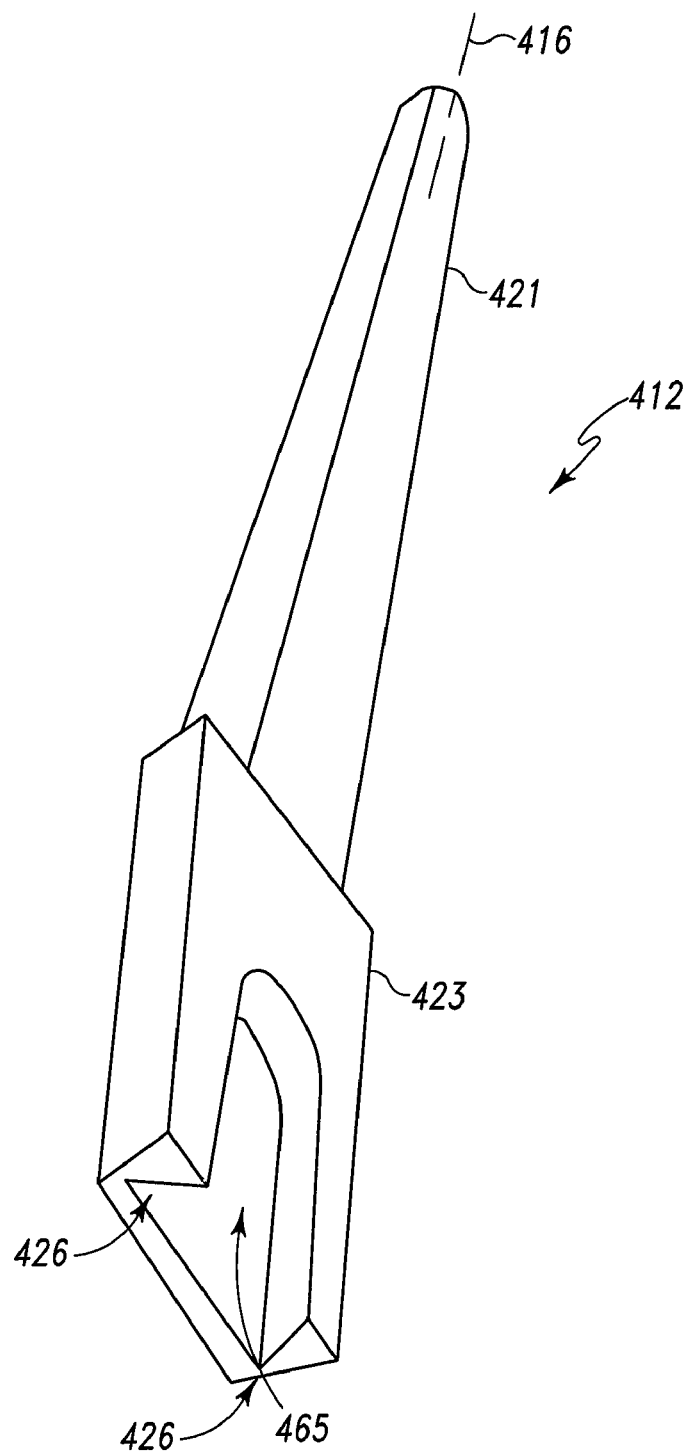
FIG. 19 is a perspective view of the humeral stem component of the unconstrained elbow prosthesis assembly of FIG. 9.
Figure 20:
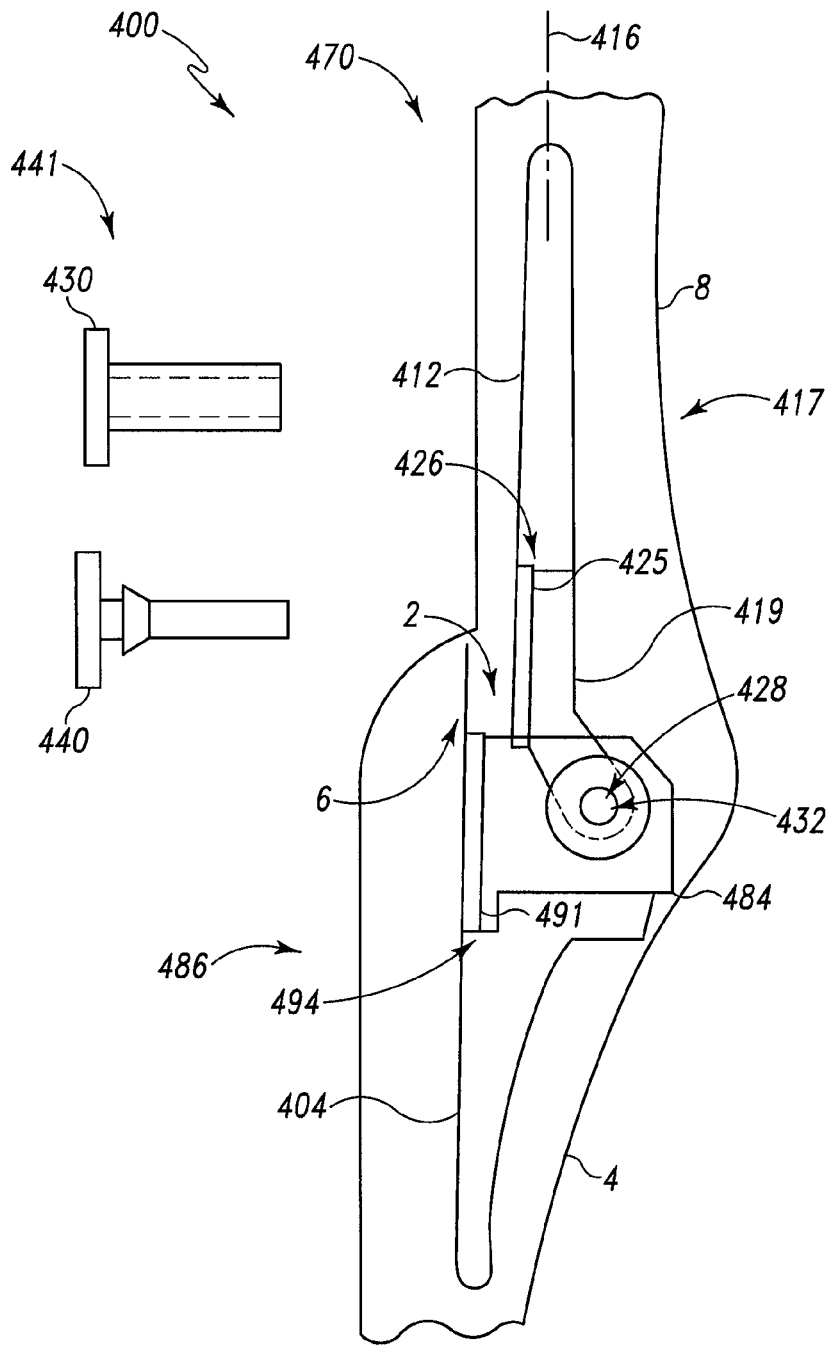
FIG. 20 is a plan view of the articulating humeral component of the semi-constrained humeral assembly of the semi-constrained elbow prosthesis assembly corresponding to the unconstrained elbow prosthesis assembly of FIG. 9.

Referring now to FIG. 19, the humeral stem component 412 is shown in greater detail. The humeral stem component 412 includes a stem portion 421, which defines humeral stem centerline 416. A humeral stem body portion 423 extends from the stem portion 421 of the humeral stem component 412. The body portion 423 defines a pocket 465 in the body portion 423. The pocket 465 is designed to mate with the base 479 of the humeral unconstrained articulating component 418 of FIG. 9. The pocket 465 defines a pair of spaced apart voids 426, which mate with protrusions 424 in the base 479 of the unconstrained humeral articulating component 418.

Referring now to FIG. 20, the semi-constrained elbow prosthesis 470 of the total elbow prosthesis 400 is shown. The semi-constrained elbow prosthesis 470 includes a humeral semi-constrained assembly 417 including the humeral stem component 412, which is placed in cavity 6 of the humerus 8. The humeral semi-constrained assembly 417 further includes humeral semi-constrained articulating component 419, which is slidably secured to the humeral stem component 412.

The humeral semi-constrained component 419 may be slidably secured to the humeral stem component 412 in any suitable fashion. For example and as shown in FIG. 20, the humeral semi-constrained articulating component 419 includes a pair of spaced apart protrusions 425 which are slidably received by voids 426 formed in the humeral stem component 412.

The semi-constrained elbow prosthesis 470 further includes a ulnar semi-constrained assembly 486. The ulnar semi-constrained assembly 486 includes the ulnar stem component 404, which is fitted into cavity 2 of the ulna 4. An ulnar semi-constrained articulating component 484 is slidably fitted with the ulnar stem component 404.

The ulnar semi-constrained articulating component 484 may be slidably fitted to the ulnar stem component 404 in any suitable fashion. For example and as shown in FIG. 20, the ulnar semi-constrained articulating component 484 includes a pair of spaced-apart protrusions 491 which are slidably received in voids 494 formed on the ulnar stem component 404.

The semi-constrained elbow prosthesis 470 further includes connector 441 in the form of, for example and as shown in FIG. 20, a pin 430 which mates with cap 440 to form connection assembly 441. The pin 430 is slidably received in humeral opening 428 of humeral semi-constrained articulating component 419 and ulnar opening 432 of the ulnar semi-constrained articulating component 484.

Figure 21:
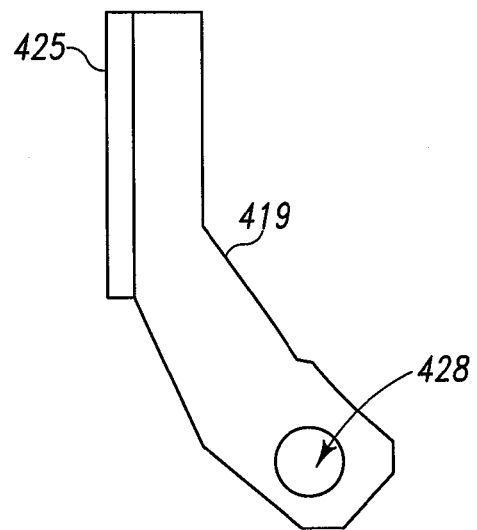
FIG. 21 is a plan view of the articulating ulnar component and the articulating humeral component of the semi-constrained elbow prosthesis assembly corresponding to the unconstrained elbow prosthesis assembly of FIG. 9.
Figure 21:
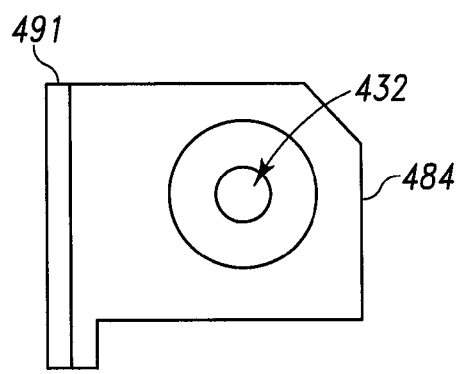

Referring now to FIG. 21, humeral semi-constrained articulating component 419 and the ulnar semi-constrained articulating component 484 are shown in greater detail. The humeral semi-constrained articulating component 419 includes the protrusions 425 as well as the humeral opening 428. The ulnar semi-constrained articulating component 484 includes the spaced-apart protrusions 491 as well as the ulnar opening 432.

Figure 22:
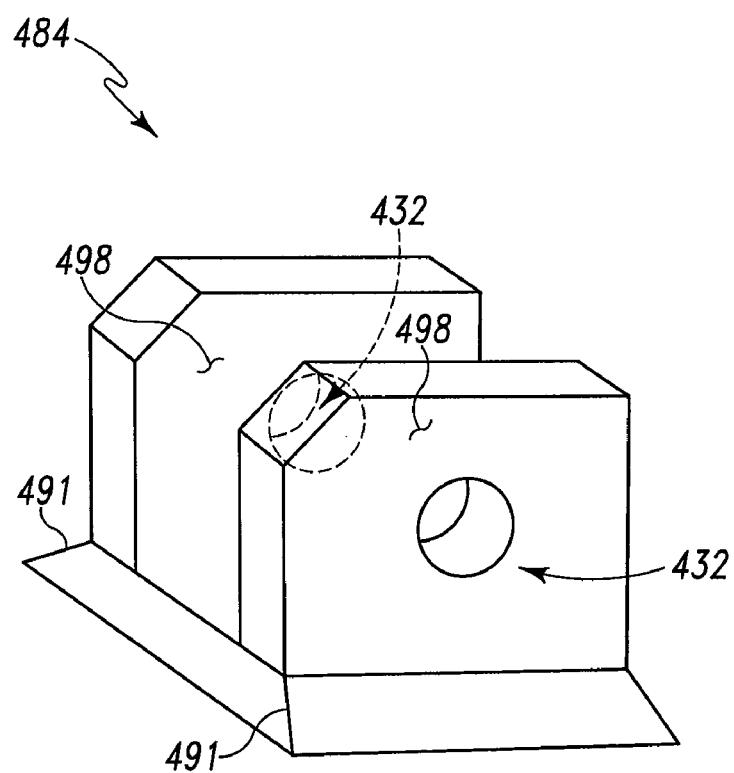
FIG. 22 is a perspective view of the articulating ulnar component of FIG. 21.

Referring now to FIG. 22, the ulnar semi-constrained articulating component 484 is shown in greater detail. The ulnar semi-constrained articulating component 484 includes the pair of spaced apart protrusions 491 for slidable cooperation with the ulnar stem component 404. The ulnar semi-constrained articulating component 484 further includes a pair of spaced apart internal side-walls 498 for receiving a portion of the humeral semi-constrained articulating component 419 therebetween, as well as ulnar openings 432 for receiving the pin 430.

Figure 23:
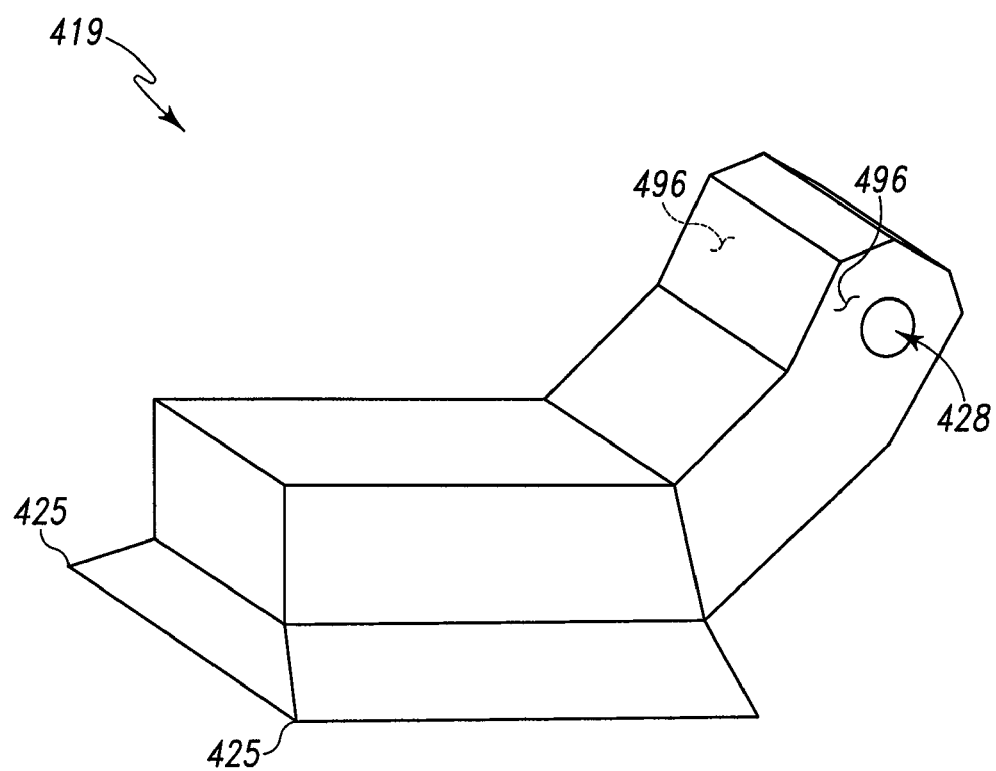
FIG. 23 is a perspective view of the articulating humeral component of FIG. 21.

Referring now to FIG. 23, the humeral semi-constrained articulating component 419 is shown in greater detail. The humeral semi-constrained articulating component 419 includes the pair of spaced apart protrusions 425 for cooperation with the humeral stem component 412. The humeral semi-constrained articulating component 419 also includes a pair of spaced-apart parallel ends 496 for slidable cooperation with the side faces 498 of the ulnar semi-constrained articulating component 484. The humeral semi-constrained articulating component 419 further includes the humeral opening 428 for receiving the pin 430.

According to the present invention and referring now to FIGS. 24 through 36, yet another embodiment of the present invention is shown as total elbow prosthesis 500. The total elbow prosthesis 500 includes a semi-constrained elbow prosthesis 570 as well as an unconstrained elbow prosthesis 572. The total elbow prosthesis 500 is similar to the total elbow prosthesis 400, except that the total elbow prosthesis 500 includes a connection in the form of, for example, a protrusion and a void to receive the protrusion.

Figure 24:
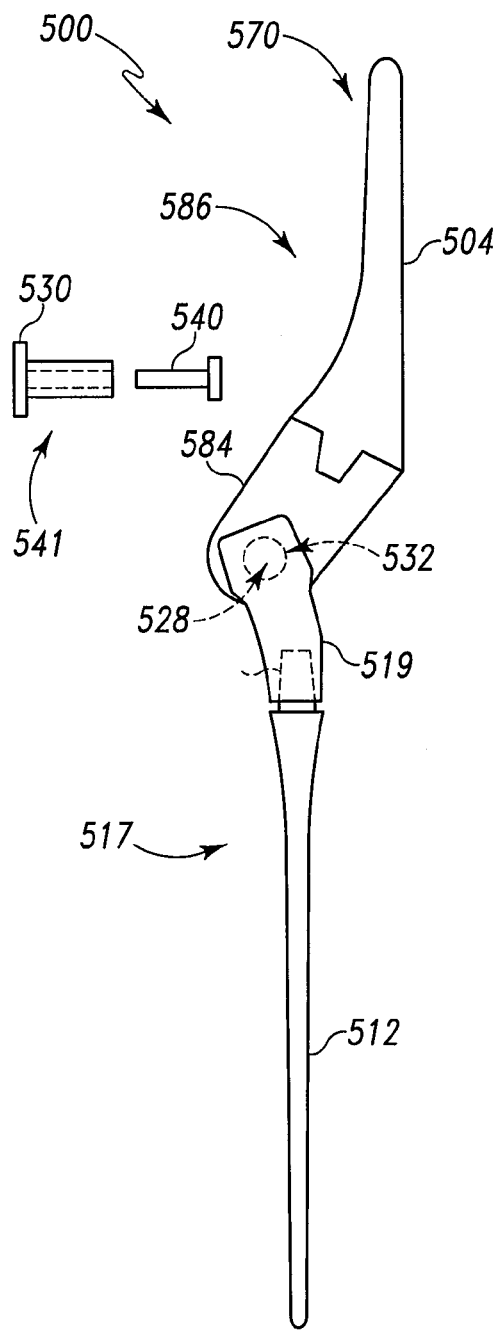
FIG. 24 is a medial/lateral view partially in cross section of a further embodiment of the present invention in the form of an elbow prosthesis assembly in position in a patient's arm including an semi-constrained elbow prosthesis assembly.

Referring now to FIG. 24, the semi-constrained elbow prosthesis 570 of the total elbow prosthesis 500 is shown. The semi-constrained elbow prosthesis 570 includes an ulnar semi-constrained assembly 586, which mates with a humeral semi-constrained assembly 517. As shown in FIG. 24, the ulnar semi-constrained assembly 586 is pivotably connected to the humeral semi-constrained assembly 517 by a connector 541 in the form of a pin 530 and a cap 540 which cooperate with each other.

The ulnar semi-constrained assembly 586 includes an ulnar semi-constrained articulating component 584, which is removably connected to ulnar stem component 504. Similarly, the humeral semi-constrained assembly 517 includes a humeral semi-constrained articulating component 519, which is slidably removably connected to humeral stem component 512. The humeral semi-constrained articulating component 519 defines a humeral opening 528 and the ulnar semi-constrained articulating component 584 defines an ulnar opening 532. The pin 530 is adapted for being slidably fitted into the ulnar opening 532 and the humeral opening 528 to form the semi-constrained elbow prosthesis 570.

Figure 25:
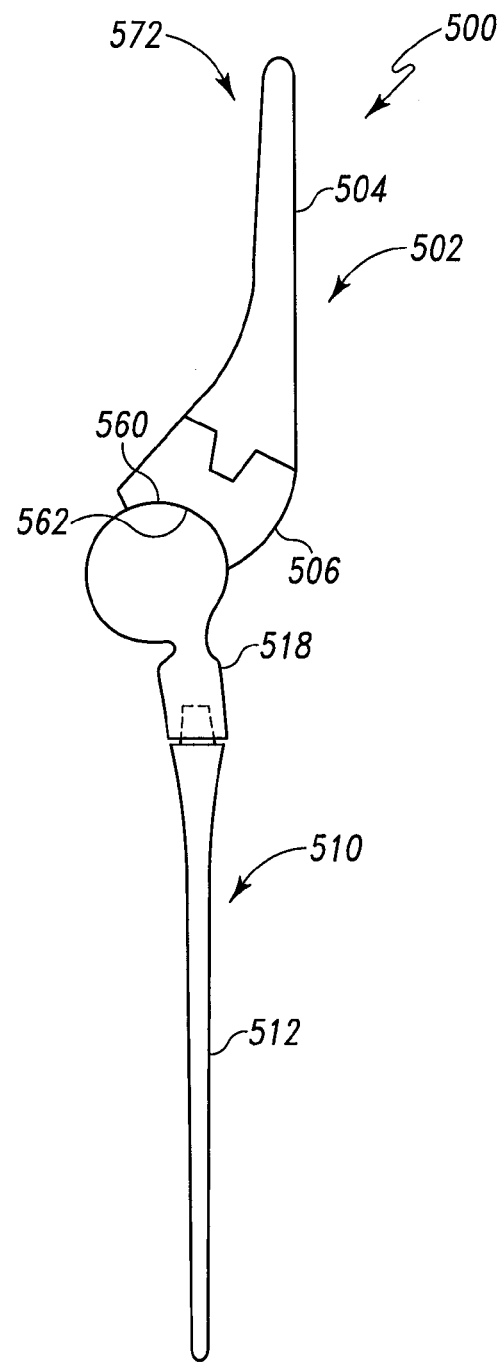
FIG. 25 is an medial/lateral view partially in cross section of an unconstrained elbow prosthesis assembly shown in position implanted in a humerus and an ulna corresponding to the semi-constrained elbow prosthesis assembly of FIG. 24.

Referring now to FIG. 25, the unconstrained elbow prosthesis 572 is shown. The unconstrained elbow prosthesis 572 includes ulnar unconstrained assembly 502 which mates with a humeral unconstrained assembly 510 to form the unconstrained elbow prosthesis 572.

The ulnar-unconstrained assembly 502 includes an ulnar unconstrained articulating component 506, which is slidably connectable to ulnar stem component 504. The humeral unconstrained assembly 510 includes a humeral unconstrained articulating component 518, which is slidable fitted to humeral stem component 512. The humeral unconstrained articulating component 518 defines a humeral articulation surface 560 which mates with ulnar articulating surface 562 formed on the ulnar unconstrained articulating component 506.

Figure 26:
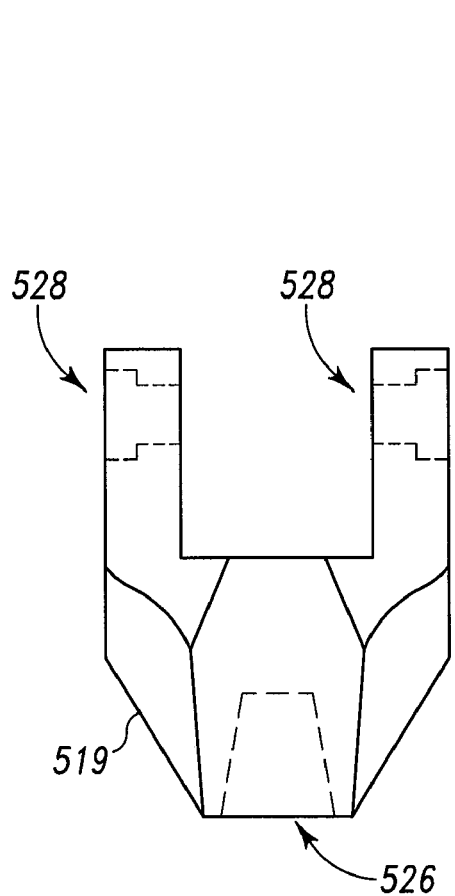
FIG. 26 is a plan view of the humeral articulating component of a semi-constrained humeral assembly of the semi-constrained elbow prosthesis assembly of FIG. 24.

Referring now to FIG. 26, the humeral semi-constrained articulating component 519 is shown in greater detail. The humeral semi-constrained articulating component 519 includes a pair of spaced apart humeral openings 528 for receiving the pin 530 of the connector assembly 541. The humeral semi-constrained articulating component 519 further includes a void 526 in the form of a conofrustrical cavity. The void 526 is used for receiving the humeral stem component 512.

Figure 27:
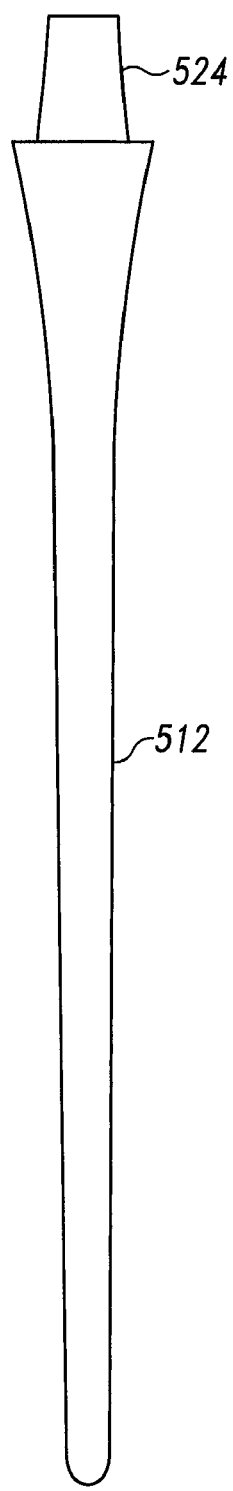
FIG. 27 is a plan view of the stem component of a semi-constrained humeral assembly of the semi-constrained elbow prosthesis assembly of FIG. 24.

Referring now to FIG. 27, the humeral stem component 512 is shown in greater detail. The humeral stem component 512 includes a protrusion 524 extending from the stem 512. The protrusion, 524, as shown in FIG. 27, has a tapered or generally conofrustrical shape. The protrusion 524 is adapted to be positioned in void 526 of the humeral semi-constrained articulating component 519.

Figure 28:
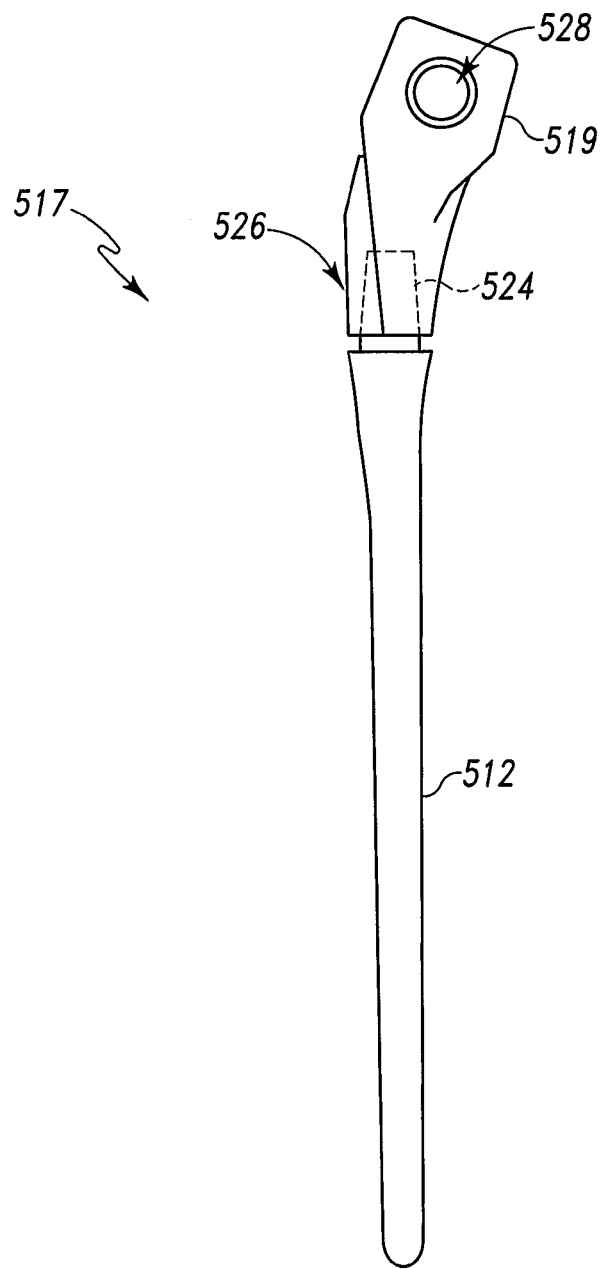
FIG. 28 is a side or lateral view of the semi-constrained humeral assembly of the semi-constrained elbow prosthesis assembly of FIG. 24.

Referring now to FIG. 28, the humeral stem component 512 is shown in an assembled configuration with the humeral semi-constrained articulating component 519 to form the humeral semi-constrained assembly 517. The humeral stem component 512 includes the protrusion 524, which is positioned in the void 526 of the humeral semi-articulating component 519 to form the assembly 517. The humeral semi-articulating component 519 defines the humeral opening 528 for receiving the pin 530.

It should be appreciated that the protrusion 524 and the void 526 may be fitted to provide for a temporary locking condition between the two providing for a rigid connection of the semi-articulating component 519 and the humeral stem component 512. Alternatively, it should be appreciated that the protrusion 524 and the void 526 may be sized to provide for a loose fit or for possible rotation of the humeral semi-articulating component 519 with respect to the humeral stem component 512.

Figure 28A:
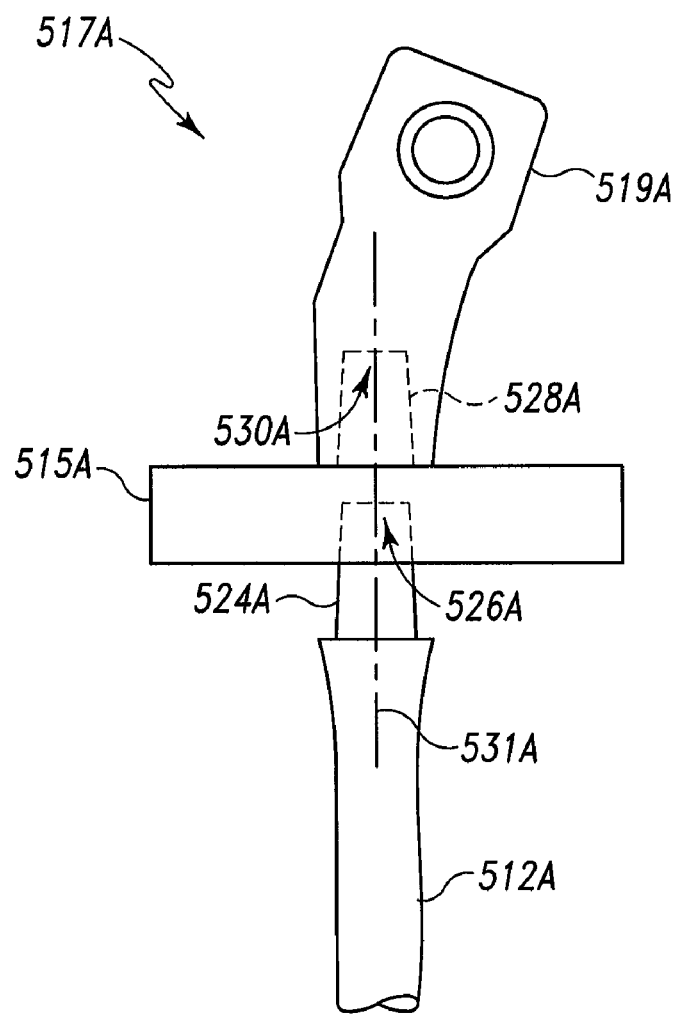
FIG. 28A is a partial end view of a semi-constrained humeral assembly of another embodiment of the present invention in the form of an elbow prosthesis with a mobile bearing humeral component.

For example, and as shown in FIG. 28A, an additional component in the form of a bearing, for example bearing 515A may be positioned between the components of the humeral semi-constrained assembly to provide for the rotation of the humeral semi-constrained articulating component with respect to the stem component.

For example, and as shown in FIG. 28A, yet another embodiment of the present invention is shown as humeral semi-constrained assembly 517A. The humeral semi-constrained assembly 517A includes a humeral stem component 512A similar to humeral stem component 512 of the assembly 517 of FIG. 28. The humeral stem component 512A includes a protrusion 524A, which is received in void 526A of bearing 515A. The bearing 515A is positioned between the humeral stem component 512A and humeral semi-articulating component 519A. The humeral semi-articulating component 519A is similar to the humeral semi-constrained articulating component 519 of FIG. 28. The bearing 515 includes a protrusion 528A, which is received in void 530A of the articulating component 519A. The bearing 515A serves to assist in permitting angular rotation of the humeral semi-constrained articulating component 519A with respect to the humeral stem component 512A about axis of rotation 531A.

The bearing 515A may be made of any suitable durable material and may, for example, be made of a plastic. If made of a plastic, the bearing 515A may be made of polyethylene, for example, an ultra-high molecular weight polyethylene.

The bearing 515A may be rigidly connected to either the protrusion 524A of the stem 512A or to the void 530A of the articulating component 519A. Alternatively, bearing 515A may be the rotatably fitted to both the stem component 512A and the articulating component 519A. It should be appreciated that the protrusions 524A and 528A may be cylindrical rather than conofrustrical. Further, the protrusions and voids of the humeral assembly 517A may be reversed.

Figure 29:
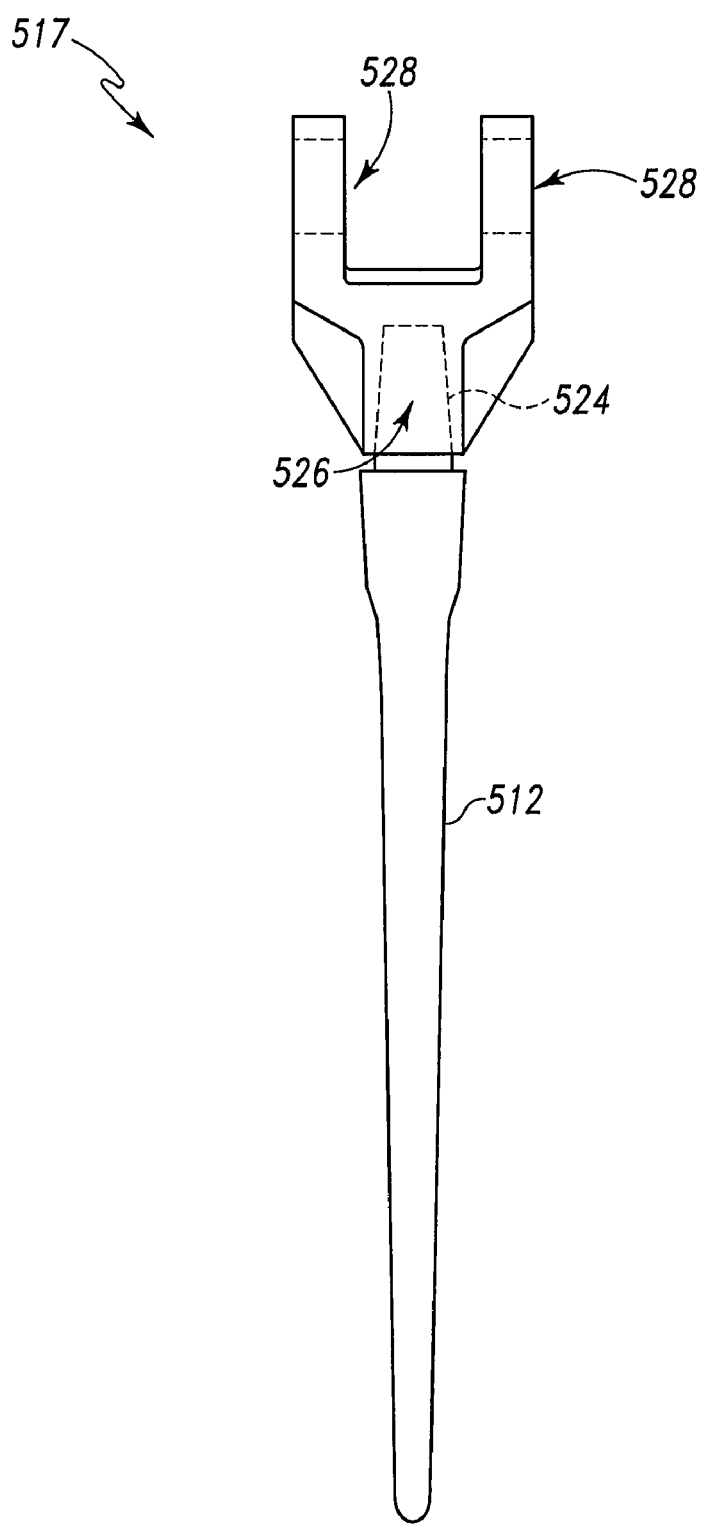
FIG. 29 is an plan view of the semi-constrained humeral assembly of FIG. 28.

Referring now to FIG. 29, another view of the humeral semi-constrained assembly 517 is shown, showing the pair of spaced apart humeral openings 528 formed in the humeral semi-constrained articulating component 519.

It should be appreciated that the protrusions and the voids of the present invention may have a shape other than a conofrustrical shape. For example, the protrusions and voids may be, for example, cylindrical. A cylindrical shape may be well-suited for a bearing or rotatable connection of the articulating component with the stem component.

Figure 29A:
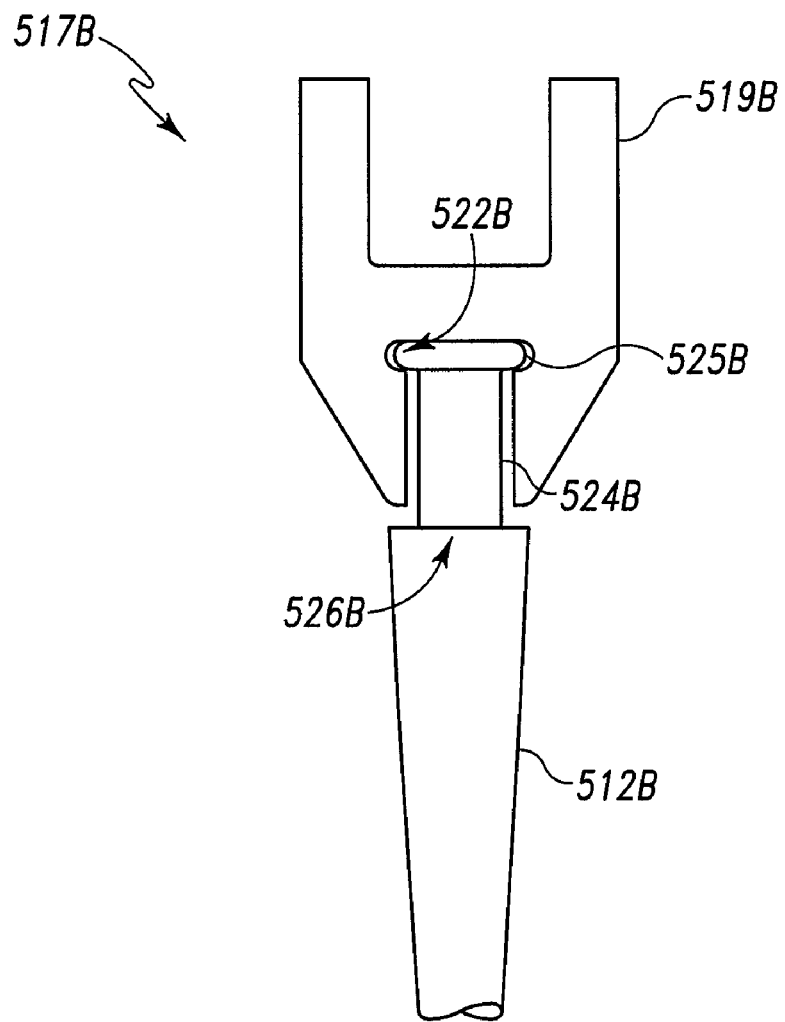
FIG. 29A is a partial plan view of a semi-constrained humeral assembly of yet another embodiment of the present invention in the form of an elbow prosthesis with an cylindrical connections.

For example, referring now to FIG. 29A, yet another embodiment of the present invention is shown as humeral assembly 517B. The humeral assembly 517B includes a stem component 512B, which mates with an articulating component 519B. The stem component 512B includes a cylindrical portion 524B, which is received in cylindrical void 526B formed on the articulating component 519B. While the protrusion 524B and the cylindrical void 526B may be a simple cylindrical shape, the humeral assembly 517B may include a feature for providing a secure connection of the articulating component 519B to the stem 512B.

For example, and as shown in FIG. 29A, such a connection may be in the form of a rib 525B extending from the cylindrical protrusion 524B. The rib 525B may mate with a groove 522B formed in the articulating component 519B. It should be appreciated that the articulating component 519B may be either a semi-constrained component or an unconstrained component. It should also be appreciated that the cylindrical protrusion 524B and the void 526B may be designed into a connection for an ulnar component as well.

Figure 30:
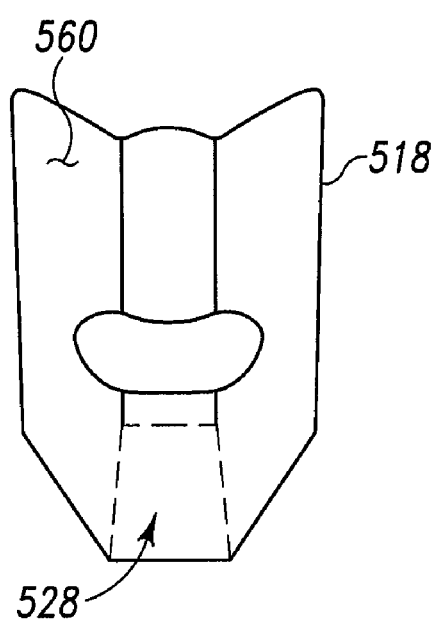
FIG. 30 is a plan view of the humeral articulating component of an unconstrained humeral assembly of the unconstrained elbow prosthesis assembly of FIG. 25.

Referring now to FIG. 30, the humeral unconstrained articulating component 518 is shown in greater detail. The humeral unconstrained articulating component 518 defines a void 528 for receiving the humeral stem component 512 as well as a humeral articulating surface 560 for mating with the ulnar articulating surface 562. The humeral articulating surface may be convex. It should also be appreciated that the humeral articulating surface 560 may likewise be concave. The humeral articulating surface 560 may have a generally cylindrical shape or may, as shown in FIG. 30, include a "W" shaped cross-section for gently urging the prosthetic components into their proper rotating positions.

Figure 31:
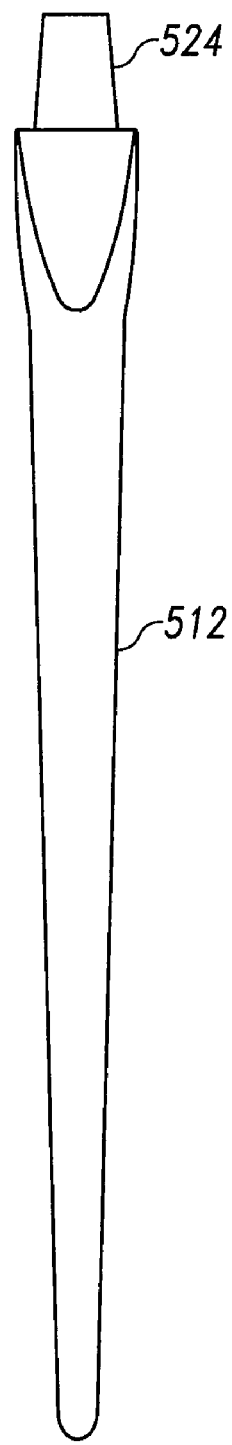
FIG. 31 is a plan view of the stem component of FIG. 27 which may also be used with the unconstrained humeral assembly of the unconstrained elbow prosthesis assembly of FIG. 25.

Referring now to FIG. 31, humeral stem component 512 is shown with the protrusion 524.

Figure 32:
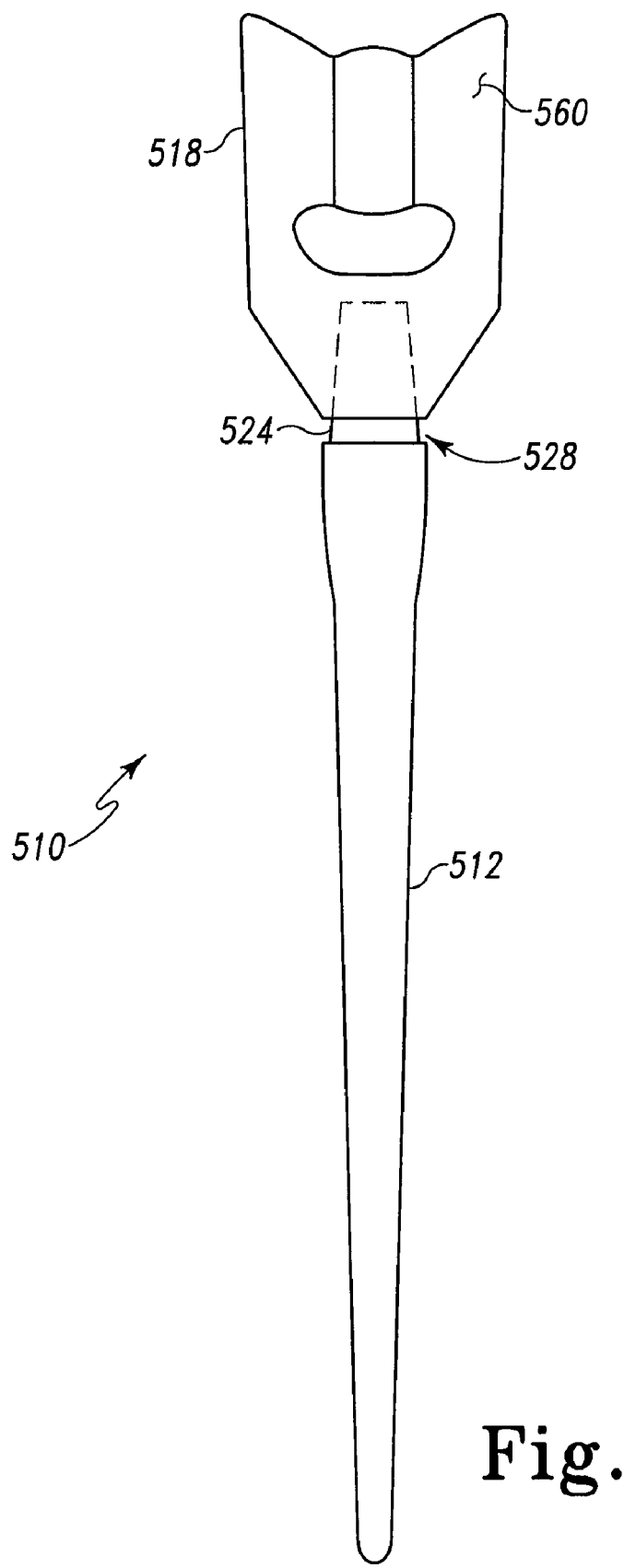
FIG. 32 is a plan view of the articulating humeral component of FIG. 30 assembled onto the stem component of FIG. 31 to form the unconstrained humeral assembly of the unconstrained elbow prosthesis assembly of FIG. 25.

Referring now to FIG. 32, the humeral unconstrained articulating component 518 is shown in position on humeral stem component 512 to form humeral unconstrained assembly 510. The protrusion 524 of the stem 512 is fitted in void 528 of the articulating component 518. The articulating surface 560 of the articulating component 518 is adapted for cooperation with the articulating surface 562 of the ulnar unconstrained articulating component 506.

Figures 33, 34:
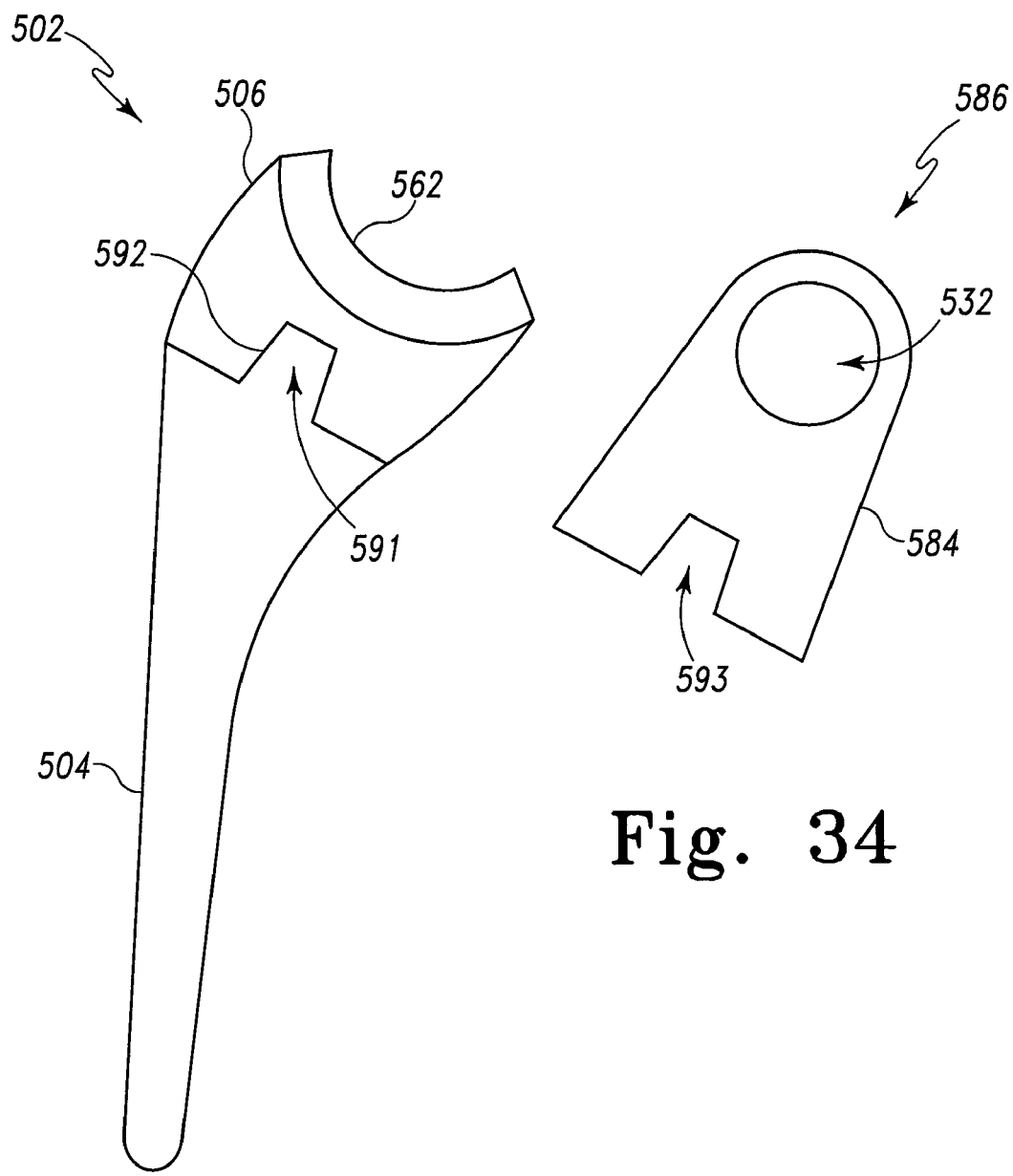
FIG. 33 is an side view of an articulating unconstrained ulnar component assembled onto an ulnar stem component to form the unconstrained ulnar assembly of the unconstrained elbow prosthesis assembly of FIG. 25.
FIG. 34 is an end view of an articulating semi-constrained ulnar component for use with the ulnar stem component of FIG. 33 to form the semi-constrained ulnar assembly of the semi-constrained elbow prosthesis assembly of FIG. 25.
Figures 35, 36:
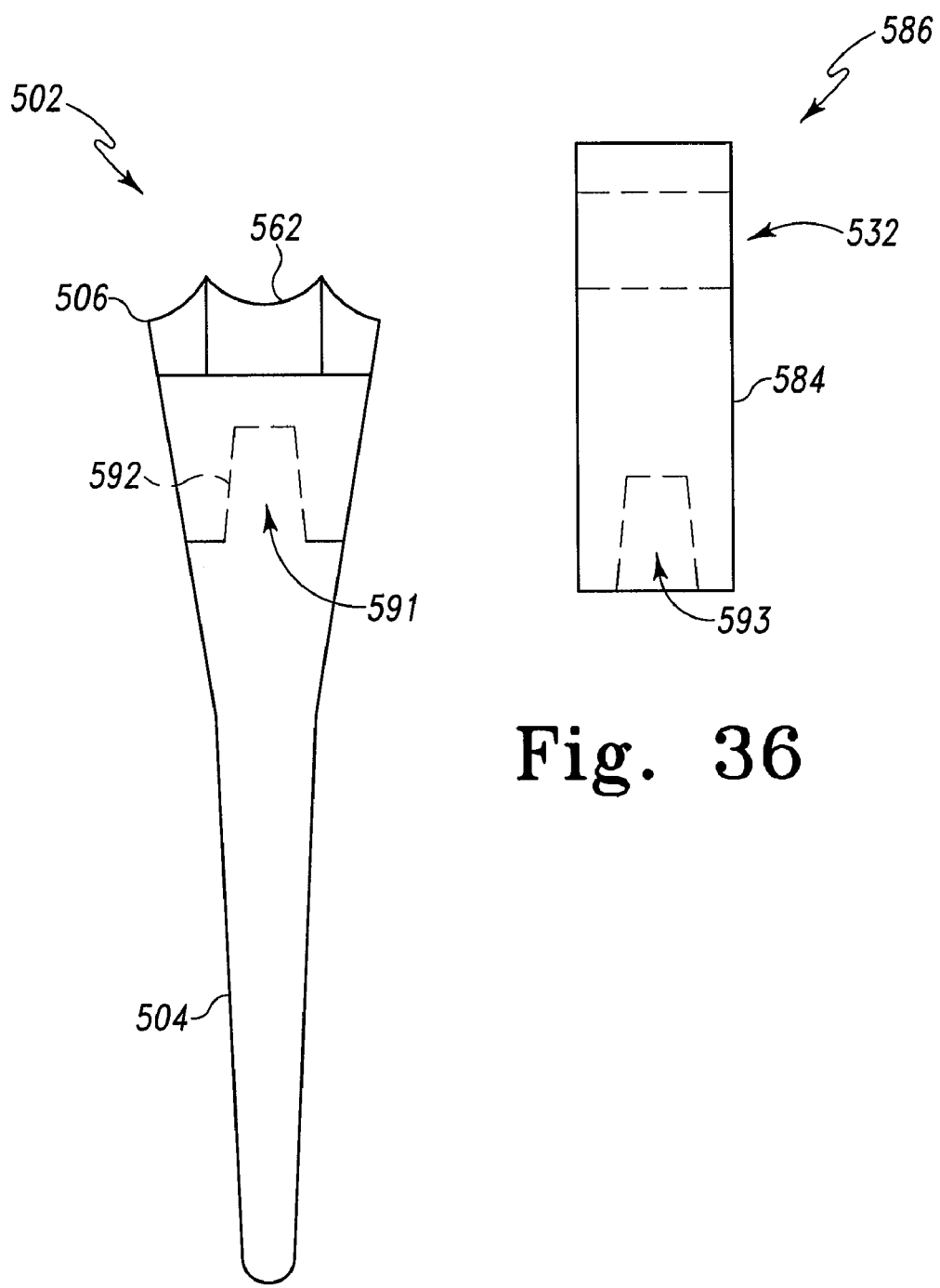
FIG. 35 is a plan view of the unconstrained ulnar assembly of FIG. 33.
FIG. 36 is a plan view of the articulating semi-constrained ulnar component of FIG. 34.

Referring now to FIGS. 33 and 35, the ulnar stem component 504 is shown in position on the ulnar unconstrained articulating component 506 to form the ulnar unconstrained assembly 502. The ulnar stem component 504 includes an ulnar stem protrusion 592, which is received in void 591 formed in the ulnar unconstrained articulating component 506.

The ulnar unconstrained articulating component includes an ulnar articulating surface 562 for cooperation with the humeral articulating surface 560. The ulnar articulating surface, as shown in FIG. 35, may have a generally "M" shaped cross-section for cooperating with the generally "W" shaped cross-section of the humeral articulating surface 560 of the humeral unconstrained articulating component 518.

Referring now to FIGS. 34, 35 and 36, the ulnar semi-constrained articulating component 584 is shown in greater detail. The ulnar semi-constrained articulating component 584 defines an ulnar void 593 which has a size and shape generally similar to the void 591 formed in the ulnar unconstrained articulating component 506 so that both the ulnar unconstrained articulating component 506 as well as the ulnar semi-constrained articulating component 584 may mate with the ulnar stem component 504. The ulnar semi-constrained articulating component 584 defines the ulnar opening 532 for cooperation with the pin 530 to secure ulnar semi-articulating assembly 586 to the humeral semi-constrained assembly 517 to form the semi-constrained elbow prosthesis 570.

Figure 37:
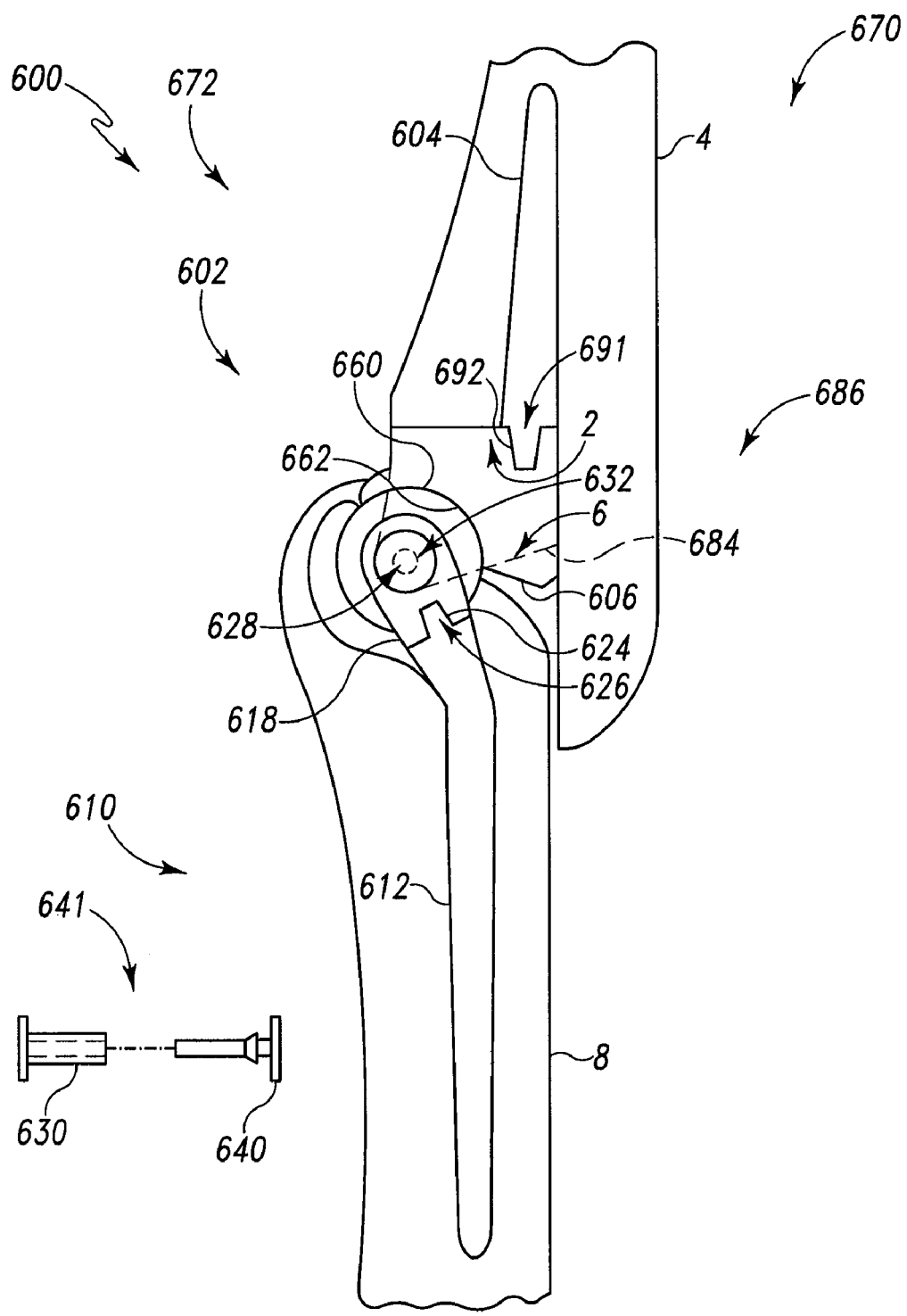
FIG. 37 is an medial/lateral view partially in cross section of yet another embodiment of the present invention in the form of an elbow prosthesis assembly in position in a patient's arm including an unconstrained elbow prosthesis assembly shown in position implanted in a humerus and an ulna.
Figure 38:
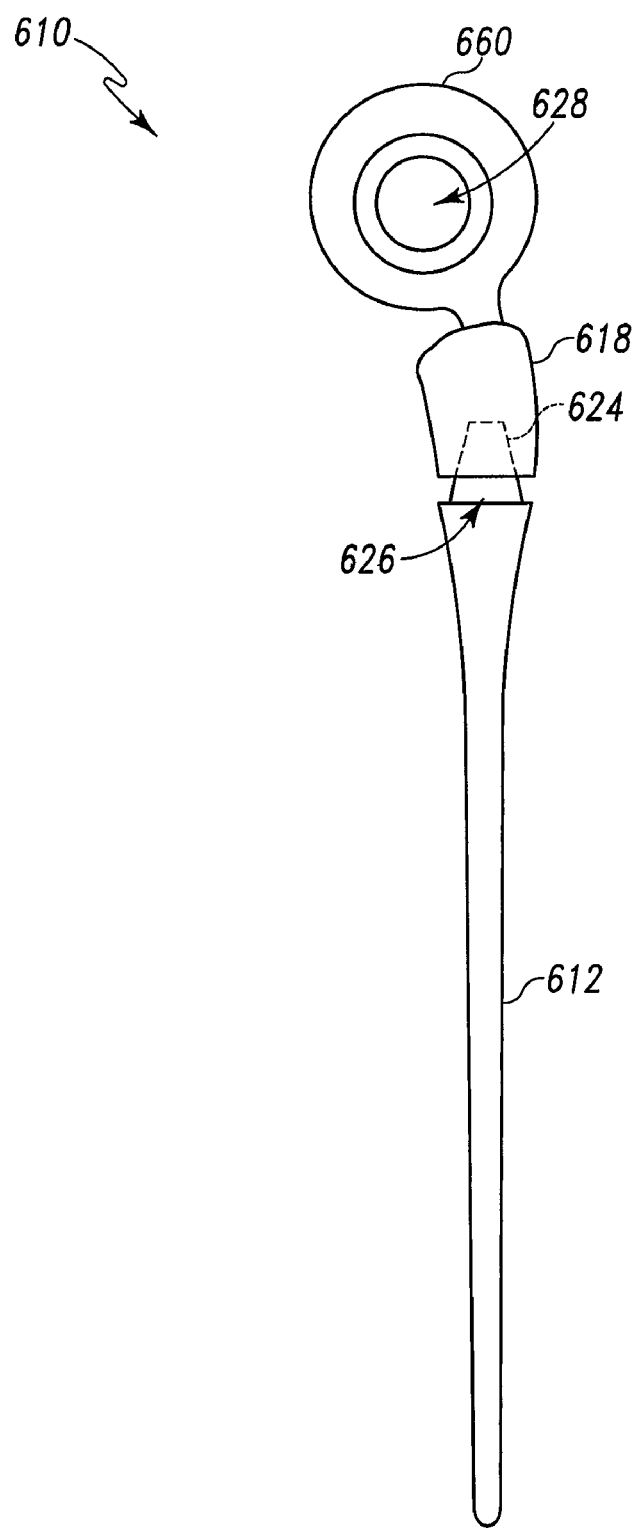
FIG. 38 is an side view of the humeral component of the elbow prosthesis assembly of FIG. 37 that may be used both with an unconstrained elbow prosthesis assembly and with a semi-constrained elbow prosthesis assembly.
Figure 39:
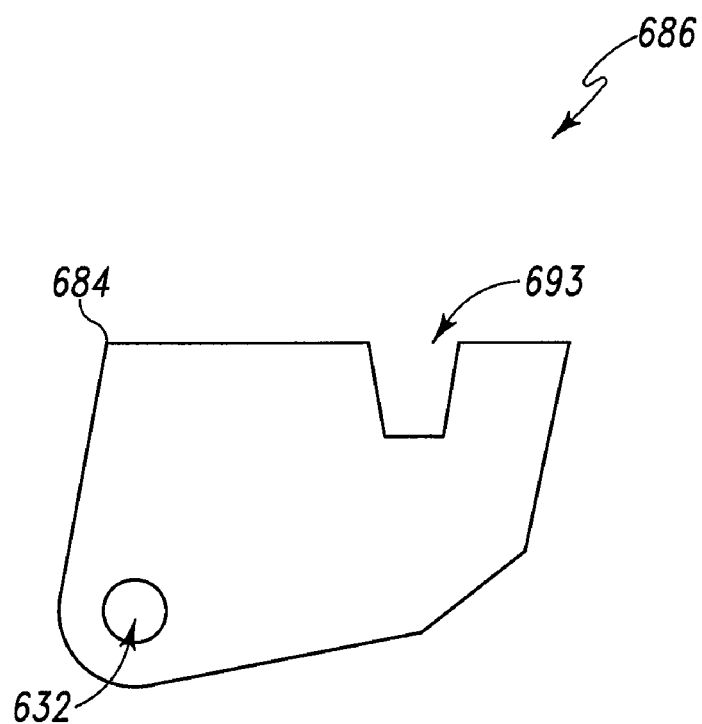
FIG. 39 is a end view of the articulating ulnar component of the semi-constrained ulnar assembly of the semi-constrained elbow prosthesis assembly corresponding to the unconstrained elbow prosthesis assembly of FIG. 37.

Referring now to FIGS. 37 through 39, yet another embodiment of the present invention is shown as total elbow prosthesis 600. The total elbow prosthesis 600 includes a semi-constrained elbow prosthesis 670 as well as unconstrained elbow prosthesis 672. The total elbow prosthesis 600 is different than the total elbow prosthesis 500 of FIGS. 24 through 36, in that the humeral assembly of the total elbow prosthesis 600 may be identical for both the semi-constrained as well as the unconstrained elbow prosthesis configurations.

For example, and referring now to FIG. 37, the semi-constrained elbow prosthesis 670 includes ulnar semi-constrained assembly 686 as well as humeral assembly 610. The ulnar semi-constrained assembly 686 is secured to the humeral assembly 610 with a connecting assembly 641 including pin 630 which mates with cap 640.

The ulnar semi-constrained assembly 686 includes an ulnar stem component 604, which is fitted in cavity 2 of the ulna 4. The ulnar semi-constrained assembly 686 further includes an ulnar semi-constrained articulating component 684 which mates with the ulnar stem component 604 to form the ulnar semi-constrained assembly 686.

Continuing to refer to FIG. 37, the semi-constrained elbow prosthesis 670 further includes the humeral assembly 610. The humeral assembly 610 includes a humeral stem component 612, which is fitted into cavity 6 of the humerus 8. A humeral articulating component 618 is fitted to the humeral stem component 612 to form the humeral assembly 610.

Referring to FIGS. 37 and 39, the ulnar semi-constrained assembly 686 is shown and described in greater detail. The ulnar semi-constrained assembly 686 includes ulnar semi-constrained articulating component 684. The ulnar semi-constrained articulating component 684 is separable from the ulnar stem component 604 in any suitable manner.

The ulnar stem component 604 includes a protrusion 692, which mates with void 691 formed in ulnar unconstrained articulating component 606. The ulnar semi-constrained articulating component 684 may include a void 693 which has a shape and configuration similar to the void 691 of ulnar unconstrained articulating component 606 so that the ulnar stem component 604 is compatible both with the ulnar semi-constrained articulating component 684 as well as with the ulnar unconstrained articulating component 606. The ulnar semi-constrained articulating component 684 includes an ulnar opening 632 for receiving the pin 630.

For example, and as shown in FIG. 37, the total elbow prosthesis 600 further includes the unconstrained elbow prosthesis 672. The unconstrained elbow prosthesis 672 includes ulnar unconstrained assembly 602 which is formed from the ulnar stem component 604 as well as ulnar unconstrained articulating component 606. The unconstrained elbow prosthesis 672 further includes the humeral assembly 610, which consists of the humeral stem component 612 and the humeral articulating component 618. Humeral articulating surface 660 of the humeral articulating component 618 mates with ulnar articulating surface 662 of the ulnar unconstrained articulating component 606 to form the unconstrained elbow prosthesis 672.

Referring now to FIG. 38, the humeral assembly 610 is shown in greater detail. The humeral assembly 610 includes humeral stem component 612, which as is shown in FIG. 38, is removably connected to the humeral articulating component 618. As shown in FIG. 38, the articulating component 618 includes the articulating surface 660, so that the humeral assembly 610 may be used in an unconstrained prosthesis. The articulating component 618 also includes humeral opening 628 so that the humeral assembly 610 may be used in a semi-constrained prosthesis. Since the humeral assembly 610 may be used in both an unconstrained and a semi-constrained prosthesis, it should be appreciated that the humeral assembly 610 may be integral.

As shown in FIG. 38, the humeral assembly 610 maybe modular or may be comprised of the humeral stem component 612 which is separable from the humeral articulating component 618. The components 612 and 618 may be separable and connectable in any suitable manner and may, as shown in FIG. 38, have a tapered connection.

As shown in FIG. 38, the humeral stem component 612 may include a protrusion 624, which mates with a void 626 formed in the articulating component 618. The use of the protrusion 624 and the void 626 permits the articulating component 618 to be separated from the stem assembly so that the pin 630 and the cap 640 may be removed without removing any condylar portion of the humerus 8.

Figure 40:
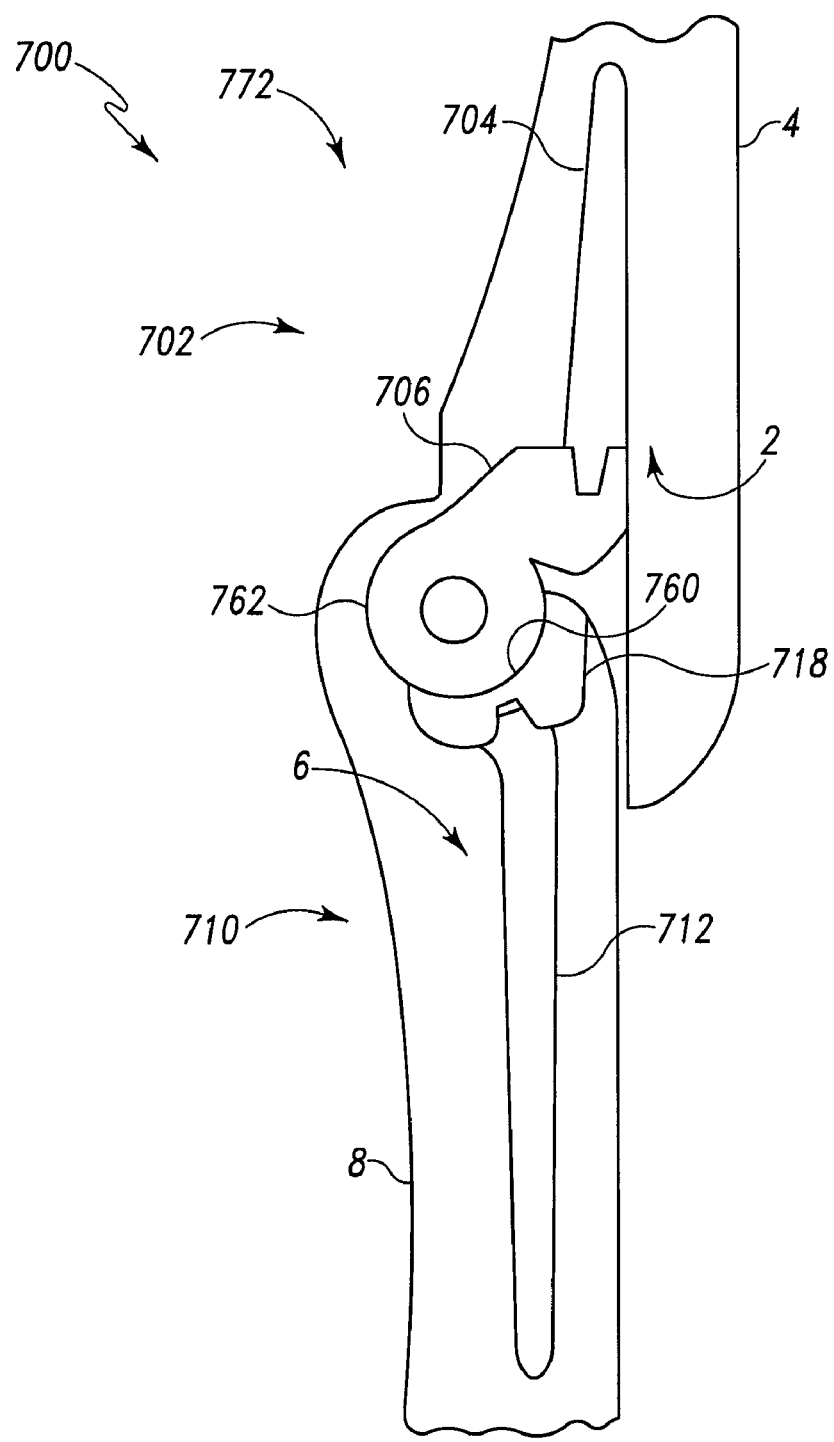
FIG. 40 is an medial/lateral view partially in cross section of a further embodiment of the present invention of an elbow prosthesis assembly including an unconstrained elbow prosthesis assembly shown in position implanted in a humerus and an ulna.
Figure 41:
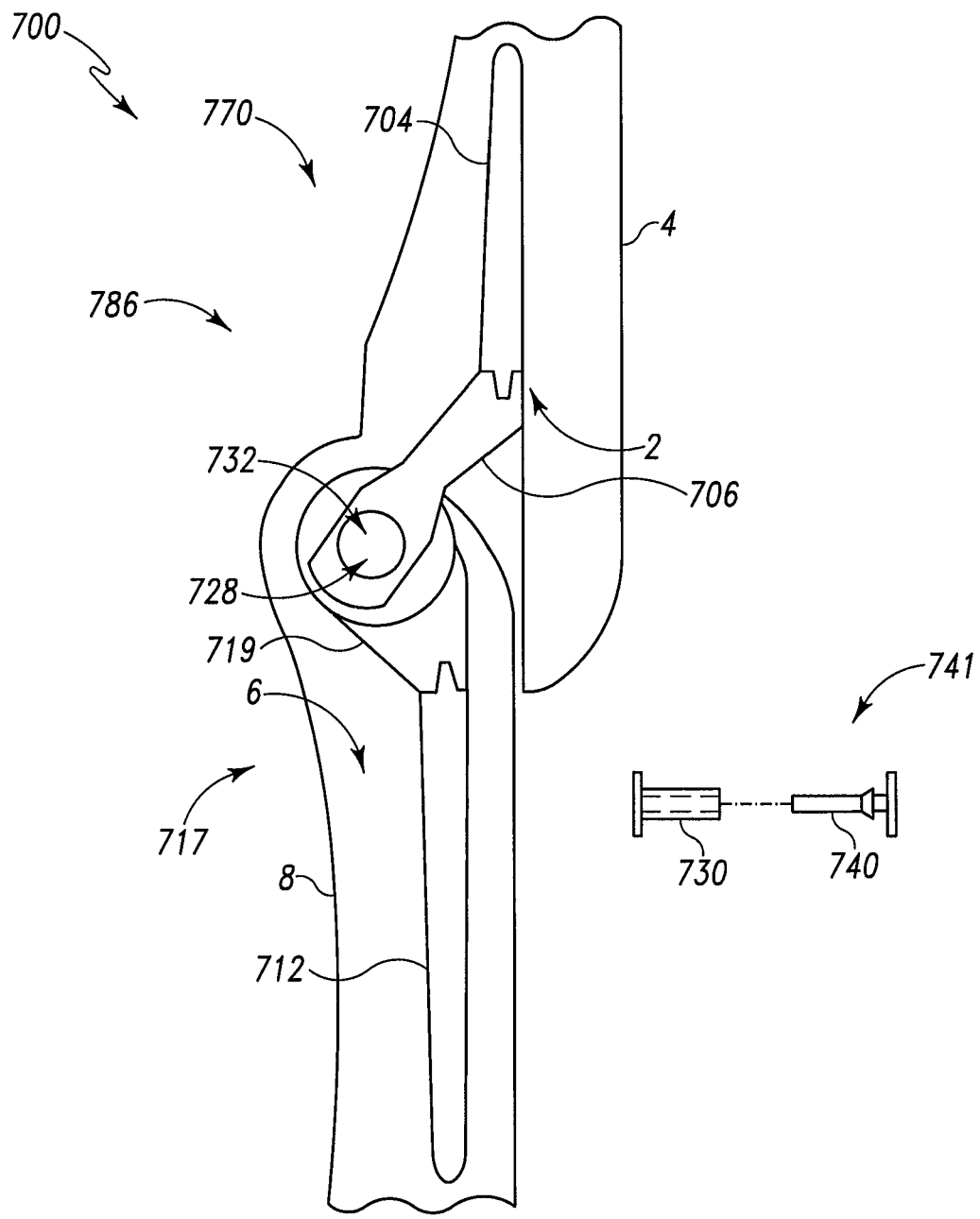
FIG. 41 is an medial/lateral view partially in cross section of an semi-constrained elbow prosthesis assembly shown in position implanted in a humerus and an ulna corresponding to the unconstrained elbow prosthesis assembly of FIG. 40.

Referring now to FIGS. 40 and 41, yet another embodiment of the present invention is shown as total elbow prosthesis 700. The total elbow prosthesis 700 includes an unconstrained elbow prosthesis 772 as well as a semi-constrained elbow prosthesis 770. The total elbow prosthesis 700 is different than the total elbow prosthesis 600 of FIGS. 37 through 39 in that the total elbow prosthesis 700 is a reverse design. For example and as shown in s 40 and 41, the ulnar component is convex and the humeral component is concave.

Referring now to FIG. 40, the unconstrained elbow prosthesis 772 is shown in greater detail. The unconstrained elbow prosthesis 772 includes an ulnar unconstrained assembly 702 which mates with a humeral unconstrained assembly 710 to form the unconstrained elbow prosthesis 772.

The ulnar-unconstrained assembly 702 includes an ulnar stem component 704, which is fitted in cavity 2 of the ulna 4. An ulnar unconstrained articulating component 706 is removably secured to the ulnar stem component 704 to form the ulnar unconstrained assembly 702.

The ulnar articulating component 706 is slidably connected to the ulnar stem component 704. The ulnar articulating component includes an ulnar articulating surface 762. The ulnar articulating surface 762, as shown in FIG. 40, is convex, making the prosthesis 772 a reverse prosthesis with articulating surfaces reverse those of an anatomical joint.

The unconstrained humeral assembly 710 includes a humeral stem component 712, which is fitted into cavity 6 of the humerus 8. An unconstrained humeral articulating component 718 is removably attached to the humeral stem component 712. The unconstrained humeral articulating component 718 includes a humeral articulating surface 760, which is concave. The humeral articulating surface 760 cooperates with the ulnar articulating surface 762 to provide the unconstrained motion of the unconstrained elbow prosthesis 772.

Referring now to FIG. 41, the semi-constrained prosthesis 770 is shown. The semi-constrained prosthesis 770 includes a semi-constrained ulnar assembly 786, which is pivotably secured to semi-constrained humeral assembly 717 by connector assembly 741.

The connector assembly 741 may include, for example, a pin 730, which cooperates with a cap 740 to provide the connector assembly 741.

The ulnar assembly 786 includes the ulnar stem component 704, which is fitted into cavity 2 of the ulna 4. An ulnar semi-constrained articulating component 706 is fitted to the ulnar stem component 704 to form the ulnar semi-constrained assembly 786. The ulnar semi-constrained articulating component 706 includes an ulnar opening 732 for receiving the connector assembly 741.

The semi-constrained humeral assembly 717 includes the humeral stem component 712, which is fitted into cavity 6 of the humerus 8. Humeral semi-constrained articulating component 719 is removably secured to the humeral stem component 712. The semi-constrained humeral articulating component 719 defines a humeral opening 728 for receiving the connector assembly 741.

Figure 42:
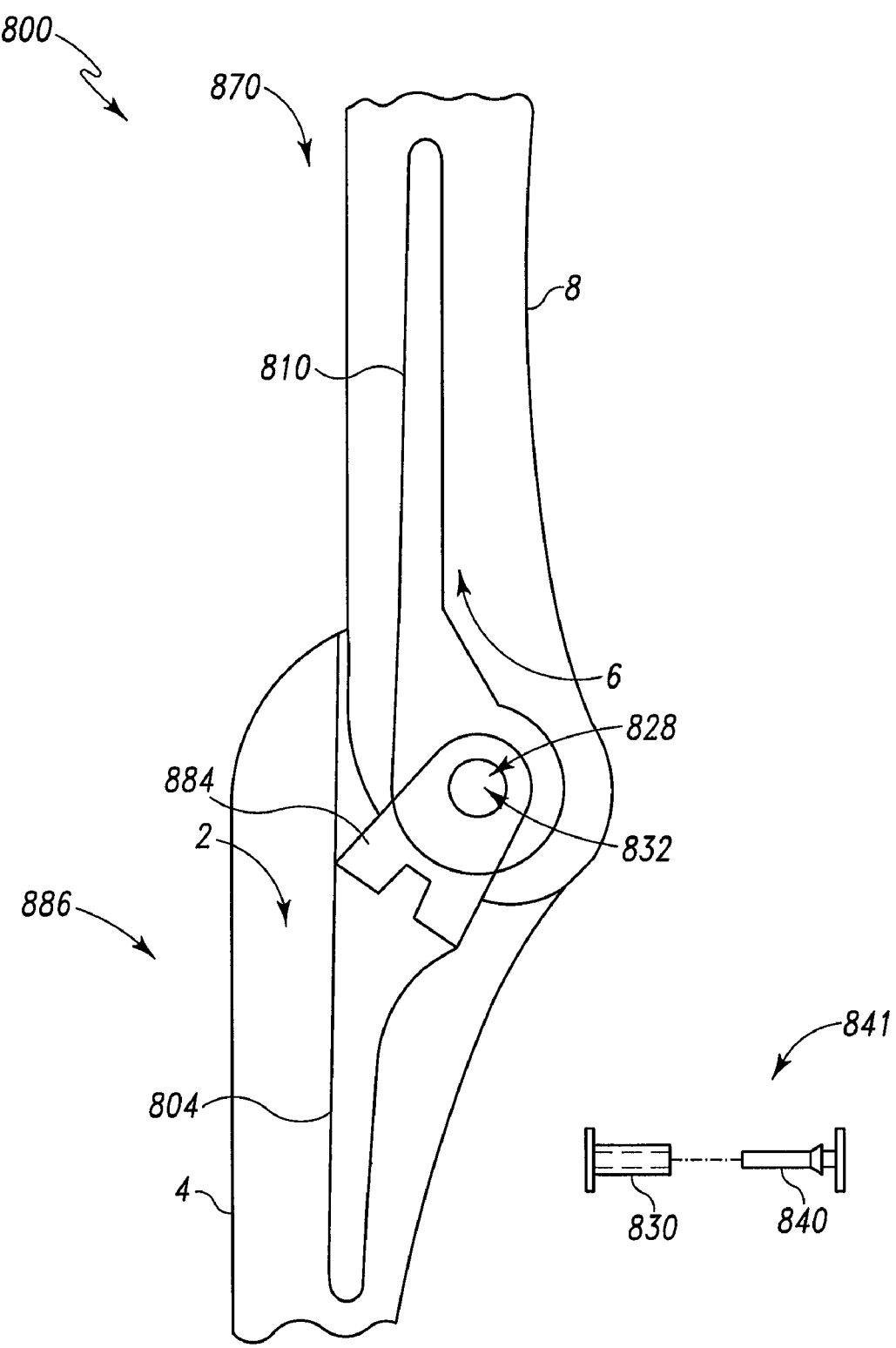
FIG. 42 is an medial/lateral view partially in cross section of a further embodiment of the present invention of an elbow prosthesis assembly including an semi-constrained elbow prosthesis assembly shown in position implanted in a humerus and an ulna.
Figure 43:
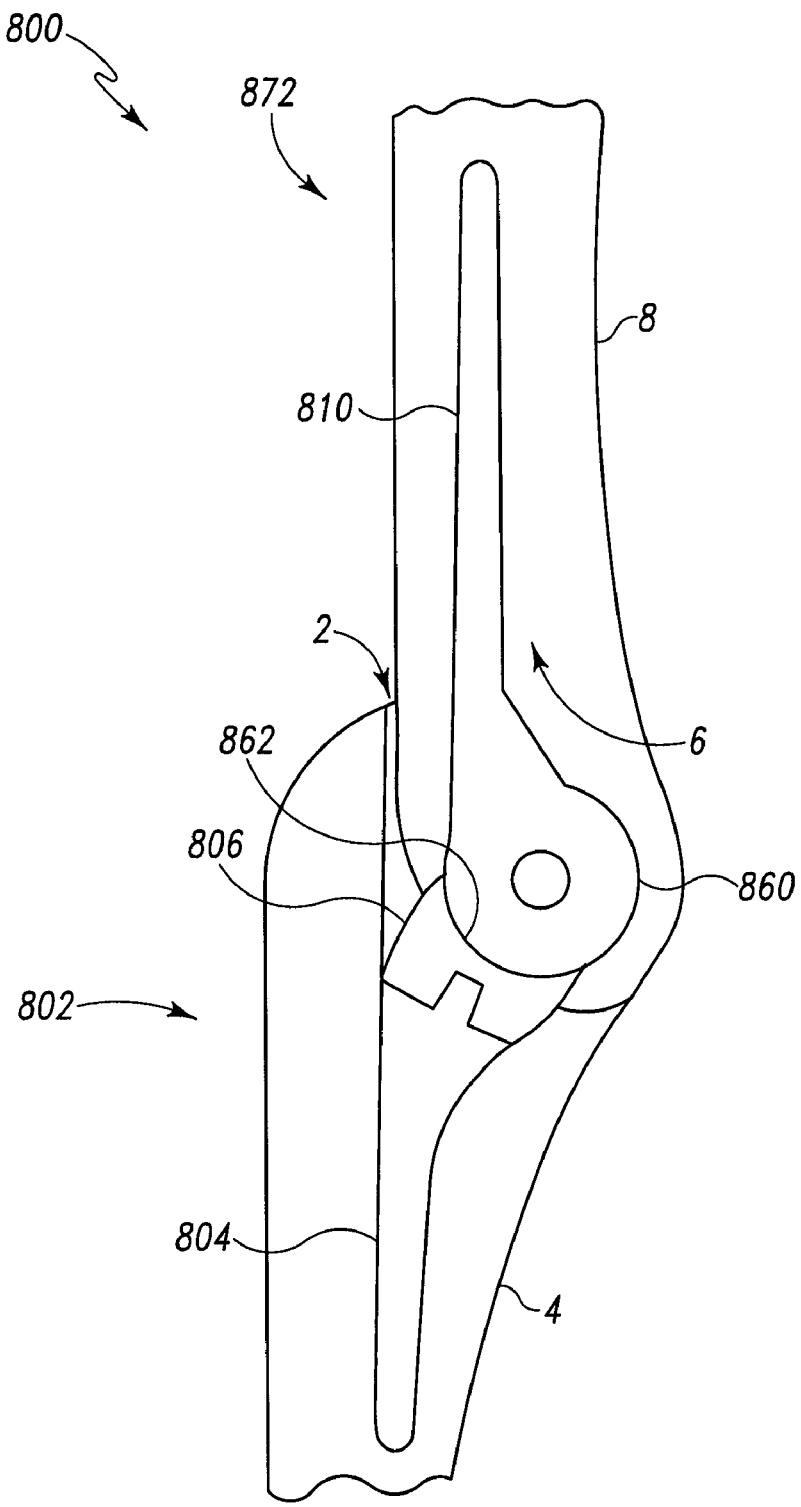
FIG. 43 is an medial/lateral view partially in cross section of an unconstrained elbow prosthesis assembly shown in position implanted in a humerus and an ulna corresponding to the semi-constrained elbow prosthesis assembly of FIG. 42.

Referring now to FIGS. 42 and 43, yet another embodiment of the present invention is shown as total elbow prosthesis 800. The total elbow prosthesis 800 is similar to the total elbow prosthesis 600 and 700, except that the total elbow prosthesis 800 includes a unitary or one-piece humeral component. Elbow prosthesis 800 includes a semi-constrained elbow prosthesis 870 as well as an unconstrained elbow prosthesis 872.

Referring now to FIG. 42, the semi-constrained elbow prosthesis 870 is shown. The semi-constrained elbow prosthesis 870 includes a humeral component 810 as well a semi-constrained ulnar assembly 886. The humeral component 810 defines a humeral opening 828 through which connector assembly 841 is slidably fitted.

The semi-constrained prosthesis 870 further includes the ulnar semi-constrained assembly 886. The ulnar semi-constrained assembly 886 includes an ulna stem component 804, which is fitted into cavity 2 of the ulna 4. An ulnar semi-constrained articulating component 884 is removably fitted to the ulnar stem component 804. The ulnar semi-constrained articulating component 884 defines an ulnar opening 832 through which connector assembly 841 is fitted.

The semi-constrained prosthesis 870 further includes the connector assembly 841. The connector assembly 841 includes a pin 830 to which a cap 840 is matingly fitted.

Referring now to FIG. 43, the unconstrained elbow prosthesis 872 is shown. The unconstrained elbow prosthesis 872 includes the unitary humeral component 810, which is fitted into cavity 6 of the humerus 8. The unconstrained prosthesis 872 further includes an ulnar unconstrained assembly 802 having ulnar stem component 804 which is fitted to the cavity 2 of the ulna 4. An ulnar unconstrained articulating component 806 is fitted to the ulnar stem component 804. The ulnar unconstrained articulating component 806 includes an ulnar contact surface 862, which is matingly fitted to humeral articulating surface 860 of the humeral component 810. The humeral articulating surface 860 is convex or anatomical.

Since the humeral component 810 is unitary, to convert an unconstrained elbow prosthesis 872 to a semi-constrained elbow prosthesis 870, the humeral component 810 must either be removed from the humerus or the condylar portion of the humerus 8 may need to be partially removed so that the connector 841 may be inserted into the humeral opening 828.

Figure 44:
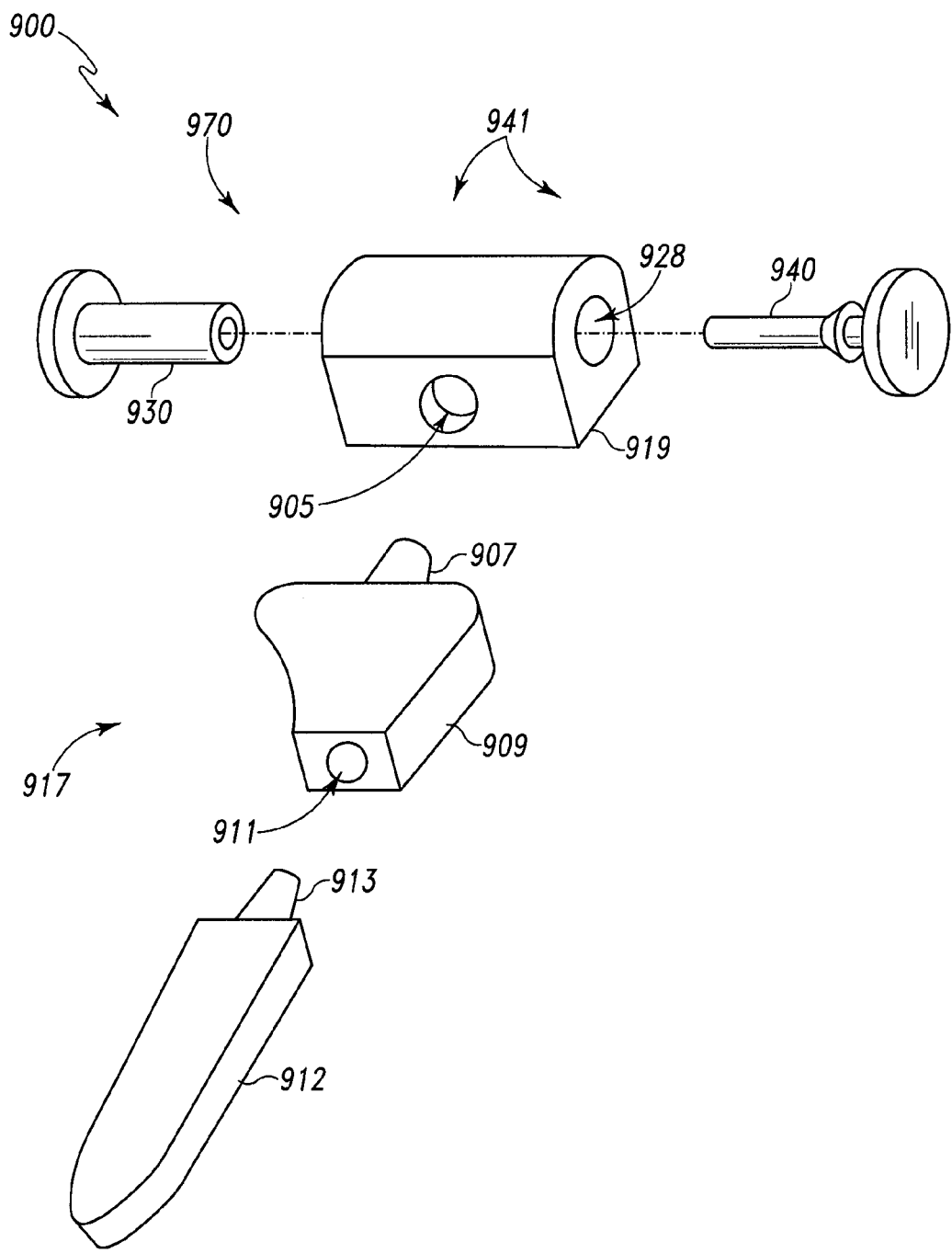
FIG. 44 is an exploded perspective view of yet another embodiment of the present invention in the form of a three piece semi-constrained humeral elbow prosthesis assembly that is a part of a semi-constrained elbow prosthesis assembly for implantation into a humerus and an ulna.
Figure 45:
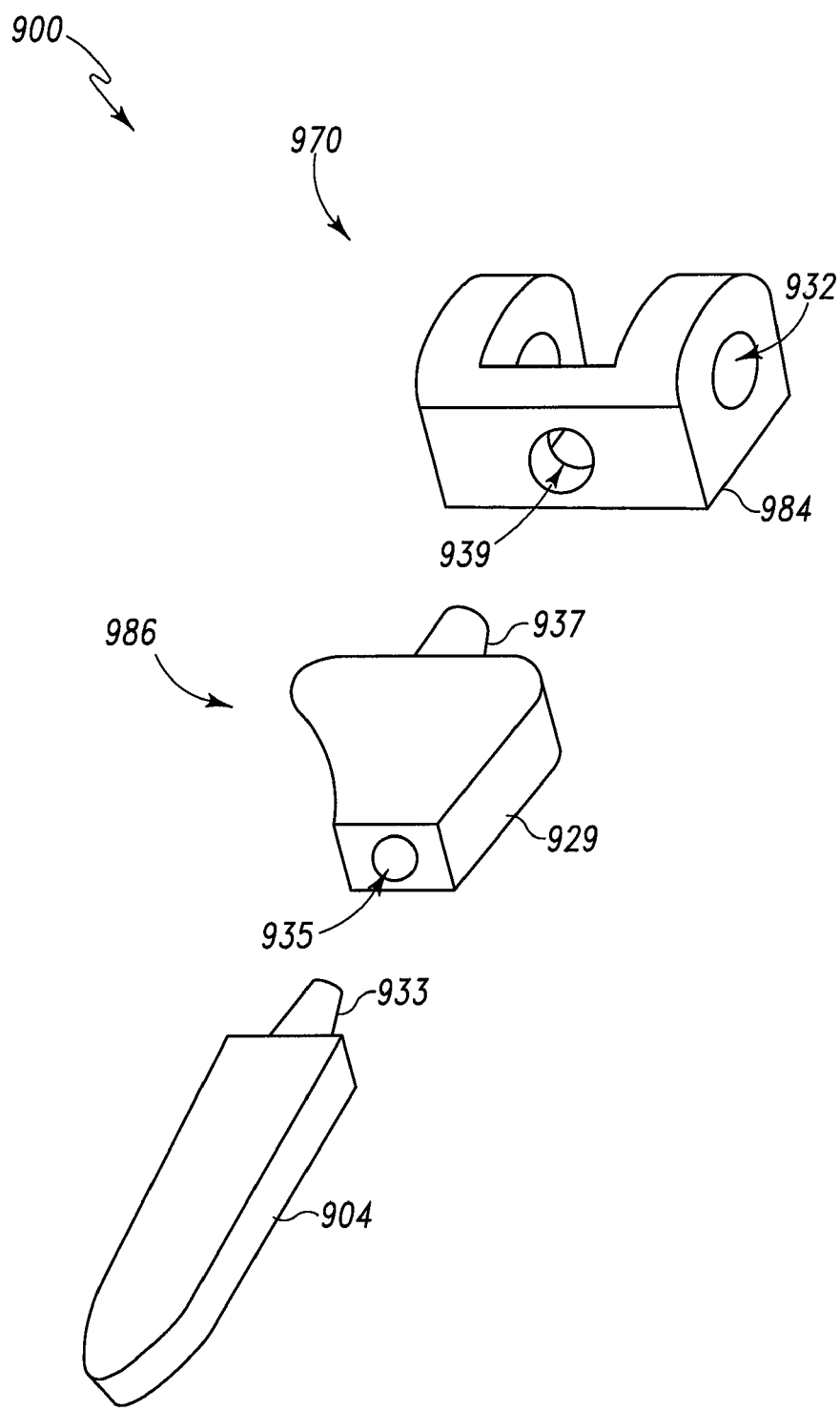
FIG. 45 is an exploded perspective view of a semi-constrained ulnar elbow prosthesis assembly that is a part of a semi-constrained elbow prosthesis assembly of the semi-constrained elbow prosthesis assembly of FIG. 44.
Figure 46:
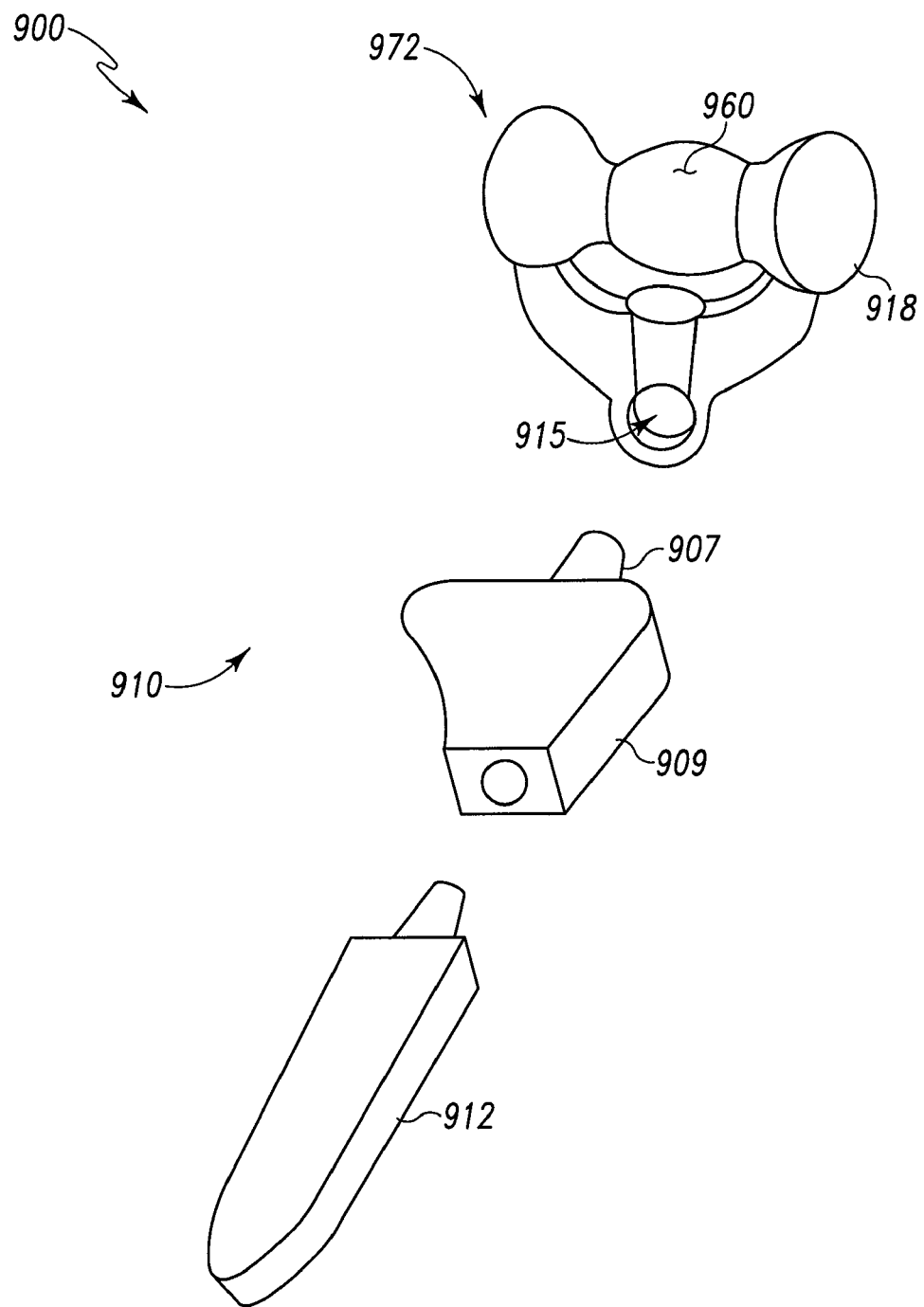
FIG. 46 is a perspective view of a three piece unconstrained humeral elbow prosthesis assembly that is part of the unconstrained elbow prosthesis assembly of FIG. 45A.

Referring now to FIGS. 44 through 46, yet another embodiment of the present invention is shown as total elbow prosthesis 900. The total elbow prosthesis 900 is different than the elbow prosthesis 600, 700 or 800 in that the total elbow prosthesis 900 includes a three-piece humeral assembly as well as a three-piece ulnar assembly.

Referring now to FIGS. 44 and 45, semi-constrained elbow prosthesis 970 of the total elbow prosthesis 900 is shown. The semi-constrained elbow prosthesis 900 includes humeral semi-constrained assembly 917 as shown in FIG. 44.

The humeral semi-constrained assembly 917 includes three 3 components. The humeral semi-constrained assembly 917 includes humeral stem component 912. The humeral stem component 912 may include, for example, an exterior protrusion 913. The semi-constrained humeral assembly 917 further includes a condylar component 909, which is fitted to the humeral stem component 912. The humeral condylar component 909 may include an internal cavity 911, which matingly receives the external protrusion 913 of the stem 912.

The humeral semi-constrained assembly 917 further includes a humeral semi-constrained articulating component 919, which includes an internal cavity 905 to which external protrusion 907 of the condylar component 909 is matingly fitted. The humeral semi-constrained articulating component 919 includes opening 928 for receiving the connector assembly 941. The connector assembly 941 includes pin 930 to which cap 940 is secured.

The semi-constrained elbow prosthesis 970 further includes, as shown in FIG. 45, an ulnar semi-constrained assembly 986. The ulnar semi-constrained assembly 986 includes an ulnar stem 904 from which a protrusion 933 extends. The ulnar semi-articulating assembly 986 further includes an ulnar condylar component 929, which is fitted to the ulnar stem 904 by means of, for example, an ulnar condylar cavity 935, which receives the ulnar stem protrusion 933.

The ulnar semi-constrained assembly 986 further includes an ulnar semi-constrained articulating component 984, which includes an articulating component cavity 939 for receiving ulnar condylar portion protrusion 937. The ulnar semi-constrained articulating component 984 defines ulnar opening 932 for receiving the connector assembly 941.

Figure 45A:
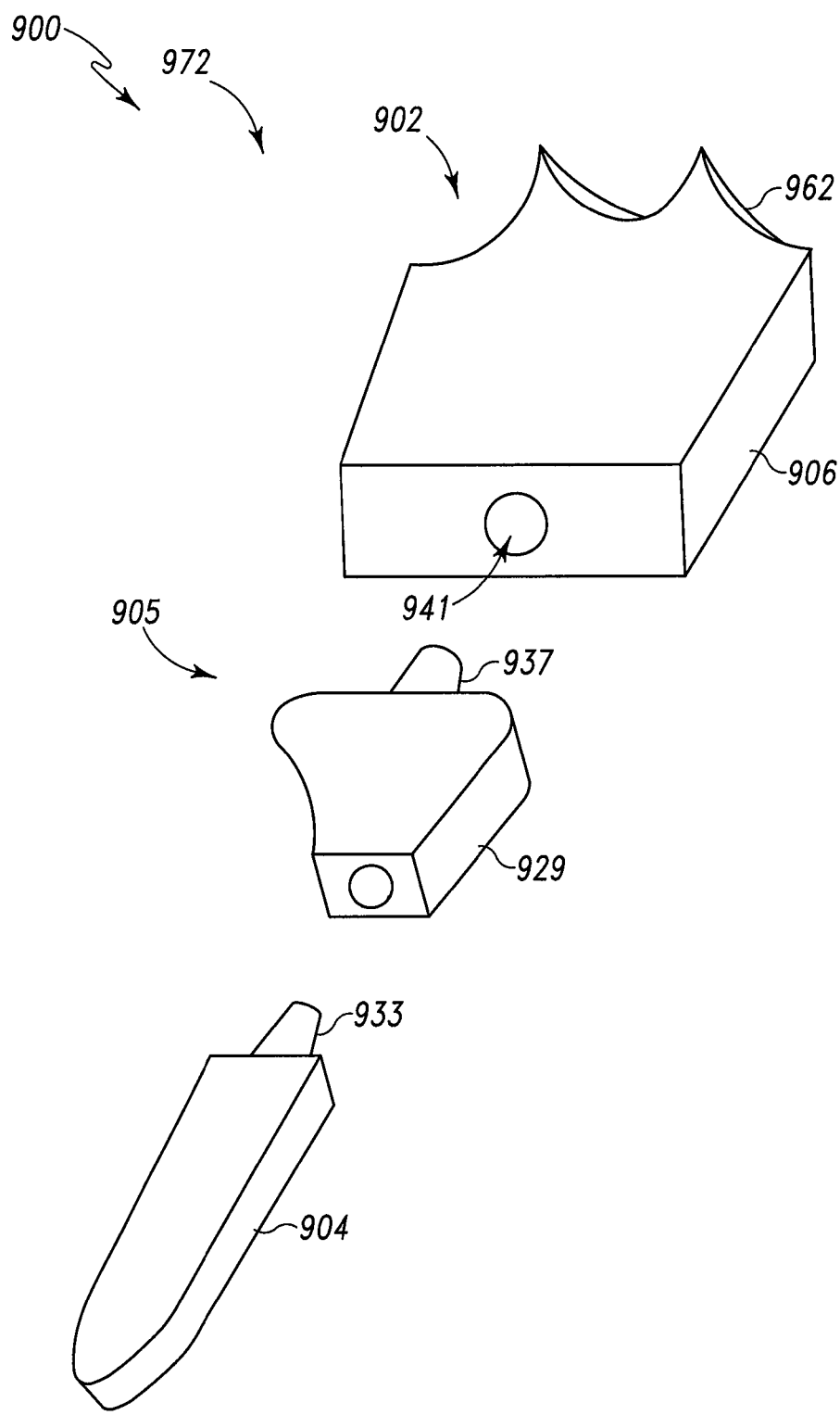
FIG. 45A is an exploded perspective view of the three piece unconstrained ulnar elbow prosthesis assembly that is part of an unconstrained elbow prosthesis assembly corresponding to the semi-constrained elbow prosthesis assembly of FIGS. 44 and 45.

Referring now to FIGS. 45A and 46, total elbow prosthesis 900 further includes an unconstrained elbow prosthesis 972. The unconstrained elbow prosthesis 972 includes, as is shown in FIG. 46, a humeral unconstrained assembly 910. The humeral unconstrained assembly 910 includes humeral stem component 912 to which humeral condylar component 909 is secured. The humeral unconstrained assembly 910 further includes a humeral unconstrained articulating component 918, which is secured to the humeral condylar component in any suitable manner.

For example, the humeral unconstrained articulating component 918 includes a cavity 915, which matingly receives condylar component protrusion 907. The humeral unconstrained articulating component 918 includes a humeral articulating surface 960 for mating contact with ulnar articulating surface 962.

Referring again to FIG. 45A, the unconstrained elbow prosthesis 972 further includes ulnar unconstrained assembly 905. The ulnar-unconstrained assembly 905 includes the ulnar stem component 904 and the ulnar condylar component 929, which is removably secured to the ulnar stem component 904. The ulnar unconstrained assembly 905 further includes ulnar unconstrained articulating component 906. The ulnar unconstrained articulating component 906 may include an ulnar unconstrained articulating component cavity 941 for receiving the ulnar condylar component protrusion 937. The ulnar unconstrained articulating component articulating component 906 defines ulnar articulating surface 962 which mates with humeral articulating surface 960 of the humeral unconstrained assembly 910. Ulnar unconstrained articulating component 906 operably is connected to the ulnar condylar component 929, which is in turn connected to the ulnar stem component 904.

Figure 46A:
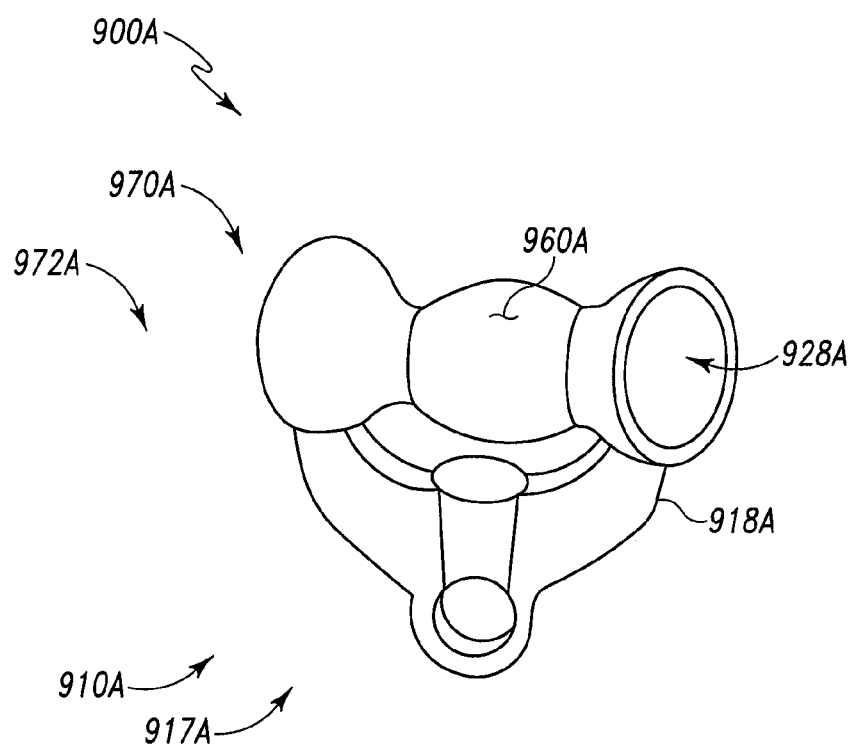
FIG. 46A is a perspective view of an unconstrained humeral articulating component that is a part of the unconstrained elbow prosthesis assembly and also serves as a semi-constrained humeral articulating component of the semi-constrained elbow prosthesis assembly of FIGS. 44 and 45.

According to another embodiment of the present invention and referring now to FIG. 46A, a prosthesis 900A is shown in which the three-part humeral unconstrained assembly may also be used as a semi-constrained assembly. For example the humeral articulating assembly may be in the form of a humeral semi-constrained assembly 910A including humeral unconstrained articulating component 918A having a central opening 928A in the humeral articulating component 918A for semi-constrained use. The humeral articulating component 918A may also have an articulating surface 960 for unconstrained use.

Figure 47:
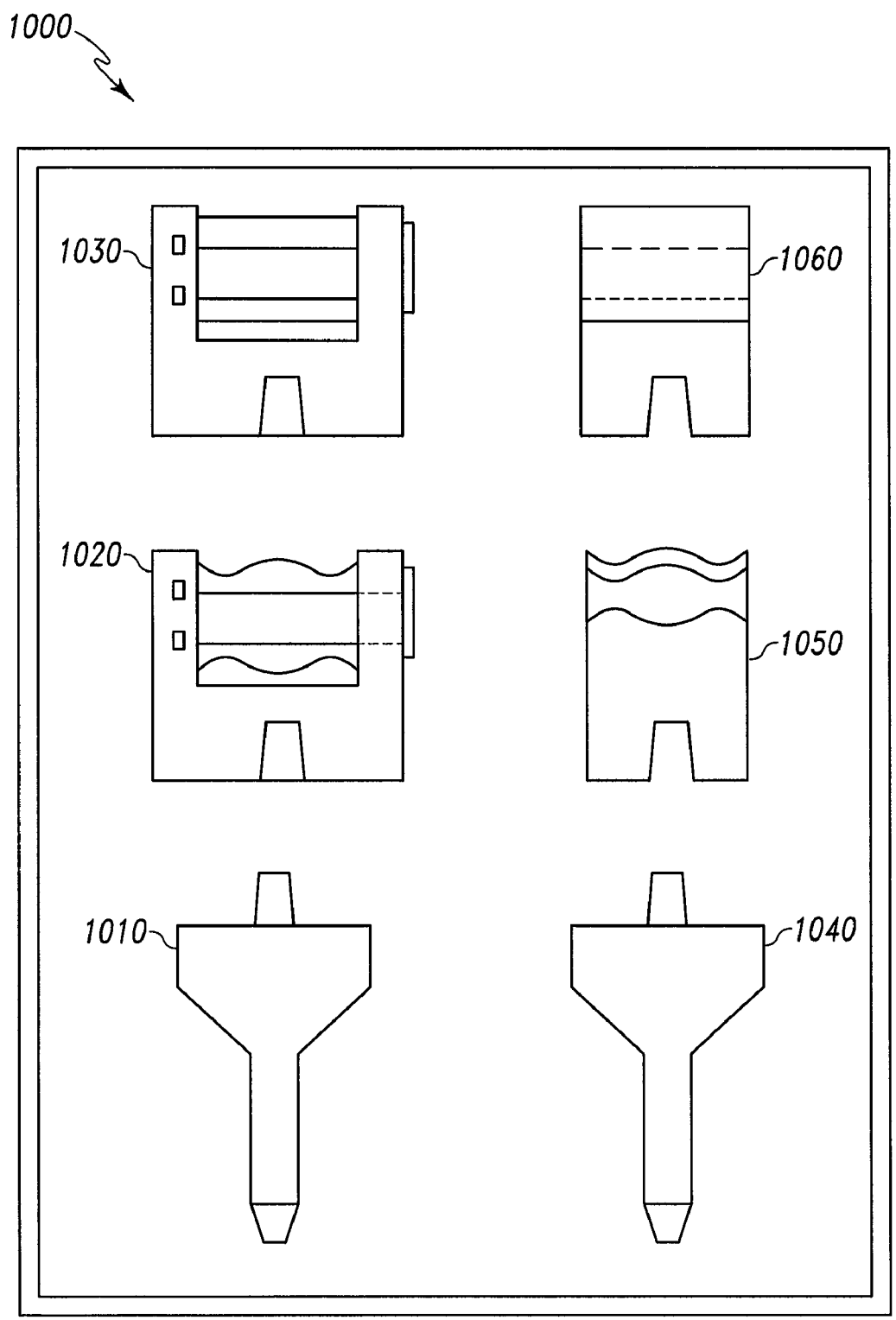
FIG. 47 is a plan view of a kit for performing arthroplasty in accordance with yet another embodiment of the present invention.

According to the present invention and referring now to FIG. 47, a kit 1000 according to the present invention is shown. The kit 1000 includes a humeral stem component 1010 for cooperation with the humerus. The kit 1000 further includes a first humeral hinge component 1020 for cooperation with the humeral stem component 1010. The first humeral hinge component 1020 may, as is shown in FIG. 47, be adapted for use in an unconstrained elbow prosthesis. The kit 1000 further includes a second humeral hinge component 1030 for cooperation with the humeral stem component 1010 to form a semi-constrained humeral assembly.

The kit 1000 further includes an ulnar stem component 1040 for cooperation with the ulna. The kit 1000 further includes a first ulnar hinge component 1050 for cooperation with the ulnar stem component 1040 to form an unconstrained ulnar elbow assembly. The kit 1000 further includes a second ulnar hinge component 1060 for cooperation with the ulnar stem component 1040. The second ulnar hinge component 1060 may, for example, be used to form an ulnar semi-constrained assembly.

Figure 48:
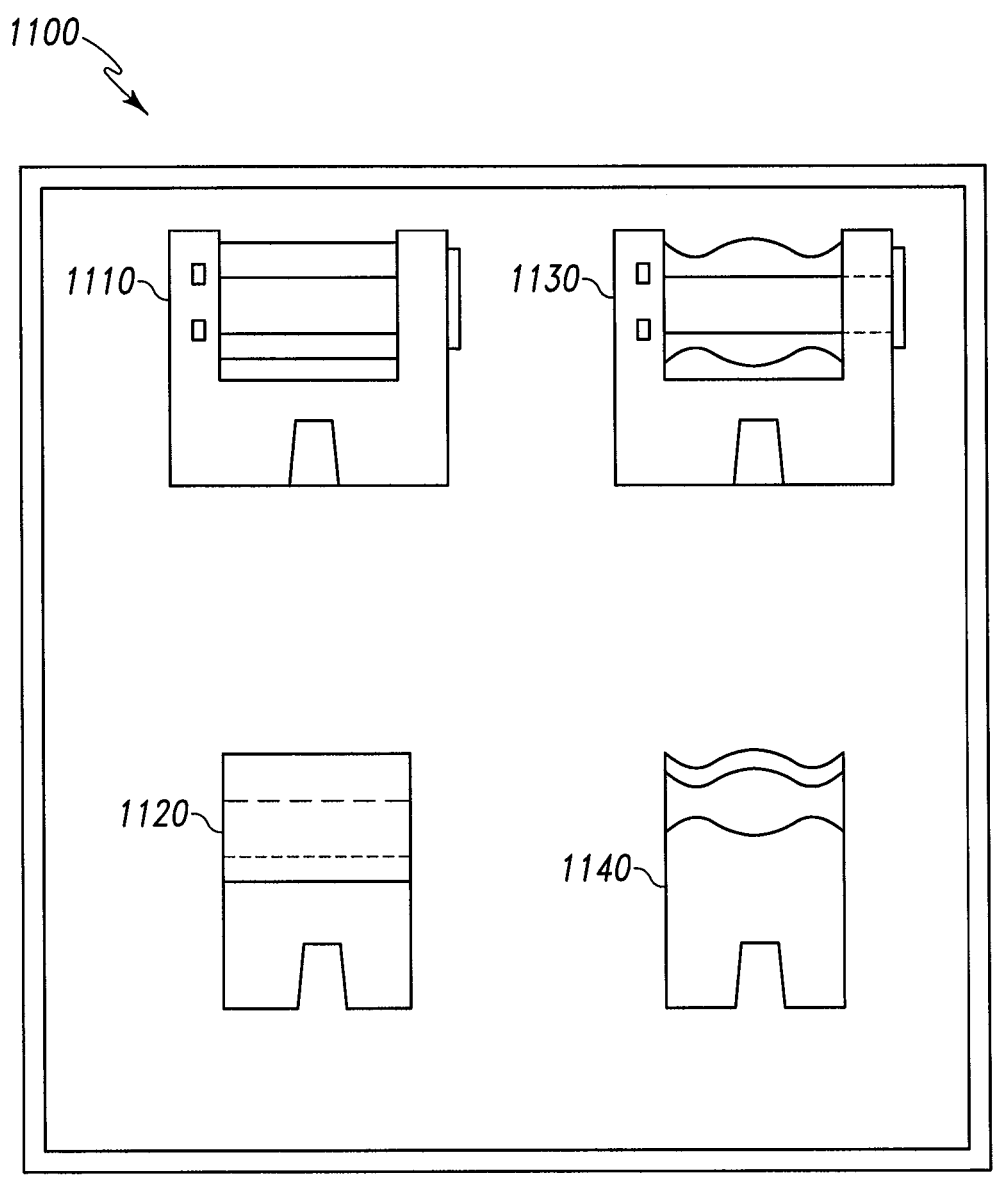
FIG. 48 is a plan view of a repair kit for performing revision arthroplasty in accordance with another embodiment of the present invention.

Referring now to FIG. 48, yet another embodiment of the present invention is shown as kit 1100. The kit 1100 is in the form of a repair kit to be used with ulnar and humeral stem components. The kit 1100 includes a first humeral hinge component 1110. The first humeral hinge component 1110 may, for example, be adapted for use in a semi-constrained elbow prosthesis. The kit 1100 further includes a first ulnar hinge component 1120 which cooperates with the first humeral hinge component 1110 to form a semi-constrained elbow prosthesis.

The kit 1100 further includes a second humeral hinge component 1130. The first humeral hinge component 1110 and the second humeral hinge component 1130 are adapted for use with a common humeral stem component (not shown). The kit 1100 further includes a second ulnar hinge component 1140. The second ulnar hinge component 1140 may, for example and as shown in FIG. 48, be an unconstrained ulnar hinge component. The second ulnar hinge component 110 may, for example, cooperate with the second humeral hinge component 1140 to provide for an unconstrained elbow prosthesis. First ulnar hinge component 1120 and the second ulnar hinge component 1130 are adapted for use with a common ulnar stem component not shown.

Figure 49:
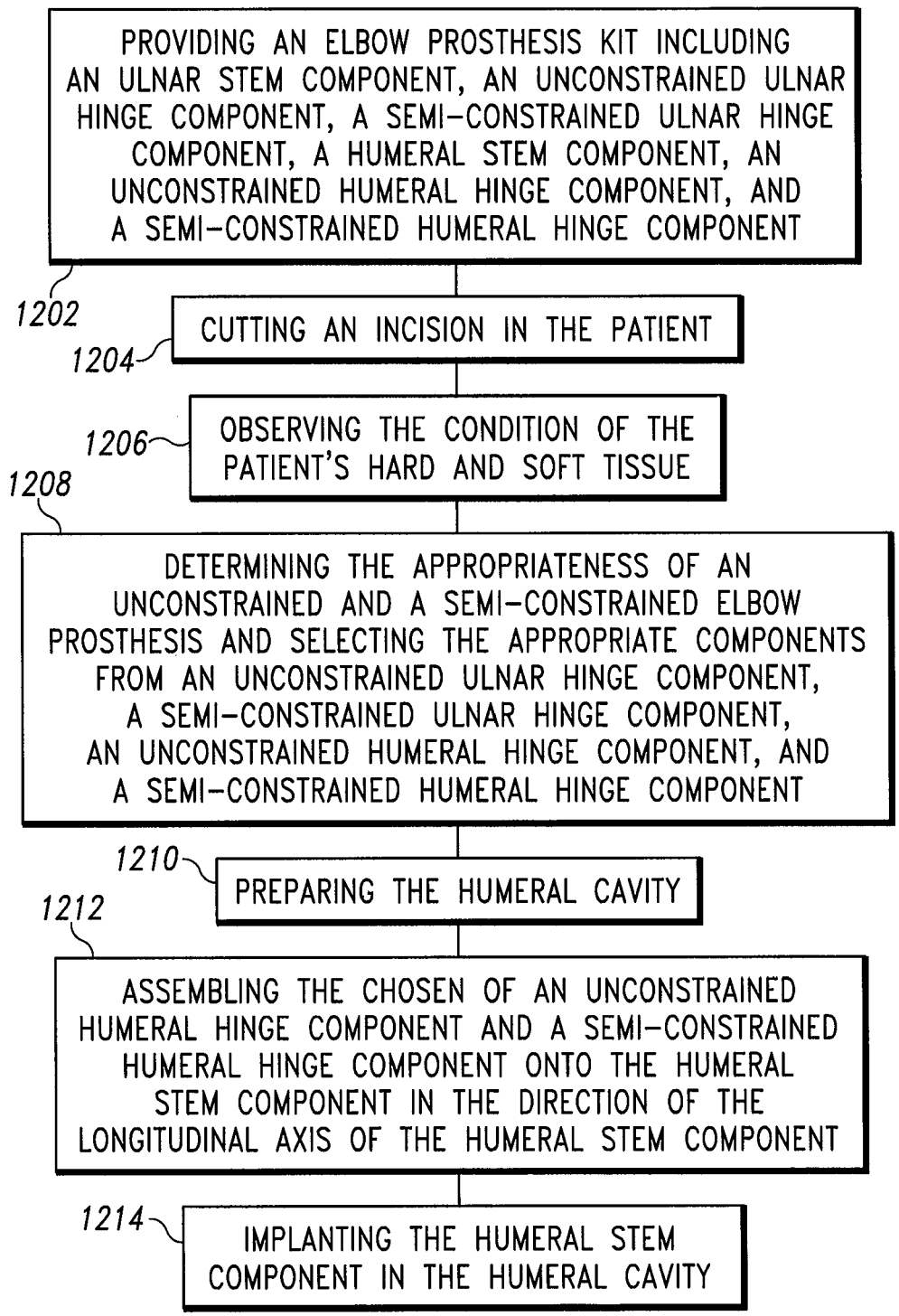
FIG. 49 is a flow chart of a method for performing total elbow arthroplasty in accordance with yet another embodiment of the present invention.

Referring now to FIG. 49, yet another embodiment of the present invention is shown as surgical procedure 1200. The surgical procedure 1200 includes a first step 1202 of providing an elbow prosthesis kit, including an ulnar stem component, an unconstrained ulnar hinge component, a semi-constrained ulnar hinge component, a humeral stem component, an unconstrained humeral hinge component, and a semi-constrained humeral hinge component. The surgical procedure 1200 further includes a second step 1204 of cutting an incision in the patient and a third step 1206 of observing the condition of the patient's hard and soft tissue.

The method 1200 further includes a fourth step 1208 of determining the appropriateness of an unconstrained and semi-constrained elbow prosthesis and selecting the appropriate components from an unconstrained ulnar hinge component, a semi-constrained ulnar hinge component, a unconstrained humeral hinge component, and a semi-constrained humeral hinge component.

The method 1200 further includes a fifth step 1210 of preparing the humeral cavity and a sixth step 1212 of assembling the chosen of an unconstrained humeral hinge component and a semi-constrained humeral hinge component onto the humeral stem component in the direction of the longitudinal axis of the humeral stem component.

The method 1200 further includes a seventh step 1214 of implanting the humeral stem component into the humeral cavity.

Figure 50:
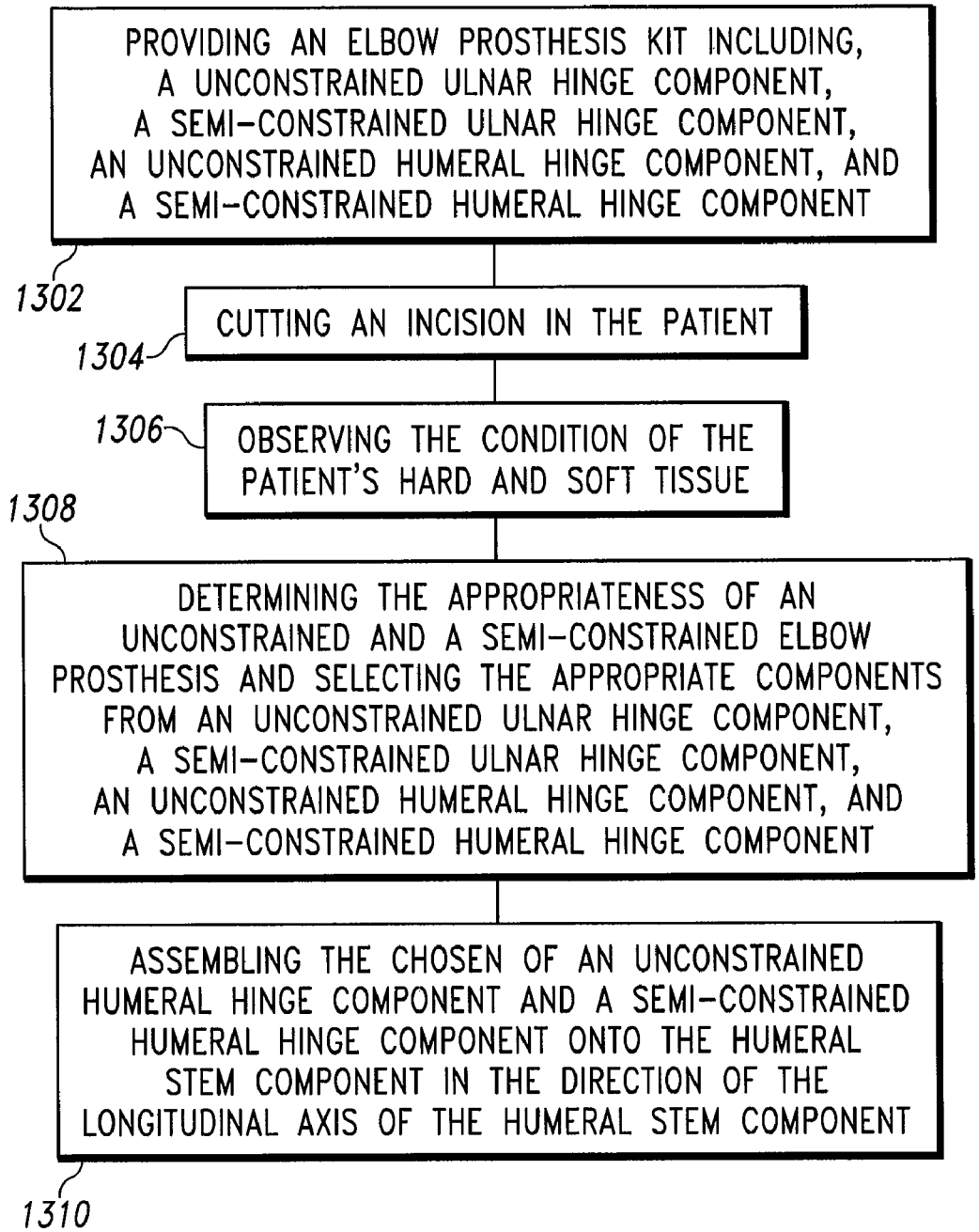
FIG. 50 is a flow chart of another method for performing total elbow revision arthroplasty in accordance with another embodiment of the present invention.

Referring now to FIG. 50, yet another embodiment of the present invention is shown as method 1300 for providing total elbow revision arthroplasty. The method 1300 includes a first step 1302 of providing an elbow prosthesis kit including an unconstrained ulnar hinge component, a semi-constrained ulnar hinge component, an unconstrained humeral hinge component, and a semi-constrained humeral hinge component. The method 1300 further includes a second step 1304 of cutting an incision in the patient and a third step 1306 of observing the condition of the patient's hard and soft tissue. The method 1300 further includes a fourth step 1308 of determining the appropriateness of an unconstrained and semi-constrained elbow prosthesis and selecting the appropriate components from an unconstrained ulnar hinge component, a semi-constrained ulnar hinge component, an unconstrained humeral hinge component, and a semi-constrained humeral hinge component. The method includes a fifth step 1310 of assembling the chosen of an unconstrained humeral hinge component and a semi-constrained humeral hinge component onto the humeral stem component in the direction of the longitudinal axis of the humeral stem component.

Although the present invention and its advantages have been described in detail, it should be understood that various changes, substitutions, and alterations can be made therein without departing from the spirit and scope of the present invention as defined by the appended claims.

I claim:

1. An ulnar assembly for use with a humeral component to form an elbow prosthesis, said ulnar component comprising:
   a stem component including a portion thereof defining a stem for implantation in a cavity formed in the ulna, said first component defining a longitudinal axis thereof generally coincident with the longitudinal axis of the ulna;
   a semi-constrained component attachable to said stem component, said semi-constrained component attachable and removable from said stem component along the longitudinal axis of the stem component, wherein one of said stem component and said semi-constrained component comprises an external taper and wherein the other of said stem component and said semi-constrained component defines an internal taper therein adapted to receive said external taper; and
   an unconstrained component attachable to said stem component, said unconstrained component attachable and removable from said stem component along the longitudinal axis of the stem component, wherein one of said stem component and said unconstrained component comprises an external taper and wherein the other of said stem component and said unconstrained component defines an internal taper therein adapted to receive said external taper.

2. The ulnar assembly of claim 1, wherein said unconstrained component comprises a hinge portion thereof, the hinge portion defining a pivot axis thereof, said unconstrained component adapted to permit bone to remain on the ulna through the pivot axis after implantation of the prosthesis into the ulna.

3. The ulnar assembly of claim 1:
   wherein said semi-constrained component defines a opening therein; and
   wherein the opening of said semi-constrained component is cooperable with a pin and the humeral component to form a semi constrained prosthesis.

4. The ulnar assembly of claim 1:
   further comprising a third component; and
   wherein said third portion is rotatably connected to one of said semi-constrained portion and unconstrained portion about an axis normal to the longitudinal axis of said stem component.

5. The ulnar assembly of claim 1:
   wherein one of said stem component and said unconstrained component comprises a cylinder; and
   wherein the other of said stem component and said unconstrained component defines a cylindrical opening therein adapted to receive said cylinder.

6. The ulnar assembly of claim 1, wherein the rotation of one of said unconstrained component and said semi-constrained component with respect to said stem component is limited to less than 360 degrees.

7. The ulnar assembly of claim 6, wherein rotation of one of said unconstrained component and said semi-constrained component with respect to said stem component is limited to 10 to 60 degrees.

8. The ulnar assembly of claim 1:
   wherein both of said unconstrained component and said semi-constrained component include a contact surface adapted for cooperation with a humeral component; and
   wherein both of said unconstrained component and said semi-constrained component may be freely separated from the humeral component in a direction normal to the contact surface.

9. The ulnar assembly of claim 8, wherein the contact surface of said unconstrained component is generally concave.

10. The ulnar assembly of claim 8, wherein the contact surface of said semi-constrained component is generally convex.

11. The ulnar assembly of claim 1, wherein both of said unconstrained component and said semi-constrained component is adapted to be rotatably interlocked with a humeral component.

* * * * *